(12) United States Patent
Thompson et al.

(10) Patent No.: US 6,685,941 B1
(45) Date of Patent: Feb. 3, 2004

(54) METHODS OF TREATING AUTOIMMUNE DISEASE VIA CTLA-4IG

(75) Inventors: Craig B. Thompson, Ann Arbor, MI (US); Carl H. June, Rockville, MD (US)

(73) Assignees: The Regents of the University of Michigan, Ann Arbor, MI (US); The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 08/385,194

(22) Filed: Feb. 7, 1995

Related U.S. Application Data

(63) Continuation of application No. 08/076,071, filed on Jun. 10, 1993, now abandoned, which is a continuation-in-part of application No. PCT/US93/03155, filed on Apr. 6, 1993, which is a continuation of application No. 07/864,805, filed on Apr. 7, 1992, now abandoned, which is a continuation of application No. 07/864,807, filed on Apr. 7, 1992, now abandoned, which is a continuation of application No. 07/864,866, filed on Apr. 7, 1992, now abandoned, which is a continuation-in-part of application No. 07/275,433, filed on Nov. 23, 1988, now abandoned.

(51) Int. Cl.$^7$ ............................. A61K 38/17; C07K 14/705

(52) U.S. Cl. ........................... 424/134.1; 424/192.1; 514/2; 514/8; 514/885; 530/350; 530/387.3

(58) Field of Search ......................... 514/2, 12, 8, 885; 424/133.1, 130.1, 144.1, 173.1, 134.1, 192.1; 530/350, 866, 868, 387.1, 388.2, 388.73, 387.3; 435/326, 343.1

(56) References Cited

U.S. PATENT DOCUMENTS

| | | | |
|---|---|---|---|
| 4,654,210 A | | 3/1987 | Kung et al. |
| 5,116,964 A | | 5/1992 | Capon et al. |
| 5,434,131 A | * | 7/1995 | Linsley et al. ............. 514/2 |
| 5,521,288 A | | 5/1996 | Linsley et al. |
| 5,580,756 A | * | 12/1996 | Linsley et al. |
| 5,770,197 A | * | 6/1998 | Linsley et al. |
| 5,773,253 A | * | 6/1998 | Linsley et al. |
| 5,844,095 A | * | 12/1998 | Linsley et al. |
| 5,851,795 A | * | 12/1998 | Linsley et al. |
| 5,885,796 A | * | 3/1999 | Linsley et al. |
| 5,968,510 A | * | 10/1999 | Linsley et al. |
| 5,977,318 A | * | 11/1999 | Linsley et al. |
| 6,090,914 A | * | 7/2000 | Linsley et al. |

FOREIGN PATENT DOCUMENTS

| | | |
|---|---|---|
| EP | 0336379 | 10/1989 |
| EP | 0440373 | 8/1991 |
| EP | 0448057 | 9/1991 |
| WO | WO 90/05541 | 5/1990 |
| WO | 9106319 | 5/1991 |
| WO | WO 94/29436 | 12/1994 |

OTHER PUBLICATIONS

Kozbor et al JI 136:4128–4132 1987.*
Basse et al Cancer Immunol Immunother 34:221–227 1992.*
Linsley et al J. Exp Med 174:561–569 1991.*
Ledbetter et al JI 135:2331–2336 1985.*
Martin et al JI 136:3282–3287 1986.*
Karandikar et al. J. Neuroimmunol 89:10–18 (1998).*
Bacia TIPS 14: 213–216 (1993).*
Emery et al. Exp Opin Invest. Drugs 3: 241–251 (1994).*
Kirke et al. PNAS 94: 8789–8794 (1997).*
Kotzin et al. Adv Immunol. 54: 99–166 (1993).*
Krummer et al. Intl. Immunol. 8: 519–523 (1996).*
F. Mittrucker et al. J. Exp. Med. 183: 2481–2488 (1996).*
Sahs et al. J. Exp Med 183: 2675–2680 (1996).*
Wang et al. J. Immunol. 158: 2856–2861 (1997).*
van Lier et al. Eur. J. Immunol. 18: 167–172 (1988).*
Kahan Cur. Opin. Immunol. 4:553–560, 1992.*
Yi–Qun et al. Int. Immunol. 8:37–44, 1996.*
Guinan et al. Blood 84: 3261–3282, 1994.*
Lohse et al. Springer Semin Immunopathol 14:179–186 (1992).*
Perrin et al. J. Immunol 154: 1481–1490 (1995).*
Yi et al. Chinese Medical Sciences Journal 14: 158–162 (1999).*
Swanborg Clin. Immunol. Immunopathol 77: 4–13 (1995).*
Dijkstra et al. Tips Reviews 14: 124–129 (1993).*
Perrin et al. J. Immunol 163: 1704–1710 (1999).*
Racke et al. J. Clin. Invest. 96:2195–2203 (1995).*
Zimmerman et al. Ann. Rev. Med. 52: 63–78 (2000).*
Cross et al. J. Clin. Invest. 95: 2783–2789 (1995).*
Kinck et al. Science 265: 1225–1227 (1994).*
Mihara et al. J. Clin Invest. 106: 91–101 (2000).*
Daikh et al. J. Immunol 166: 2913–2916 (2001).*
Knoerzer et al. J. Clin. Invest. 96:987–993 (1995).*
Abrams et al. J. Clin Invest. 103: 1243–1252 (1999).*
Moreland et al. Arthritis and Rheumatism 46: 1470–1479 (2002).*

(List continued on next page.)

*Primary Examiner*—Phillip Gambel
(74) *Attorney, Agent, or Firm*—Lahive & Cockfield, LLP; DeAnn F. Smith, Esq.

(57) ABSTRACT

The method of immunotherapy of the present invention involves the regulation of the T cell immune response through the activation or suppression/inactivation of the CD28 pathway. Induction of activated T cell lymphokine production occurs upon stimulatory binding of the CD28 surface receptor molecule, even in the presence of conventional immunosuppressants. Inhibition of CD28 receptor binding to an appropriate stimulatory ligand or inactivation of the CD28 signal transduction pathway through other means down-regulates CD28-pathway related T cell lymphokine production and its resulting effects.

20 Claims, 25 Drawing Sheets

OTHER PUBLICATIONS

Baroja, M.L. et al., "The Anti–T Cell Monoclonal Antibody 9.3 (Anti–CD2*) Provides a Helper Signal and Bypasses the Need for Accessory Cells in T Cell Activation with Immobilized Anti–CD3 and Mitogens," *Cell. Immunol.* 120:205–217 (1989).

Boucheix, C. et al., "Molecular Cloning of the CD9 Antigen A New Family of Cell Surface Proteins," *J. Biol. Chem.* 266:117–122 (1991).

Johnson, J.G. et al., "Monocytes Profile a Novel Costimulatory Signal to T Cells That Is Not Mediated by the CD28/B7 Interaction," *J. Immunol.* 152:429–437 (1994).

Lanza, F. et al., "cDNA Cloning and Expression of Platelet p24/CD9 Evidence for a New Family of Multiple Membrane–Spanning Proteins," *J. Biol. Chem.* 266:10638–10645 (1991).

Pierres, A. et al., "Triggering CD28 Molecules Synergize with CD2 (T 11.1 and T 11.2)–Mediated T cell Activation," *Eur. J. Immunol.* 18:685–690 (1988).

Thompson, C.B. et al., "CD28 Activation Pathway Regulates the Production of Multiple T–Cell–Derived Lymphokines/Cytokines," *PNAS (USA)* 86: 1333–1337 (1989).

Zola, H. et al., "The p24 Leucocyte Membrane Antigen: Modulation Associated With Lymphocyte Activation and Differentiation," *Immunol. Cell Biol.* 67:63–70 (1989).

P. Vandenberghe, et al., "Anti–CD28 mAb 9.3 Induces Tyrosine Phosphorylation In Human T Cells," *The FASEB Journal* 5:A991 (Abstract 3604) (1991).

Osband, M.E., et al., "Problems in the investigational study and clinical use of cancer immunotherapy" *Immunology Today* (1990) 11(6):193–195.

Dillman, R.O., "Monoclonal antibodies for treating cancer" *Annals of Internal Medicine* (1989) 111:592–603.

Hird, V., et al., "Immunotherapy with monoclonal antibodies" *Genes and Cancer,* Carney, D., et al., eds., (1990) John Wiley & Sons Ltd., New York, Chapter 17, pp. 183–189.

Van Lier, R.A.W. et al., "Signals Involved in T Cell Activation. T Cell Proliferation Induced Through the Synergistic Action of Anti–CD28 and Anti–CD2 Monoclonal Antibodies," *Eur. J. Immunol.* 18:167–172 (1988).

Tan, P. et al., "Induction of Alloantigen–Specific Hyporesponsiveness in Human T Lymphocytes by Blocking Interaction of CD28 with its Natural Ligand B7/BB1," *J. Exp. Med.* 177:165–173 (1993).

Tanaka, K. et al., "Evidence that Monoclonal Antibodies Against the 55kD Subunit of the Rat IL–2 Receptor Do Not Inhibit Mixed Lymphocyte Culture" *Transplantation* 50:125–131 (1990).

Townsend, S.E. et al., "Tumor Rejection After Direct Costimulation of CD8$^+$ T Cells by B7–Transfected Melanoma Cells," *Science* 259:368–370 (1993).

Travis, J., "A Stimulating New Approach to Cancer Treatment," *Science* 259:310–311 (1993).

Turka, L.A. et al., "T–Cell Activation by the CD28 Ligand B& is required for Cardiac Allograft Rejection in vivo," *PNAS (USA)* 89:11102–11105 (1992).

Turka, L.A. et al., "Blocking of B7–Induced T Cell Activation Prevents Cardiac Allograft Rejection," *Clin. Res.* 40:154A (1992).

Ueda, M. et al., "Cytotoxic T Cells (CTC) Activated with OKT3 and IL–2 Provide Help for IG Synthesis and Express mRNA Levels for Lymphokines and Perforin (Cyolytic Pore–Forming Protein): Implications for Immune Recovery," *J. Cell. Biochem.* Suppl 16A:188 (Abstract No. D130) (1992).

de Waal Malefyt, R. et al., "Direct Effects of IL–10 on Subsets of Human CD4$^+$ T Cell Clones and Resting T Cells. Specific Inhibition of IL–2 Production and Proliferation," *J. Immunol.* 150:4754–4765 (1993).

Ding, L. et al., "IL–10 Inhibits Macrophage Costimulatory Activity by Selectively Inhibiting the Up–Regulation of B7 Expression," *J. Immunol.* 151:1224–1234 (1993).

Engwerda, C.R. et al., "Aged T Cells are Hyporesponsive to Costimulation Mediated by CD28," *J. Immunol.* pp. 3740–3747 (1993).

Harding, F.A. et al., "CD28–B7 Interactions Allow the Induction of CD8$^+$ Cytotoxic T Lymphocytes in the Absence of Exogenous Help," *J. Exp. Med.* 177:1791 (1993).

Nunés, J. et al., "CD28 mAbs with Distinct Binding Properties Differ in their Ability to Induce T Cell Activation: Analysis of Early and Late Activation Events," *Int. Immunol.* 5:311–315 (1993).

Romano, M.F. et al., "Defect of Interleukin–2 Production and T Cell Proliferation in Atopic Patients: Restoring Ability of the CD28–Mediated Activation Pathway," *Cell. Immunol.* 148:455–463 (1993).

Shahinian, A. et al., "Differential T Cell Costimulatory Requirements in CD28–Deficient Mice," *Science* 261:609–612 (1993).

Symington, F.W. et al., "Expression and Function of B7 on Human Epidermal Langerhans Cells," *J. Immunol.* 150:1286–1295 (1993).

Capon, D.J. et al., "Designing CD4 Immunoadhesins for AIDS Therapies" *Nature* 337:525–531 (1989).

Chamow, S.M. et al., "CD4 Immunoadhesions in Anti–HIV Therapy: New Developments" *Int. J. Cancer* Suppl. 7:69–72 (1992).

Chirmule, N. et al., "HIV–gp 160–Induced T Cell–Dependent B Cell Differentiation. Role of T Cell–B Cell Activation Molecule and IL–6," *J. Immunol.* 150:2478–2486 (1993).

Costello, R. et al., "The CD2 and CD28 Adhesion Molecules Induce Long–Term Autocrine Proliferation of CD4$^+$ T Cells," *Eur. J. Immunol.* 23:608–613 (1993).

Costello, R. et al., "Activation of Primary Human T–Lymphocytes Through CD2 Plus CD28 Adhesion Molecules Induces Long–Term Nuclear Expression of NF–κ B," *Cell Growth Differ.* 4:329–339 (1993).

Costello, R. et al., "Differential Immuno–Suppressive Effects of Metabolic Inhibitors on T–Lymphocyte Activation," *Eur. Cytokine. Netw.* 4:139–146 (1993).

Damle, N.K. et al., "Proliferation of Human T Lymphocytes Induced with Superantigens is not Dependent on Costimulation by the CD28 Counter–Receptor B7," *J. Immunol.* 150:726–735 (1993).

Augustin, M. et al., "Phorbol–12–Myristate–13–Acetate–Treated Human Keratinocytes Express B7–Like Molecules that Serve a Costimulatory Role in T–Cell Activation," *J. Invest. Dermatol.* 100:275 (1993).

Baskar, S. et al., "Constitutive Expression of B7 Restores Immunogenicity of Tumor Cells Expressing Truncated Major Histocompatibility Complex Class II Molecules," *PNAS (USA)* 90:5687–5690 (1993).

Yang, S.Y. et al., "A Novel Activation Pathway for Mature Thymocytes Costimulation of CD2 (T,p50) and CD28 (T,p44) Induces Autocrine Interleukin 2/Interleukin 2 Receptor–Mediated Cell Proliferation," *J. Exp. Med.* 168:1457–1468 (1988).

Yokota, T. et al., "Isolation and Characterization of a Human Interleukin cDNA Clone, Homologous to Mouse B–cell Stimulatory Factor 1, that Expresses B–Cell– and T–Cell–2 Stimulating Activities," *PNAS (USA)* 83:5894–5898 (1986).

Young, H.A. et al., "Expression of Transfected Human Interferon–γ DNA: Evidence for Cell Specific Regulation," *J. Immunol.* 136:4700–4703 (1986).

Verwilghen, J. et al., "Differences in the Stimulating Capacity of Immobilized anti–CD3 Monoclonal Antibodies: Variable Dependence on Interleukin–1 as a Helper Signal for T–Cell Activation," *Immunology* 72:209–276 (1991).

Waldmann, T.A., "Monoclonal Antibodies in Diagnosis and Therapy," *Science* 252:1657–1662 (1991).

Wang, A.M. et al., "Molecular Cloning of the Complementary DNA for Human Tumor Necrosis Factor," *Science* 228:149–154 (1985).

Weiss, A. et al., "The Role of the T3/Antigen Receptor Complex in T–Cell Activation," *Ann. Rev. Immunol.* 4:593–619 (1986).

Weiss, A. et al., "Synergy Between the T3/Antigen Receptor Complex and Tp44 in the Activation of Human T Cells," *J. Immunol.* 137:819–825 (1986).

Wiesinger, D. et al., "Studies on the Mechanism of Action of Cyclosporin A," *Immunobiology* 156:454–464 (1979).

Wong, G.G. et al., "Human GM–CSF: Molecular Cloning of the Complementary DNA and Purification of the Natural and Recombinant Proteins," *Science* 228:810–815 (1985).

Yamada, H. et al., "Monoclonal Antibody 9.3 and Anti–CD11 Antibodies Define Reciprocal Subsets of Lymphocytes," *Eur. J. Immunol.* 15:1164–1168 (1985).

Turka, L.A. et al., "Blocking of B7–Induced T Cell Activation Prevents Cardiac Allograft Rejection," AFCR (Abstract) (1992).

Turka, L.A. et al., "In Vivo Activity of Mixed Lymphocyte Response–Generated Suppressor Cells and Ability to Prolong Cardiac Allograft Survival in Rats," *Transplantation* 47:388–390 (1989).

Turka, L.A. et al., "CD28 is an Inducible T Cell Surface Antigen that Transduces a Proliferative Signal in $CD3^+$ Mature Thymocytes," *J. Immunol.* 144:1646–1653 (1990).

Uehara, Y. et al., "Irreversible Inhibition of V–SRC Tyrosine Kinase Activity by Herbimycin A and its Abrogation by Sulfhydryl Compounds," *Biochem. Biophys. Res. Commun.* 163:803–809 (1989).

Van Lier, R.A. et al., "Signals Involved in T cell Activation. T cell Proliferation Induced Through the Synergistic Action of Anti–CD28 and Anti–CD2 Monoclonal Antibodies," *Chem. Abstracts* 108:566, #148489K (1988).

Vandenberghe, P. et al., "Antibody and B7/BB1–Mediated Ligation of the CD28 Receptor Induces Tyrosine Phosphorylation in Human T Cells," *J. Exp. Med.* 175:951–960 (1992).

Samelson, L.E. et al., "Activation of Tyrosine Phosphorylation in Human T Cells via The CD2 Pathway Regulation by the CD45 Tyrosine Phosphatase," *J. Immunol.* 145:2448–2454 (1990).

Schwartz, R.H., "Costimulation of T Lymphocytes: The Role of CD28, CTLA–4, and B7/BB1 in Interleukin–2 Production and Immunotherapy," *Cell* 71:1065–1068 (1992).

Shaw, S., "Lymphocyte Differation not all in a NAME," *Nature* 338:539–540 (1989).

Steffen, M. et al., "Simultaneous Production Of Tumor Necrosis Factor$_\alpha$ And Lymphotoxin By Normal T Cells After Induction With IL–2 And Anti–T3," *J. Immunol.* 140:2621–2624 (1988).

Tang, D. et al., "Genetic Immunization is a Simple Method for Eliciting an Immune Response," *Nature* 356:152–154 (1992).

Thompson, C.B. et al., "CD28 Activation Pathway Regulates the Production of Multiple T–Cell–Derived Lymphokines/Cytokines," *PNAS* 86:1333–1337 (1989).

Thompson, C.B. et al., "Levels of c–myc Oncogene mRNA are Invariant Throughout the Cell Cycle," *Nature,* 314:363–366 (1985).

Topelian, S.L. et al., "Expansion of Human Tumor Infiltrating Lymphocytes for Use in Immunotherapy Trials," *J. Immunol. Meth.* 102:127–141 (1987).

Perrin, P.J. et al., "Administration of Anti–CD28–Specific Monoclonal Antibody 9.3: Preclinical Studies," *Blood Suppl.,* #1747, p. 439a (Abstract) (1991).

Poggi, A. et al., "$CD3^3WT31^-$ Peripheral T Lymphocytes Lack T44 (CD28), a Surface Molecule Involved in Activation of T cells Bearing the α/β Heterodimer," *Eur. J. Immunol.* 17:1065–1068 (1987).

Pross, H.F. et al., "Spontaneous Human Lymphocyte–Mediated Cytotoxicity Against Tumor Target Cells. IX. The Quantitation of Natural Killer Cell Activity," *J. Clin. Immunol.* 1:51–63 (1981).

Punnonen, J. et al., "Interleukin 13 Induces Interleukin 4–Independent IgG4 and IgE Synthesis and CD23 Expression by Human B Cells," *PNAS (USA)* 90:3730–3734 (1993).

Reichmann, L. et al., "Reshaping Human Antibodies for Therapy," *Nature* 332:323–327 (1988).

Roitt, I.M. et al., "Cell–Mediated Immunity To Tumours—T Cell Responses," *Immunology,* p. 18.2–18.4 (1985).

Rosenberg, S.A. et al., "Gene Transfer into Humans—Immunotherapy of Patients with Advanced Melanoma, Using Tumor–Infiltrating Lymphocytes Modified by Retroviral Gene Transduction," *N. Eng. J. Med.* 323:570–578 (1990).

Martin, P.J. et al., "A 44 Kilodalton Cell Surface Homodimer Regulates Interleukin 2 Production by Activated Human T Lymphocytes," *J. Immunol.* 136:3282–3287 (1986).

Martin, P.J. et al., "Studies of T Cell Proliferation Induced by Monoclonal Antibodies of the Second International Workshop," *Leukocyte Typing II,* p. 147–156 (Reinherz, E. et al., eds., 1986).

Minty, A. et al., "Interleukin–13 is a New Human Lymphokine Regulating Inflammatory and Immune Responses," *Nature* 362:248–250 (1993).

Mishell, B.B., "Determination Of Viability by Trypan Blue Exclusion," *Selected Methods in Cellular Immunology,* p. 16–17 (1980).

Moretta, A. et al., "Involvement of T44 Molecules in an Antigen–Independent Pathway of T Cell Activation Analysis of the Correlations to the T Cell Antigen–Receptor Complex," *J. Exp. Med.* 162:823–838 (1985).

Mosmann, T.R. et al., "TH1 and TH2 Cells: Different Patterns of Lymphokine Secretion Lead to Different Functional Properties," *Ann. Rev. Immunol.* 7:145–173 (1989).

Mossmann, T.R. et al., "Two Types of Mouse Helper T–cell Clone Implications for Immune Regulation," *Immunol. Today* 8:223–227 (1987).

Newell, M.K. et al., "Death of Mature T Cells by Separate Ligation of CD4 an the T–Cell Receptor for Antigen," *Nature* 347:286–289 (1990).

Odink, K. et al., "Two Calcium–Binding Proteins in Infiltrate Macrophages of Rheumatoid Arthritis," *Nature* 330:80–82 (1987).

Lindsten, T. et al., "Regulation of 4F2 Heavy–Chain Gene Expression During Normal Human T–Cell Activation can be Mediated by Multiple Distinct Molecular Mechanisms," *Mol. Cell. Biol.* 8:3820–3826 (1988).

Lindsten, T. et al., "A Novel T Cell Activation Pathway Regulates the mRNA Stability of Lymphokines Sharing a Conserved AU Sequence," *Science* 244:339–343 (1989).

Linsley, P.S. et al., "Binding of the B Cell Activation Antigen B7 to CD28 Costimulates T Cell Proliferation and Interleukin 2 mRNA Accumulation," *J. Exp. Med.* 173:721–730 (1991).

Linsley, P.S. et al., "CTLA–4 is a Second Receptor for the B Cell Activation Antigen B7," *J. Exp. Med.* 174:561–569 (1991).

Lum, L.G. et al., "mRNA Levels For IL–2 Receptors (IL–2R), IL–2, and IL–3 Determined by Reverse Transcriptase–Polymerase Chain Reaction (RTase–PCR) are Detectable in Lymphocytes (PBL) from Short and Long–Term BMT Recipients," *Blood Suppl.* #901, p. 2281 (Abstract) (1991).

Makni, H. et al., "Reconstitution of an Active Surface CD2 by DNA Transfer in $CD2^-CD3^+$ Jurkat Cells Facilitates CD3–T Cell Receptor–Mediated IL–2 Production," *J. Immunol.* 146:2522–2529 (1991).

Marrack, P. et al., "The T–cell Repertoire for Antigen and MHC," *Immunol. Today* 9:308–315 (1988).

Ledbetter, J.A. et al., "Crosslinking of Surface Antigens Causes Mobilization of Intracellular Ionized Calcium in T Lymphocytes," *PNAS (USA)* 84:1384–1388 (1987).

Ledbetter, J.A. et al., "Practical Aspects of Two–Color Cytofluorimetry Using a Single Argon Laser," *Lymphocyte Surface Antigens*, p. 119–129 (E. Heise ed., 1984).

Lee, K.P. et al., "The Genomic Organization of the CD28 Gene Implications for the Regulation of CD28 mRNA Expression and Heterogeneity," *J. Immunol.* 145:344–352 (1990).

Lee, K.P. et al., "The CD28 Signal Transduction Pathway in T Cell Activation," In "Advances of Regulation of Cell Growth," vol. 2; *Cell Activation: Genetic Approaches*, p. 141–159 (J.J. Mond et al., eds. 1991).

Lin, H., "CTLA–4Ig is a Potent Immunosuppressive Agent in Heart Transplantation in Rats," (submitted for publication).

Lindsten, T. et al., "Stimulation Of The Antigen Receptor Complex Leads to Transcriptional Activation Of The c–MYC Gene in Normal Human T Cells," *Curr. Topics Microbiol. Immunol.* 141:223–230 (1988).

Lindsten, T. et al., "Multiple Mechanisms Regulate c–myc Gene Expression During Normal T Cell Activation," *EMBO J.* 7:2787–2794 (1988).

Kunkel et al., "Prostaglandin $E_2$ Regulates Macrophage–Derived Tumor Necrosis Factor Gene Expression," *J. Biol. Chem.* 263:5380–5384 (1988).

Lagasse, E. et al., "Cloning and Expression of Two Human Genes Encoding Calcium–Binding Proteins that are Regulated During Myeloid Differentiation," *Mol. Cell. Biol.* 8:2402–2410 (1988).

Lane, H.C. et al., "Qualitative Analysis of Immune Function in Patients with the Acquired Immunodeficiency Syndrome," *N. Engl. J. Med.* 313:79–84 (1985).

Lange, B. et al., "Growth Factor Requirements of Childhood Acute Leukemia: Establishment of GM–CSF–Dependent Cell Lines," *Blood* 70:192–199 (1987).

Lea, T. et al., "Magnetic Monosized Polymer Particles for Fast and Specific Fractionation of Human Mononuclear Cells," *Scan. J. Immunol.* 22:207–216 (1985).

Ledbetter, J.A. et al., "CD28 Ligation in T–Cell Activation: Evidence for Two Signal Transduction Pathways," *Blood* 75:1531–1539 (1990).

Ledbetter, J.A. et al., "Antibody Binding To CD5 (Tp67) And Tp44 T Cell Surface Molecules: Effects On Cyclic Nucleotides, Cytoplasmic Free Calcium, and cAMP–Mediated Suppression," *J. Immunol.* 137:3299–3305 (1986).

Ledbetter, J.A. et al., "Antibodies to Tp67 and Tp44 Augment and Sustain Proliferative Responses Of Activated T Cells," *J. Immunol.* 135:2331–2336 (1985).

June, C.H. et al., "Increases in Tyrosine Phosphorylation are Detectable Before Phospholipase C Activation After T Cell Receptor Stimulation," *J. Immunol.* 144:1591–1599 (1990).

June, C.H. et al., "Evidence for the Involvement of Three Distinct Signals in the Induction of IL–2 Gene Expression in Human T Lymphocytes," *J. Immunol.* 143:153–161 (1989).

June, C.H. et al., "Two Distinct Mechanisms of Interleukin 2 Gene Expression in Human T Lymphocytes," *J. Autoimmunity* 2 (suppl.):55–65 (1989).

June, C.H. et al., "Distinct Patterns of Transmembrane Calcium Flux and Intracellular Calcium Mobilization After Differentiation Antigen Cluster 2 (E Rosette Receptor) or 3 (T3) Stimulation of Human Lymphocytes," *J. Clin. Invest.* 77:1224–1232 (1986).

Katsanis, E. et al., "Proliferation and Cytolytic Function of Anti–CD3 + Interleukin–2 Stimulated Peripheral Blood Mononuclear Cells Following Bone Marrow Transplantation," *Blood* 78:1286–1291 (1991).

Koulova, L. et al., "The CD28 Ligand B7/BB1 Provides Costimulatory Signal for Alloactivation of $CD4^+$ T Cells," *J. Exp. Med.* 173:759–762 (1991).

Kozbor, D. et al., "Tp44 Molecules Involved in Antigen–Independent T Cell Activation are Expressed on Human Plasma Cells," *J. Immunol.* 138:4128–4132 (1987).

Herrmann, T. et al., "Different Staphylococcal Enterotoxins Bind Preferentially to Distinct Major Histocompatibility Complex Class II Isotypes," *Eur. J. Immunol.* 19:2171–2174 (1989).

Hsi, E.D. et al., "T Cell Activation Induces Rapid Tyrosine Phosphorylation of a Limited Number of Cellular Substrates," *J. Biol. Chem.* 264:10836–10842 (1989).

Jenkins, M.K. et al., "CD28 Delivers a Costimulatory Signal Involved in Antigen–Specific IL–2 Production by Human T Cells," *J. Immunol.* 147:2461–2466 (1991).

Joshi, I. et al., "Defects in Anti–CD3–Induced Proliferative Responses in Lymphocytes (PBL) from BMT Patients Can be Repaired by Adding 9.3 (Anti–CD28)," *Blood Suppl.* #906 (Abstract) (1991).

Julius, M.H. et al., "A Rapid Method for the Isolation of Functional Thymus–derived Murine Lymphocytes," *Eur. J. Immunol.* 3:645–649 (1973).

June, C.H. et al., "Inhibition of Tyrosine Phosphorylation Prevents T–Cell Receptor–Mediated Signal Transduction," *PNAS (USA)* 87:7722–7726 (1990).

June, C.H. et al., "Role of the CD28 Receptor in T–Cell Activation," *Immunol. Today* 11:211–216 (1990).

June, C.H. et al., "T–Cell Proliferation Involving the CD28 Pathway is Associated with Cyclosporine–Resistant Interleukin 2 Gene Expression," *Mol. Cell. Biol.* 7:4472–4481 (1987).

Green, J.M. et al., "CD28 And Staphylococcal Enterotoxins Synergize To Induce MHC–Independent T–Cell Proliferation," *Cell. Immunol.*, 145:11–20 (1992).

Groux, H. et al., "Activation–Induced Death by Apoptosis in $CD4^+$ T Cells from Human Immunodeficiency Virus–infected Asymptomatic Individuals," *J. Exp. Med.* 175:331–340 (1992).

Guba, S.C. et al., "Regulation of Interleukin 3 Gene Induction in Normal Human T Cells," *J. Clin. Invest.* 84:1701–1706 (1989).

Hansen, J.A. et al., "Monoclonal Antibodies Identifying a Novel T–Cell Antigen and Ia Antigens of Human Lymphocytes," *Immunogenetics* 10:247–260 (1980).

Hara, T. et al., "Human T Cell Activation II. A New Activation Pathway Used by a Major T Cell Population Via a Disulfide–bonded Dimer of a 44 Kilodalton Polypeptide (9.3 Antigen)," *J. Exp. Med.* 161:1513–1524 (1985).

Hardy, R., "Purification and Characterization of Monoclonal Antibodies," *Handbook of Experimental Immunology*, p. 13.1–13.13 (1986).

Harris, W. et al., "Therapeutic Antibodies—the Coming of Age," *TIBTECH* 11:42–44 (1993).

Herman, A. et al., "HLA–DR Alleles Differ in Their Ability to Present Staphylococcal Enterotoxins to T Cells," *J. Exp. Med.* 177:1791 (1993).

Fraser, J.D. et al., "Regulation of Interleukin–2 Gene Enhancer Activity by the T Cell Accessory Molecule CD28," *Science* 251:313–316 (1991).

Freedman, A.S. et al., "B7, a B Cell–Restricted Antigen that Identifies Preactivated B Cells," *J. Immunol.* 139:3260–3267 (1987).

Freeman, G.J. et al., "B7, a New Member of the Ig Superfamily with Unique Expression on Activated and Neoplastic B Cells," *J. Immunol.* 143:2714–2722 (1989).

Gascoigne, N.R. et al., "Secretion of a Chimeric T–Cell Receptor–Immunoglobulin Protein," *PNAS (USA)* 84:2936–2940 (1987).

Geppert, T.D. et al., "Accessory Cell Independent Proliferation of Human T4 Cells Stimulated by Immobilized Monoclonal Antibodies to CD3," *J. Immunol.* 138:1660–1666 (1987).

Gillis, S. et al., "Long Term Culture of Tumour–Specific Cytotoxic T Cells," *Nature* 268:154–156 (1977).

Gimmi, C.D. et al., "B–Cell Surface Antigen B7 Provides a Costimulatory Signal that Induces T cells to Proliferate and Secrete Interleukin 2," *PNAS (USA)* 88:6575–6579 (1991).

Goding, J.W., "The Avidin–Biotin System," *Monoclonal Antibodies Principles and Practice*, p. 230 (J.W. Goding, ed. 1983).

Damle, N.K. et al., "Differential Regulatory Signals Delivered by Antibody Binding to the CD28 (Tp44) Molecule During the Activation of Human T Lymphocytes," *J. Immunol.* 140:1753–1761 (1988).

Dariavach, P. et al., "Human Ig Superfamily CTLA–4 Gene: Chromosomal Localization and Identity of Protein Sequence Between Murine and Human CTLA–4 Cytoplasmic Domains," *Eur. J. Immunol.* 18:1901–1905 (1988).

Darzynkiewicz, Z., "Differential Staining of DNA and RNA in Intact Cells and Isolated Cell Nuclei with Acridine Orange," *Meth. Cell. Biol.* 33:285–298 (1990).

DeFranco, A.L., "Between B Cells and T Cells," *Nature* 351:603–604 (1991).

Dorin, J.R. et al., "A Clue to the Basic Defect in Cystic Fibrosis from Cloning the CF Antigen Gene," *Nature* 326:614–617 (1987).

Fell, H.P. et al., "Chimeric L6 Anti–Tumor Antibody," *J. Biol. Chem.* 267:15552–15558 (1992).

Fleischer, B. et al., "T Cell Stimulation by Staphylococcal Enterotoxins Clonally Variable Response and Requirement for Major Histocompatibility Complex Class II Molecules on Accessory or Target Cells," *J. Exp. Med.* 167:1697–1707 (1988).

Bolling, S.F. et al., "Inhibition Of B7–Induced CD28 T Cell Activation with CTLA–4 Prevents Cardiac Allograft Rejection; Evidence for Co–Stimulation," *Am. Coll. Surgeon* (Abstract) (1992). Surgical Forum 43:pp 413–415 (1992).

Bolling, S.F. et al., "Prolongation of Cardiac Allograft Survival in Rats by Anti–TNF and Cyclosporine Combination Therapy," *Transplantation* 53:283–286 (1992).

Cantrell, D.A. et al., "Transient Expression of Interleukin 2 Receptors Consequences for T Cell Growth," *J. Exp. Med.* 158:1895–1911 (1993).

Carlsson, R. et al., "Binding of Staphylococcal Enterotoxin a to Accessory Cells is a Requirement for its Ability to Activate Human T Cells," *J. Immunol.* 140:2484–2488 (1988).

Chintagumpala, M.M. et al., "Staphylococcal Toxins Bind to Different Sites on HLA–DR," *J. Immunol.* 147:3876–3881 (1991).

Clark, E.A. et al., "Role of the Bp35 Cell Surface Polypeptide in Human B–cell Activation," *PNAS (USA)* 82:1766–1770 (1985).

Damle, N.K. et al., "Differential Regulatory Signals Delivered by Antibody Binding to the CD28 (Tp44) Molecule During the Activation of Human T Lymphocytes," *Chem. Abstracts* 108:499, #16579IV (1988).

Ameisen, J.C. et al., "Cell Dysfunction and Depletion in AIDS: the Programmed Cell Death Hypothesis," *Immunol. Today* 12:102–105 (1991).

Aruffo, A. et al., "Molecular Cloning of a CD28 cDNA by a High–Efficiency COS Cell Expression System," *PNAS (USA)* 84:8573–8577 (1987).

Azuma, M. et al., "CD28 Interaction with B7 Costimulates Primary Allogeneic Proliferative Responses and Cytotoxicity Mediated by Small, Resting T Lymphocytes," *J. Exp. Med.* 175:353–360 (1992).

Bernstein, I.D. et al., "Joint Report of the Myeloid Section of the Second International Workshop on Human Leukocyte Differentiation Antigens," *Leukocyte Typing II*, 1–25 (E. Reinherz, et al., eds., 1986).

Bohlen, B. et al., "Lysis of Malignant B Cells From Patients with B–Chronic Lymphocytic Leukemia by Autologous T Cells Activated with CD3 X CD19 Bispecific Antibodies in Combination with Bivalent CD28 Antibodies," *Blood* 82:1803–1812 (1993).

\* cited by examiner

T$_H$1 Lymphokine mRNA Expression in the Presence of Cyclosporine

METHODS OF TREATING AUTOIMMUNE DISEASE VIA CTLA-4IG

RELATED APPLICATIONS

This application is a continuation of U.S. Ser. No. 08/076,071, filed Jun. 10, 1993, now abandoned, which is a continuation-in-part of PCT/US93/03155, filed Apr. 6, 1993, which is a continuation of U.S. Ser. Nos. 07/864,805, 07/864,807, 07/864,866, all filed Apr. 7, 1992, and all abandoned, which are all continuation-in-parts of Ser. No. 07/275,433, filed Nov. 23, 1988, now abandoned, all of which are hereby incorporated by reference.

SPONSORSHIP

Work on this invention was supported in part by Naval Medical Research and Development Command, Research Task No. M0095.0003-1007. The Government has certain rights in the invention.

BIOLOGICAL DEPOSIT

Murine hybridoma cell line 9.3 has been deposited with the American Type Culture Collection in Rockville, Md., in compliance with the provisions of the Budapest Treaty, and has been assigned ATCC Designation No. HB10271.

FIELD OF THE INVENTION

The present invention generally relates to immunotherapy. More particularly, the present invention relates to immunotherapy involving regulation of the CD28 T cell surface molecule.

BACKGROUND OF THE INVENTION

Thymus derived lymphocytes, referred to as T cells, are important regulators of in vivo immune responses. T cells are involved in cytotoxicity and delayed type hypersensitivity (DTH), and provide helper functions for B lymphocyte antibody production. In addition, T cells produce a variety of lymphokines which function as immunomodulatory molecules, such as for example, interleukin-2 (IL-2), which can facilitate the cell cycle progression of T cells; tumor necrosis factor-$\alpha$ (TNF-$\alpha$) and lymphotoxin (LT), cytokines shown to be involved in the lysis of tumor cells; interferon-$\gamma$ (IFN-$\gamma$), which displays a wide variety of anti-viral and anti-tumor effects; and IL-3 and granulocyte-macrophage colony stimulating factor (GM-CSF), which function as multilineage hematopoietic factors.

Current immunotherapeutic treatments for diseases such as cancer, acquired immunodeficiency syndrome (AIDS) and attending infections, involve the systemic administration of lymphokines, such as IL-2 and IFN-$\gamma$, in an attempt to enhance the immune response. However, such treatment results in non-specific augmentation of the T cell-mediated immune response, since the lymphokines administered are not specifically directed against activated T cells proximate to the site of infection or the tumor. In addition, systemic infusions of these molecules in pharmacologic doses leads to significant toxicity. Present therapies for immunodeficient or immunodepressed patients also involve non-specific augmentation of the immune system using concentrated $\gamma$-globulin preparations. The stimulation of the in vivo secretion of immunomodulatory factors has not, until now, been considered a feasible alternative due to the failure to appreciate the effects and/or mechanism and attending benefits of such therapy.

It would thus be desirable to provide a method of immunotherapy which enhances the T cell-mediated immune response and which is directed specifically toward T cells activated by an antigen produced by the targeted cell. It would further be desirable to provide a method of immunotherapy which could take advantage of the patient's natural immunospecificity. It would also be desirable to provide a method of immunotherapy which can be used in immunodepressed patients. It would additionally be desirable to provide a method of immunotherapy which does not primarily rely on the administration of immunomodulatory molecules in amounts having significant toxic effects.

It would also be desirable to provide a method of immunotherapy which, if so desired, could be administered directly without removal and reintroduction of T cell populations. It would further be desirable to provide a method of immunotherapy which could be used not only to enhance, but to suppress T cell-mediated immunoresponses where such immunosuppression would be advantageous, for example, in transplant patients, in patients exhibiting shock syndrome and in certain forms of autoimmune disease.

SUMMARY OF THE INVENTION

The present invention comprises a method of immunotherapy in which the T cell-mediated immune response is regulated by the CD28 pathway. Binding of the CD28 receptor with anti-CD28 antibodies or other stimulatory binding equivalents induces activated T cell-mediated lymphokine production. Immunosuppression or down-regulation is achieved by preventing CD28 receptor binding to stimulatory ligands or inactivation of the CD28 signal transduction pathway.

The method of immunotherapy of the present invention takes advantage of the surprising and heretofore unappreciated effects of stimulation of the CD28 surface receptor molecule of activated T cells. By activated T cells is meant cells in which the immune response has been initiated or "activated," generally but not necessarily by the interaction of the T cell receptor (TCR)/CD3 T cell surface complex with a foreign antigen or its equivalent. While such activation results in T cell proliferation, it results in only limited induction of T cell effector functions such as lymphokine production.

Stimulation of the CD28 cell surface molecule with anti-CD28 antibody results in a marked increase of T cell lymphokine production. Surprisingly, even when the stimulation of the TCR/CD3 complex is maximized, upon costimulation with anti-CD28, there is a substantial increase in the levels of IL-2 lymphokine, although there is no significant increase in T cell proliferation over that induced by anti-TCR/CD3 alone. Even more surprisingly, not only are IL-2 levels significantly increased, but the levels of an entire set of lymphokines, hereinafter referred to as $T_H$CD28 lymphokines, previously not associated with CD28 stimulation are increased. Remarkably both the T cell proliferation and increased lymphokine production attributable to CD28 stimulation also exhibit resistance to immunosuppression by cyclosporine and glucocorticoids.

The method of immunotherapy of the present invention thus provides a method by which the T cell-mediated immune response can be regulated by stimulating the CD28 T cell surface molecule to aid the body in ridding itself of infection or cancer. The method of the present invention can also be used not only to increase T cell proliferation, if so desired, but to augment or boost the immune response by increasing the levels and production of an entire set of T cell lymphokines now known to be regulated by CD28 stimulation.

Moreover, because the effectiveness of CD28 stimulation in enhancing the T cell immune response appears to require T cell activation or some form of stimulation of the TCR/CD3 complex, the method of immunotherapy of the present invention can be used to selectively stimulate T cells pre-activated by disease or treatment to protect the body against a particular infection or cancer, thereby avoiding the non-specific toxicities of the methods presently used to augment immune function. In addition, the method of immunotherapy of the present invention enhances T cell-mediated immune functions even under immunosuppressed conditions, thus being of particular benefit to individuals suffering from immunodeficiencies such as AIDS.

It will also be appreciated that although the following discussion of the principles of the present invention exemplifies the present invention in terms of human therapy, the methods described herein are similarly useful in veterinary applications.

A better understanding of the present invention and its advantages will be had from a reading of the detailed description of the preferred embodiments taken in conjunction with the drawings and specific examples set forth below.

DETAILED DESCRIPTION OF THE PREFERRED EMBODIMENTS

Figure 1:
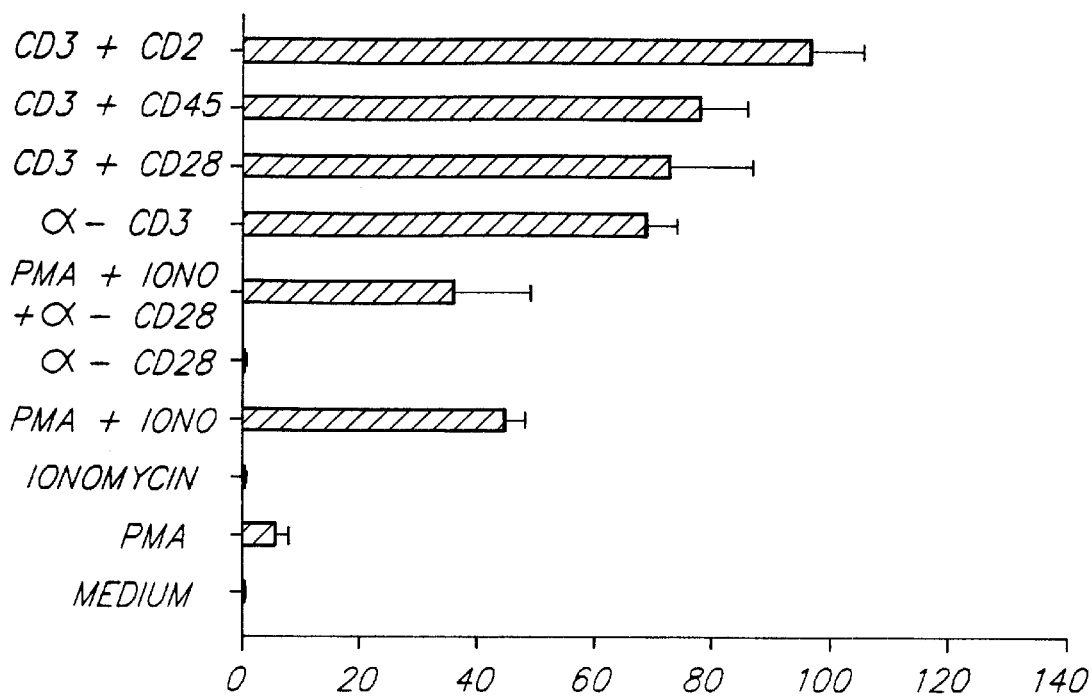
FIG. 1 is a bar graph illustrating the absence of augmentation of the uptake of thymidine by CD28 stimulated T cells.

In one preferred embodiment of the immunotherapeutic method of the present invention, the CD28 molecule is stimulated to enhance the T cell-mediated immune response of antigen or otherwise activated T cells. CD28 is a 44 kilodalton protein expressed on the surface of about 80% mature T cells which exhibits substantial homology to immunoglobulin genes. See Poggi, A. et al., *Eur. J. Immunol.*, 17:1065–1068 (1987) and Aruffo, A. et al., *PNAS (USA)*, 84:8573–8577 (1987), both herein incorporated by reference. Binding of the CD28 molecule's extracellular domain with anti-CD28 antibodies in accordance with the method of the present invention results in an increase in T cell proliferation and elevated lymphokine levels.

In Specific Examples III–IV and VI–VIII, T cell activation was accomplished by stimulating the T cell TCR/CD3 complex (which mediates the specificity of the T cell immune response) with immobilized anti-CD3 monoclonal antibodies, such as mAb G19–4, or by chemically stimulating with PMA and ionomycin. It should also be appreciated, however, that activation of the T cell can instead be accomplished by routes that do not directly involve CD3 stimulation, such as the stimulation of the CD2 surface protein.

In practice, however, an activated T cell population will be provided by the patient's own immune system, which, barring total immunosuppression, will have T cells activated in response to any foreign or substantially elevated level of antigen present due to disease, infection, inoculation or autoimmunity. The term "Foreign antigen" is used broadly herein, meaning an antigen which is either not normally produced by the organism, or, as in carcinomas, an antigen which is not normally produced by the cell which is producing it. The term is also meant to include an antigen which should normally be seen as "self," but, as occurs in autoimmune disease states, provokes an immune response as would a foreign antigen. By "substantially elevated" level of antigen is meant an antigen level exceeding normal ranges and having potentially deleterious effects to the organism due to such elevation.

In accordance with the method of the present invention, stimulation of the CD28 molecule itself is achieved by administration of a ligand, such as a monoclonal antibody or a portion thereof, (e.g. F(ab')$_2$), having a binding specificity for and stimulatory effect on CD28. Suitable antibodies include mAb 9.3, an lgG2a antibody on deposit with the ATCC which has been widely distributed and is available (for non-commercial purposes) upon request from Dr. Jeffrey A. Ledbetter of Oncogen Corporation, Seattle, WA, or Mab Kolt-2. Both these monoclonal antibodies have been shown to have binding specificity for the extracellular domain of CD28 as described in "Leukocyte Typing II," Ch. 12, pgs. 147–156, ed. Reinherz, E. L. et al. (1986). Monoclonal antibody 9.3 F(ab')$_2$ has also been shown to be a satisfactory ligand capable of stimulating the CD28 receptor. It should also be understood that the method of the present invention contemplates the use of chimaeric antibodies as well as non-immunoglobulin, natural and recombinant ligands which bind the CD28 surface molecule. More recently, the natural ligand for CD28, B7/BB1, has also been identified and can be used in accordance with the principles of the present invention. See Linsley, P. S. et al., *J. Exp. Med.* 174:561 (1991). In addition, binding homologs of a natural ligand, whether natural or synthesized by biochemical, immunological, recombinant or other techniques, can also be used in accordance with the principles of the present invention. It will be appreciated that the ligands referred to herein can be utilized in their soluble or cell-bound forms, depending on their application. Monoclonal antibody 9.3 and B7 are currently preferred stimulatory ligands.

The extracellular domain of CD28, which was sequenced by Aruffo, A. et al., *PNAS (USA)*, 84:8573–8577 (1987), generally comprises the following amino acid sequence:

MetLeuArgLeuLeuLeuAlaLeuAsnLeuPheProSerIleGln
ValThrGlyAsnLysIleLeuValLysGlnSerProMetLeuVal
AlaTyrAspAsnAlaValAsn LeuSerCysLysTyrSer-
TyrAsn LeuPheSerArgGluPheArgAlaSer-
LeuHisLysGlyLeuAsp SerAlaValGluValCysValVal-
TyrGlyAsnTyrSerGlnGln LeuGlnValTyrSer-
LysThrGlyPheAsnCysAspGlyLysLeu GlyAsnGluSer-
ValThrPheTyrLeuGlnAsnLeuTyrValAsn GlnThrAspi-
leTyrPheCysLysIleGluvalMetTyrProPro ProTyr-
LeuAspAsnGluLysSerAsnGlyThrIleIleHisVal
LysGlyLysHisLeuCysProSerProLeuPheProGlyProSer
LysPro By the term "extracellular domain" as used hereinafter in the specification and claims, is meant the amino acid sequence set forth above, any substantial portion thereof, or any sequence having substantial homology thereto.

As shown by the data of Specific Examples III–V, substantial augmentation of the T cell-mediated immunoresponse by CD28 stimulation appears specific for activated T cells. Such specificity is of particular clinical importance and is one of the significant advantages of the method of immunotherapy of the present invention. Administration of anti-CD28 antibodies or other CD28 ligands will specifically augment the response of T cells which are already activated and engaged in the immune response or those in the process of activation. It should, however, also be appreciated that CD28 stimulation may be effective even where the T cells are activated after the binding of the CD28-specific ligand of the present invention to CD28 receptor. Thus, the T cells at or near the tumor site or site of infection, which are being activated by the antigens produced or present at those sites, will be selectively "boosted" by the CD28 stimulation.

Boosting of the immune response can also be beneficial to healthy individuals, for example, in augmenting their response to antigens presented in vaccines (see Specific Example IX). CD28 stimulation coupled with antigen administration in accordance with the present invention can result in more effective immunization, not only with conventional vaccines, but in situations where an adequate immune response is difficult to elicit, e.g. with human retroviruses such as HIV and some herpes viruses. Examples where CD28 stimulation of the present invention can be used to augment the immune response include, but are not limited to viral vaccines against measles, influenza, polio, herpes viruses (i.e. HCMV, Epstein Barr Virus, Herpes Simplex Type I and II ); bacterial vaccines against whooping cough (*Bordatella pertussis*), tetanus (*Clostridium tetanus*), pneumonia (*Streptococcus pneumoniae*), meningitis and gonorrhea (Neisseria) and against enteropathic bacteria such as Salmonella, E. coil and Shigella. The principles of the present invention are also applicable in inoculations against parasitic infection, including those caused by protozoal parasites, e.g. malaria, trypanosomiasis, leishmaniasis, amebiasis, toxoplasmosis, pneumocystis carinni and babesiosis, by cestodes (e.g. tapeworm) and by other parasitic organisms. It will also be appreciated that immunization for a humoral response through injection of cDNA for intracellular antigenic production, as described in *Nature* 356:152 (1992), costimulated with anti-CD28 is also contemplated as within the scope of the present invention.

Indeed, recently CD28 engagement and signal transduction have been used to identify IL-13 (Minty, A. et al., *Nature* 362: (6417):248–50 (1993)), a lymphokine involved in the inflammatory and immune response. Punnonev, J. et al., *PNAS (USA)* 90(8): 3730–4 (1993). When TCR/CD3 stimulation is maximized, although T cell proliferation is not markedly increased, the levels of certain lymphokines are substantially increased by CD28 activation, indicating an increase in cellular production of these lymphokines. Thus, in patients undergoing natural maximal TCR/CD3 stimulation or its equivalent T cell activation in vivo due to disease or infection, the administration of anti-CD28 antibody or other CD28 ligand to stimulate CD28 in accordance with the method of the present invention will result in substantially elevated lymphokine production.

The increase in lymphokine production achieved by administration of a CD28 stimulator in accordance with the method of the present invention, as particularly shown in Specific Example III, surprisingly results in the increased production of an entire set of lymphokines, indicating that these lymphokines are under some form of CD28 regulation. Part of this set of lymphokines, which includes IL-2, TNF-α, LT, IFN-γ, and IL-3 as later determined, is somewhat analogous to the $T_H1$ cell lymphokines present in the mouse which were described by Mosmann, T. R. et al., ImmunoL. Today, 8:223–227 (1987). Although it was originally believed that human IL-4 production was not increased by CD28 stimulation, more recent assays as set forth in Specific Example III have now also shown an increase in the production of other lymphokines, including IL-4 and IL-5 and the increased production of IL-6 and IL-1 was also confirmed in Specific Example IX. It will be appreciated, however, that the term "$T_H1$ lymphokines" was originally used for ease of reference and was expressly not limited to the lymphokines listed above, but was meant to include all lymphokines whose production is affected or regulated by the binding or stimulation of the CD28 T cell surface molecule. Thus the group of lymphokines affected by CD28 will hereinafter be referred to as $T_H$CD28 lymphokines, it will again be appreciated that the term $T_H$CD28 lymphokine is not intended to be limiting to the specific lymphokines listed herein. Furthermore, it will be appreciated that the principles of the present invention can be used in veterinary applications to increase the T cell-mediated immune response and lymphokine production in animals. The term $T_H$CD28 lymphokines, as used herein, is thus also meant to include analogous animal lymphokines. Thus, by administration of anti-CD28 antibodies or other CD28 ligands in accordance with the method of the present invention, the production and levels of an entire set of lymphokines can be significantly increased.

The method of immunotherapy of the present invention can also be used to facilitate the T cell-mediated immune response in immunodepressed patients, such as those suffering from AIDS. As shown in Specific Examples VI–VII, T cell proliferation and the increased levels or production of CD28-regulated lymphokines continue to function even in the presence of immunosuppression such as that caused by cyclosporine or dexamethasone. Thus administration of CD28 stimulators such as mAb 9.3 or other CD28 ligands can be used to treat immunodepressed patients to increase their in vivo lymphokine levels.

In addition, a variety of syndromes including septic shock and tumor-induced cachexia may involve activation of the CD28 pathway and augmented production of potentially toxic levels of lymphokines. The immune response can also be deleterious in other situations such as in organ transplant recipients or in autoimmune disease. Thus down-regulation or inactivation of the CD28 pathway, as discussed more fully below and in Specific Examples X and XI, can also provide immunotherapy for those and other clinical conditions.

It should be appreciated that administration of an anti-CD28 antibody has not heretofore been seriously contemplated as a potential immunotherapeutic method for the substantial increase of lymphokine levels at the sites of activated T cells. For example, the addition of mAb 9.3 has been thought only to somewhat augment T cell proliferation, not to induce substantial increases in $T_H$CD28 lymphokine production.

Although it is not the intent herein to be bound by any particular mechanism by which CD28 binding regulates the T cell-mediated immune response, a model for the mechanism of stimulation has been postulated and supported with experimental data, some of which is shown in Specific Example VIII. It has previously been shown that a number of lymphokine genes undergo more rapid degradation in the cytoplasm than mRNAs from constitutively expressed housekeeping genes, leading to the hypothesis that the instability of these inducible mRNAs has been selected to allow for rapid regulation of gene expression. It is believed that the mechanism of CD28 regulation herein described and claimed is related to the stabilization of rapidly degradable mRNAs for the set of $T_H$CD28 lymphokines set forth above. To date, it ppears no other mechanism in any eukaryotic cell system has been described to emonstrate that a cell surface activation pathway can alter gene expression by inducing specific alteration in mRNA degradation. (A more in-depth analysis of possible models of CD28 activation is presented later herein.)

As shown in Specific Example IV, costimulation of CD28 and TCR/CD3 caused an increase in mRNA of the THCD28 lymphokines which was not the result of a generalized increase in a steady state mRNA expression of all T cell activation-associated genes. The increase was disproportionate and thus could not be accounted for by the increase in percentage of proliferating cells in culture. These data, in addition to further studies not detailed herein, demonstrate that activation of the CD28 surface molecule of activated T cells functions to specifically stabilize lymphokine mRNAs. Increased mRNA stability, i.e. slower degradation thereof, results in increased translation of the mRNA, in turn resulting in increased lymphokine production per cell. An increase in per T cell production of lymphokines that allows the T cell to influence the response of other inflammatory and hematopoietic cells is referred to as paracrine production. In contrast, an increase in lymphokine levels merely due to increased cell proliferation, such as that shown in Martin, P. J. et al., *J. Immunol.* 136:3282–3287 (1986), is commonly referred to as autocrine production. For ease of reference, paracrine production is also herein referred to as ."cellular" production of lymphokines.

Thus, in accordance with the principles of the present invention, ligands with binding specificity for the CD28 molecule are administered in a biologically compatible form suitable for administration in vivo to stimulate the CD28 pathway. By "stimulation of the CD28 pathway" is meant the stimulation of the CD28 molecule resulting in increased T cell production of $T_H$CD28 lymphokines. By "biologically compatible form suitable for administration in vivo" is meant a form of the ligand to be administered in which the toxic effects, if any, are outweighed by the therapeutic effects of the ligand. Administration of the CD28 ligand can be in any suitable pharmacological form, including but not limited to intravenous injection of the ligand in solution.

It should be understood that, although the models for CD28 regulation of lymphokine production are described with respect to stimulation and enhancement of lymphokine levels, as noted above, down-regulation or inhibition of the CD28 pathway is also in accordance with the principles of the present invention. Down-regulation or suppression of the immune response is of particular clinical interest for a variety of conditions, including septic shock, tumor-induced cachexia, autoimmune diseases and for patients receiving heart, lung, kidney, pancreas, liver and other organ transplants. One preferred approach to down-regulation is the blocking of the CD28 receptor stimulatory binding site on its natural ligand. For example, CTLA-4 (discussed in more detail below), which shares 32% amino acid homology with CD28 and appears to have greater binding affinity for B7 than CD28, can be used to bind B7 and prevent CD28 binding and activation thereby. See Linsley, P. S. et al., *J. Exp. Med.*, 174:561 (1991). Such regulation has been accomplished in vivo as described in Specific Example X. In this Example, acute rejection of fully MHC-mismatched cardiac allografts was prevented by blocking B7-dependent T cell activation, i.e. CD28 binding, with the soluble recombinant fusion protein CTLA-4Ig. The immunosuppression observed with CTLA-4Ig did not result in significant alterations in circulating T cell subsets. It will be appreciated that other B7-binding ligands such as a monoclonal antibody to B7 can be similarly employed. In addition, CTLA-4Ig treatment can be efficacious in the treatment of autoimmune diseases, as shown in the murine model for multiple sclerosis (i.e. Experimental Autoimmune Encephalomyelitis (EAE)). CTLA-4Ig treatment of T cells isolated from a mouse immunized with Myelin Basic Protein (MBP) results in reduced disease severity when the treated cells are introduced into a syngeneic animal. Likewise, when mice immunized with MBP and injected with pertussis toxin (PT) are treated directly with CTLA-4Ig, disease severity is reduced. These findings confirm the in vivo immunosuppressive effects of CTLA-4Ig treatment. Thus, administration of CTLA-4 can provide an effective therapeutic strategy for the treatment of autoimmune diseases. Those skilled in the art will also appreciate that the cell lines and animal models used to exemplify the present invention are recognized predictors of efficacy in humans.

It will be appreciated that down-regulation can also be accomplished by blocking CD28 receptor binding to B7 by occupying the CD28 binding site with nonstimulatory ligands which may mimic stimulatory ligands but do not result in activation of the CD28 pathway, e.g. Fabs, modified natural, synthetic, recombinant or other ligands which do not crosslink or otherwise do not activate receptors.

As discussed above and shown in the Specific Examples, the blockade of stimulatory ligands which bind to CD28 and activate the CD28 pathway (e.g. B7) or the blocking of the CD28 binding site can reduce the increased lymphokine expression which occurs upon CD28 activation. Thus, just as manipulation of the CD28 pathway can be used to enhance T cell immune responses, it can also be used to suppress such responses. Since unregulated lymphokine production has been implicated in the aetiology of autoimmunity, CD28-mediated immunosuppression can be exploited to treat various autoimmune diseases. Methods of suppressing the CD28 pathway in accordance with the present invention are desirable since this pathway is resistant to the effects of cyclosporine, which is commonly used as an immunosuppressive agent in the treatment of autoimmune diseases. Immunosuppression via the CD28 pathway can restore immunoregulation and thus reduce the pathologic effects of such autoimmune diseases as systemic lupus erythematosis, rheumatoid arthritis, hemolytic anemia, myasthenia gravis, schleroderma, Sjögren's syndrome, ulcerative colitis, multiple sclerosis, and a host of other systemic as well as organ-specific autoimmune diseases.

Administration of stimulatory ligands (e.g. mAb 9.3, Kolt, B7) or inhibitory ligands (e.g. CTLA-4Ig, Fab fragments of mAb 9.3, and the like) can be in any suitable pharmacological form, including parenterally or topically. Pharmaceutical compositions may also take the form of ointments, gels, pastes, creams, sprays, lotions, suspensions, solutions and emulsions of the active ingredient in aqueous or nonaqueous diluents, syrups, granulates or powders. In addition to a ligand of the present invention, the pharmaceutical compositions can also contain other pharmaceutically active compounds or a plurality of compounds of the invention.

More particularly, a ligand of the present invention (also referred to herein as the active ingredient) may be administered by any suitable route, including parenteral (including subcutaneous, intramuscular, intravenous and intradermal), topical (including transdermal, buccal and sublingual), rectal, vaginal, nasal and pulmonary. Although the preferred route of administration is currently parenteral, it will be appreciated ihat the delivery route of choice will vary with the condition and age of the recipient and the nature of the disease or condition being treated.

While it is possible for the active ingredient to be administered alone, it is preferable to present it as a pharmaceutical formulation comprising at least one active ingredient, as defined above, together with one or more pharmaceutically acceptable carriers therefor and optionally other therapeutic agents. Each carrier must be "acceptable" in the sense of being compatible with other ingredients of the formulation and not injurious to the patient.

Formulations suitable for parenteral administration include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared form sterile powders, granules and tablets of the kind previously described.

Formulations include those suitable for parenteral (including subcutaneous, intramuscular, intravenous and intradermal), topical (including transdermal, buccal and sublingual), rectal, vaginal, nasal and pulmonary administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly and intimately bringing into associated the active ingredient with liquid carriers or finely divided solid carriers or both, and then if necessary shaping the product.

Pharmaceutical compositions for topical administration according to the present invention may be formulated as an ointment, cream, suspension, lotion, solution, paste, gel, spray aerosol or oil. Alternatively, a formulation may comprise a patch or a dressing such as a bandage or adhesive plaster impregnated with active ingredients and optionally one or more excipients or diluents. Formulations suitable for topical administration in the mouth include mouthwashes comprising the active ingredient in a suitable liquid carrier. It will also be appreciated that in a carrier suitable to preserve efficacy of the ligand, oral administration is also contemplated.

For conditions of the eye or other external tissues, e.g. mouth and skin, the formulations are preferably applied as a topical ointment or cream containing the active ingredient. When formulated in an ointment, the active ingredient may be employed with either a paraffinic or a water-miscible ointment base. Alternatively, the active ingredients may be formulated in a cream with an oil-in-water cream base. The topical formulations may desirably include a compound which enhances absorption or penetration of the active ingredient through the skin or other affected areas. Examples of such dermal penetration enhancers include dimethylsulphoxide and related analogues. Formulations suitable for topical administration to the eye also include eye drops wherein the active ingredient is dissolved or suspended in a suitable carrier, especially an aqueous solvent for the active ingredient.

Formulations for rectal administration may be presented as a suppository with a suitable base. Formulations for vaginal administration may be presented as pessaries, tampons, creams, gels, pastes, foams or spray formulations containing in addition to the active ingredient, such carriers as are known in the art to be appropriate. Formulations suitable for nasal administration, include formulations wherein the carrier is a liquid for administrations, for example, a nasal spray or a nasal drops, include aqueous or oily solutions of the active ingredient.

Preferred unit dosage formulations are those containing a daily dose or unit, daily subdose, or an appropriate fraction thereof, of the active ingredient. In any event, in practicing the present invention, the amount of active ingredient to be used or administered, alone or in combination with other agents, will vary with the patient being treated and will be monitored on a patient-by-patient basis by the physician. Generally, a therapeutically effective amount of the vaccine will be administered for a therapeutically effective duration. By "therapeutically effective amount" and "therapeutically effective duration" are meant an amount and duration to achieve the result desired in accordance with the present invention without undue adverse or with medically acceptable physiological effects, which effects can be determined by those skilled in the medical arts. It will also be appreciated that, particularly when a natural ligand is used in the practice of the invention, its isolation or production should render it substantially free of undesirable contaminants such as other proteins (i.e. "substantially pure") which may adversely impact on its efficacy or use. Acceptable levels of purity can be determined by those skilled in the pharmaceutical and medical arts and can depend on the specific ligand and composition and its intended use.

It should also be understood that in addition to the ingredients particularly mentioned above, the formulations of this invention may include other agents conventional in the art having regard to the type of formulation in question. In accordance with the present invention, ligands may also be presented for the use in the form of veterinary formulations, which may be prepared, by methods conventional in the art.

Accumulating evidence suggests that in addition to T cell receptor occupancy, other costimulatory signals are required to induce a complete T cell-mediated immune response. The CD28 receptor expressed on T cells serves as a surface component of a novel signal transduction pathway that can induce paracrine levels of cellular production of lymphokines. Interaction of CD28 with its natural ligand B7 which is expressed on the surface of activated B cells macrophages or dendritic cells can act as a costimulus to induce high level lymphokine production in antigen receptor-activated T cells. Thus, another approach to down-regulation is to inhibit the activation of the CD28 signal transduction pathway as described below.

Although the CD28 signal transduction pathway is not entirely understood, Specific Example XI demonstrates that binding of CD28 induces protein tyrosine phosphorylation distinct from T cell receptor (TCR)-induced tyrosine phosphorylation. For example, TCR-induced tyrosine phosphorylation occurs in both resting and activated T cells, while CD28-induced tyrosine phosphorylation occurs primarily in previously activated T cells. Most striking were the results after CD28 receptor ligation by cell-bound B7, where phosphorylation was consistently detectable on only a single substrate. Experiments using the Jurkat E6–1 T cell line indicated an absolute requirement for PMA pretreatment in order to observe CD28-induced tyrosine phosphorylation. In contrast, there was no requirement for cellular preactivation in the Jurkat J32 line, while, as noted above, there was a relative requirement for PMA or TCR prestimulation of normal T cells in order to induce CD28 responsiveness. Studies with Jurkat mutants further indicated that CD28-induced tyrosine phosphorylation and biologic function can occur in the absence of the TCR. In this respect, CD28 appears to be unique in that other accessory molecules involved in T cell activation, such as CD2, Ly-6, Thy-1, and CD5 appear to require the presence of the TCR. Thus, specific tyrosine phosphorylation appears to occur directly as a result of CD28 ligand binding and is involved in transducing the signal delivered through CD28 by accessory cells that express the B7/BB1 receptor.

Studies with an inhibitor of the src family of tyrosine kinases, herbimycin A, and with tyrosine phosphatase, as described in Specific Example XI, further show that the functional effects of CD28 stimulation on lymphokine gene expression require the above-described protein tyrosine phosphorylation. The data on tyrosine phosphorylation inhibitors thus demonstrate that inactivation of CD28-mediated signal transduction can also be used to down-regulate lymphokine production in accordance with the principles of the present invention.

Immunotherapy through CD28 stimulation in accordance with the present invention also has clinical applicability in the treatment of bone marrow transplant recipients. The success of autologous and allogeneic bone marrow transplantation (BMT) has generally been limited by recurrent malignancy, graft-vs-host disease (GVHD), and the life-threatening immune deficiency that occurs after BMT. One approach to overcoming these problems has been the adoptive transfer of lymphocytes in combination with lymphokine infusions, to accelerate immune reconstitution or mediate cytotoxicity directed at malignant cells. The side effects attending such transfer with lymphokine infusions are, however, quite significant.

Thus, T cell proliferation and lymphokine synthesis in the absence of exogenously added IL-2 in response to CD3 and CD28 costimulation, as described in Specific Example XIII, provides a unique opportunity for clinical use of adoptive transfer of activated T cells to repair T cell defect in vivo without exogenous lymphokine infusions. The studies detailed in Specific Example XIV show that defective in vitro proliferative responses to anti-CD3 (OKT3 or G19-4) can be repaired by adding mAb 9.3 to the cultures. See Joshi, I. et al., *Blood Suppl.* (Abstract) (1991). Costimulation of T cells with OKT3/9.3 repaired proliferative responses as a result of increasing the levels of MRNA expression for cytokines/lymphokines such as IL-2, GM-CSF, and TNFα. See Joshi, supra; Perrin, P. J. et al, *Blood Suppl.* (Abstract) (1991). Purified normal $CD4^+$ cells can thus be costimulated with OKT3/9.3 to expand and secrete lymphokines for long periods of time. Preclinical studies using mAb 9.3 stimulation have shown no untoward effects in monkeys. Although CD3-stimulated cells (CTC) provide helper factors to normal B cells, CD3-CD28 costimulated cells appear even more effective in producing helper factors than CD3-stimulated T cells. Thus, costimulation may also enhance the growth of helper cells and cytotoxic T cells for adoptive immunotherapy after BMT. The administration in vivo of T cells that have been expanded in vitro, will provide two prominent benefits in marrow transplantation. The ability of CD28-treated cells to produce many lymphokines which have a strong positive effect on hematopoiesis, such as GM-CSF, IL-3, and IL-6, should accelerate engraftment after marrow transplantation. In addition, the ability of anti-CD28 to trigger cytotoxicity and to cause the production of lymphokines such as TNF is a novel form of adoptive immunotherapy that should augment the anti-neoplastic efficacy of bone marrow transplantation.

The possible role of CD28 in anergy was also examined. Generally, the activation of a quiescent T cell is initiated through stimulation of the T cell antigen receptor. This activation can occur either through engagement of an antigenic peptide presented in the antigen binding groove of a self-encoded MHC molecule or by engagement of a foreign MHC molecule. However, while this receptor-mediated activation event is required for the initiation of a T cell response in a quiescent cell, recent studies have demonstrated that signals transduced by the antigen receptor alone are not sufficient to lead to an effective T cell-mediated immune response. Several in vitro models suggest that, in fact, T cell receptor (TCR)/CD3 activation alone of a quiescent T cell leads to the induction of a state in which the T cell becomes anergic to further stimulations through its antigen-specific receptor. This state is relatively long-lived and, for at least several weeks, renders that cell incapable of further response upon antigenic stimulation. It is hypothesized that this isolated activation of the TCR/CD3 complex alone in the absence of additional T cell costimulatory molecules plays an important role in regulating a peripheral immune response by preventing T cells from responding to self antigens in the periphery.

Thus, for T cells to mount a proliferative response and initiate a cell-mediated immune response, a quiescent T cell normally requires stimulation not only through its antigen-specific T cell receptor but also through a second receptor which provides additional costimulatory signals to the cell. The data set forth herein, e.g. in Specific Example XII, demonstrates that CD28 provides an essential costimulatory signal for T cell responses in vitro and in vivo. Thus, the CD28 receptor's ability to augment T cell lymphokine production not only results in the initiation of a cell-mediated immune response, but also prevents the induction of anergy in a quiescent T cell.

The role of CD28 in the prevention of programmed cell death has also been tested. The induction of cell death has a major role in the elimination of self-reactive or non-reactive T cells in the thymus. In the thymus, it is thought that T cell receptor signals are able to induce programmed cell death, in a selective and specific fashion involving cells that express T cell receptors specific for self-antigens. As described in Turka, L. A. et al., *J. Immunol.*, 144:1646–53 (1990), CD28 is expressed in developing T cells in the thymus, and the binding of mAb 9.3 prevents thymocyte cell death. Programmed cell death is also thought to occur in mature T cells in peripheral lymphoid organs. Signals delivered through the T cell receptor can induce cell death (see Newell, M. K., et al., *Nature*, 347:286–8 (1990)). It has also been proposed that cell death may have a role in certain forms of immunopathology. For example, in HIV-1 infection it has been proposed that the progressive immunodeficiency may be the result of immunologically-mediated cell death, rather than a direct consequence of viral-induced cytopathic effects. See Ameisen, J. C. et al., *Immunol. Today*, 4:102 (1991); also see Groux H., et al., *J. Exp. Med.* 175:331–340 (1992). The results in Specific Example XIII show that CD28 can prevent cell death in mature T cells. Thus, abnormal expression or activation of CD28 may have a role in immunopathology of certain autoimmune disorders such as systemic lupus erythematosus, a disorder characterized by abnormally self-reactive T cells that have failed to undergo elimination in the thymus or escape from anergic states in the peripheral lymphoid system. Similarly, the ability to induce CD28 activation may be beneficial in disorders characterized by progressive T cell depletion such as HIV-1 infection.

It was also demonstrated in Specific Example XII that superantigens SEA and SEB, which do not require traditional processing for binding to MHC, can directly activate purified T cells in the absence of accessory cells as determined by a transition from $G_0$ to $G_1$ and induction of IL-2 receptor expression. However, neither SEA nor SEB alone was sufficient to result in T cell proliferation. The induction of T cell proliferation by SEB or SEA required the addition of a second costimulatory signal. This could be provided by either accessory cells or monoclonal antibody stimulation of CD28. As previously reported, T cell proliferation induced by enterotoxin in the presence of accessory cells was partially inhibited by a blocking antibody (HLA-DR) against class II MHC. In contrast, in purified T cells when costimulation was provided through CD28, proliferation was not inhibited by class II antibody and HLA-DR expression was not detectable. In addition, costimulation through CD28 was partially resistant to the effects of cyclosporine. These results demonstrate that CD28 costimulation is sufficient to induce lymphokine production and subsequent proliferation of enterotoxin-activated T cells, and that this effect is independent of class II MHC expression. This prevention of in vivo CD28 activation of superantigen-activated cells such as those occurring in toxic shock syndrome and rheumatoid or lyme arthritis, may substantially decrease disease morbidity.

Although as noted previously the present invention is not intended to be restricted to specific mechanisms of activation, the role of CTLA-4 in the CD28 activation pathway has been examined and models consistent with the data presented herein have been postulated. (See e.g. Specific Example XV.) Recent work in our laboratory has shown that the CTLA-4 gene lies immediately adjacent to CD28 on chromosome 2, with a similar genomic organization and 32% amino acid homology. Based on their chromosomal localization and sequence and organizational similarities, CD28 and CTLA-4 likely represent evolutionary gene duplication. By standard nomenclature they might thus more appropriately be named CD28α and CD28β, although the terms CD28 and CTLA-4 are retained herein.

Although CTLA-4 is not expressed on quiescent lymphoid cells, its expression at the RNA level can be rapidly induced upon T cell activation. Two potential mechanisms by which CTLA-4 might function are postulated as follows. First, since CD28 and CTLA-4 contain an unpaired cysteine in their extracellular domain, this cysteine residue may be used to form crosslinked dimeric receptors on the surface. If this were the case, it may suggest that CTLA-4 is normally expressed on the surface as a heterodimer with CD28. Under such conditions, the higher affinity of CTLA-4 for the natural ligand B7 might in the dimeric state lead to a higher affinity receptor with enhanced signaling capabilities. This might allow for an enhanced signal transduction capability through the CD28-CTLA-4 heterodimer in an antigen-activated cell. In addition, if CD28 and CTLA-4 are found primarily in activated cells in a heterodimeric state, this might account for observations that CD28-containing receptors have enhanced signaling capabilities in activated cells.

On the other hand, the data presented herein are also compatible with a model in which CTLA-4 is induced upon T cell activation as a competitive inhibitor of CD28 and is used to down-modulate an ongoing immune response by inhibiting further interactions between B7 and CD28 on the surface. In addition, it is quite possible that the CTLA-4 expressed on the surface is also expressed in a shed form, and this shed form of the receptor acts as a soluble competitive inhibitor of an ongoing B7-CD28 interaction, thereby preventing the antigen-presenting cell from activating additional T cells in its environment. Thus, the ability of T cells to produce an additional isoform of CD28, i.e. CTLA-4, suggests that the interplay of expression of CD28 and CTLA-4 has profound effects on the ability of T cells to be activated through a CD28-containing receptor.

CD28 pathway activation and inhibition studies indicate that the ability of the CD28 natural ligand B7 to activate a T cell to augment lymphokine production is entirely mediated through a CD28-containing receptor, either a CD28 homodimer or a CD28-CTLA-4 heterodimer. Thus, the data suggest that a CTLA-4 homodimer is not critical in T cell activation, but may play an important role in down-modulation of T cell lymphokine production, while a CD28-CTLA-4 heterodimer may account for the enhanced signaling properties of CD28-containing receptors upon T cell activation.

The role of CTLA-4 in CD28-mediated signal transduction event may explain why the novel and profound effects of CD28 on normal T cell activation encountered and described herein were not previously observed in human T cell lines. Earlier work on the CD28 pathway occurred in cell lines such as Jurkat human T cells. Extensive attempts to stimulate these cells to express CTLA-4 have been entirely negative (see FIG. 20). In contrast, standard activation events that lead to cell cycle progression of normal T cells either through chemical mitogens such as phytohemagglutinin (PHA) and phorbol myristate acetate (PMA) leads to rapid induction of CTLA-4 expression as does crosslinking of the TCR/CD3 complex. Therefore, the inability of previous investigators to appreciate or harness the CD28 activation pathway to enhance cellular production of lymphokines was likely due to the lack of expression of the CTLA-4 isoform of CD28 in these cell lines. Interestingly, costimulation of resting T cells with anti-CD28 monoclonal antibodies enhances the expression of the CTLA-4 gene (see FIG. 21). Thus, the CD28 activation pathway in normal cells may in fact involve a positive feedback loop in which initial CD28 stimulation through the CD28 homodimer enhances the expression of CTLA-4 thus leading to enhanced heterodimer expression and signal transduction. Alternatively, the enhanced CTLA-4 may lead to the production of a receptor which competes for CD28 signal transduction thus leading to the ultimate termination of lymphokine production and acts as a negative feedback loop to down modulate an ongoing CD28-mediated lymphokine production.

SPECIFIC EXAMPLE I

Preparation of CD28 Stimulator Monoclonal Antibody 9.3

The monoclonal antibody (mAb) 9.3, an IgG2a monoclonal antibody which binds to the extracellular domain of the CD28 molecule, was produced by a hybrid cell line originally derived as described by Hansen et al., *Immunogen.*, 10:247–260 (1980). Ascites fluid containing high titer monoclonal antibody 9.3 was prepared by intraperitoneal inoculation of $5-10 \times 10^6$ hybrid cells into a Balb/C×C57BL/6 $F_1$ mice which had been primed intraperitoneally with 0.5 ml of Pristane (Aldrich Chemical Co., Milwaukee, Wis.). The monoclonal antibody 9.3 was purified from ascites fluid on a staphylococcal protein-A sepharose column as described by Hardy, R., "Handbook of Experimental Immunology," Ch. 13 (1986).

Prior to use in functional assays, purified mAb 9.3 was dialyzed extensively against phosphate buffered saline (KCl 0.2 grams/liter $dH_2O$; $KH_2PO_4$ 0.2 grams/liter $dH_2O$; NaCl 8.0 grams/liter dH2O; $Na_2HPO_4.7H_2O$ 2.16 grams/liter $dH_2O$) and then filtered through a 0.22 cubic micron sterile filter (Acrodisc, Gelman Sciences, Ann Arbor, Mich.). The mAb 9.3 preparation was cleared of aggregates by centrifugation at 100,000×g for 45 m at 20° C. The resulting purified mAb 9.3 was resuspended in phosphate buffered saline to a final concentration of 200 µg/ml as determined by $OD_{280}$ analysis and stored at 4° C. prior to use.

SPECIFIC EXAMPLE II

Isolation of $CD28^+$ T Cells

Buffy coats were obtained by leukopheresis of healthy donors 21 to 31 years of age. Peripheral blood lymphocytes (PBL), approximately $2.5 \times 10^9$, were isolated from the buffy coat by Lymphocyte Separation Medium (Litton Bionetics, Kensington, Md.) density gradient centrifugation. The $CD28^+$ subset of T cells was then isolated from the PBL by negative selection using immunoabsorption, taking advantage of the reciprocal and non-overlapping distribution of the CD11 and CD28 surface antigens as described by Yamada et al., *Eur. J. Immunol.*, 15:1164–1688 (1985). PBL were suspended at approximately $20 \times 10^6$/ml in RPMI 1640 medium (GIBCO Laboratories, Grand Island, N.Y.) containing 20 mM HEPES buffer (pH 7.4) (GIBCO Laboratories, Grand Island, N.Y.), 5mM EDTA (SIGMA Chemical Co., St. Louis, Mo.) and 5% heat-activated human AB serum (Pel-Freez, Brown Deer, Wis.). The cells were incubated at 4° C. on a rotator with saturating amounts of monoclonal antibodies 60.1 (anti-CD11a) (see Bernstein, I.D. et al., "Leukocyte Typing II," Vol. 3, pgs. 1–25, ed. Reinherz, E. L. et al., (1986); 1F5 (anti-CD20) (see Clark, E. A. et al., *PNAS* (USA), 82:1766–1770 (1985)); FC-2 (anti-CD16) (see June, C. H. et al., *J. Clin. Invest.*, 77: 1224–1232 (1986)); and anti-CD14 for 20 m. This mixture of antibodies coated all B cells, monocytes, large granular lymphocytes and $CD28^-$ T cells with mouse immunoglobulin. The cells were washed three times with PBS to remove unbound antibody, and then incubated for 1 h at 4° C. with goat anti-mouse immunoglobulin-coated magnetic particles (Dynal, Inc., Fort Lee, N.J.) at a ratio of 3 magnetic particles per cell. Antibody-coated cells that were bound to magnetic particles were then removed by magnetic separation as described by Lea, T. et al., *Scan. J. Immunol.*, 22:207–216 (1985). Typically, approximately $700 \times 10^6$ $CD28^+$ T cells were recovered. Cell purification was routinely monitored by flow cytometry and histochemistry. Flow cytometry was performed as described by Ledbetter, J. A. et al., "Lymphocyte Surface Antigens," pgs. 119–129 (ed. Heise, E., 1984). Briefly, CD28+ T cells were stained with fluorescein isothiocyanate (FITC)-conjugated anti-CD2 mAb OKT11 (Coulter, Hialeah, FL) and with FITC-conjugated anti-CD28 mAb 9.3 as described by Goding, J. W., "Monoclonal Antibodies Principles and Practice," p. 230 (ed. Goding, J. W., 1983). CD28+ T cells were over 99% positive with FITC-conjugated monoclonal antibody OKT11 and over 98% positive FITC-conjugated monoclonal antibody 9.3 when compared to a non-binding, isotype-matched, FItC-labeled control antibody (Coulter, Hialeah, Fla.). Residual monocytes were quantitated by staining for non-specific esterase using a commercially available kit obtained from Sigma Chemical Co., St. Louis, Mo., and were less than 0.1% in all cell populations used in this study. Viability as approximately 98% as measured by trypan blue exclusion as described by Mishell, B. B. et al., "Selected Methods in Cell. Immunology," pgs. 16–17 (1980).

SPECIFIC EXAMPLE III

Increased Cellular Production of Human $T_H$CD28 Lymphokines by CD28 Stimulation by Monoclonal Antibody 9.3

A. Increased Production of IL-2, TNF-α, IFN-γ and GM-CSF.

CD28+ T cells were cultured at approximately $1 \times 10^5$ cells/well in the presence of various combinations of stimulators. The stimulators included phorbol myristate acetate (PMA) (LC Services Corporation, Woburn, Ma.) at 3 ng/ml conc.; anti-CD28 mAb 9.3 at 100 ng/ml; anti-CD3 mAb G19-4 at 200 ng/ml which was immobilized by adsorbing to the surface of plastic tissue culture plates as previously described by Geppert, et al., *J. Immunol.*, 138:1660–1666 (1987); also Ledbetter, et al., *J. Immunol.*, 135: 2331–2336 (1985); ionomycin (Iono) (Calbiochem., San Diego, Calif.) at 100 ng/ml. Culture supernatants were harvested at 24 h and serial dilutions assayed for the presence of $T_H$CD28 lymphokines.

Specifically, IL-2 was assayed using a bioassay as previously described by Gillis et al., *Nature*, 268:154–156 (1977). One unit (U) was defined as the amount of IL-2 needed to induce half maximal proliferation of $7 \times 10^3$ CTLL-2 (a human cytotoxic T cell line) cells at 24 h of culture. In separate experiments, the relative levels of IL-2 for each of the culture conditions above were independently confirmed using a commercially available ELISA assay (Genzyme Corp., Boston, Mass.). TNF-α/LT levels were measured using a semi-automated L929 fibroblast lytic assay as previously described by Kunkel et al., *J. Biol. Chem.*, 263:5380–5384 (1988). Units of TNF-α/LT were defined using an internal standard for TNF-α (Genzyme Corp., Boston Mass.). The independent presence of both TNF-α and LT was confirmed by the ability of a monoclonal antibody specific for each cytokine to partially inhibit cell lysis mediated by the supernatant from cells costimulated with immobilized anti-CD3 mAb G19-4 and anti-CD28 mAb 9.3. IFN-γ was measured by radioimmunoassay using a commercially available kit (Centocor, Malvern, Pa.). Units for IFN-γ were determined from a standard curve using $^{125}$I-labeled human IFN-γ provided in the test kit. GM-CSF was detected by stimulation of proliferation of the human GM-CSF-dependent cell line AML-193, as described by Lange et al., *Blood*, 70:192–199 (1987), in the presence of neutralizing monoclonal antibodies to TNF-α and LT. The $^3$H-thymidine uptake induced by 10 ng/ml of purified GM-CSF (Genetics Institute, Cambridge, Mass.) was defined as 100 U. Separate aliquots of cells were recovered 48 h after stimulation and assayed for the percentage of cells in late stages of the cell cycle ($S+G_2+M$) by staining of cells with propidium iodide and analysis by flow cytometry as previously described by Thompson et al., *Nature*, 314:363–366 (1985).

As shown in Table 1, CD28 stimulation of CD3-stimulated T cells resulted in marked increases in cellular production of IL-2, TNF-α, IFN-γ and GM-CSF.

TABLE 1

Increased Cellular Production of $T_H$CD28 Lymphokines by CD28 Stimulation

| STIMULUS | IL-2 (U/ml) | TNF-α/LT (U/ml) | IFN-γ (U/ml) | GM-CSF (U/ml) | $S + G_2 + M$ (%) |
|---|---|---|---|---|---|
| Medium | <2 | 0 | 0 | 0 | 4.6 |
| PMA | <2 | 0 | 0 | NT | 5.5 |
| anti-CD28 | <2 | 5 | 0 | 0 | 6.5 |
| anti-CD28 + PMA | 435 | 300 | 24 | 150 | 48.9 |
| anti-CD3$^i$ | 36 | 50 | 24 | 120 | 39.7 |
| anti-CD3$^i$ + anti-CD28 | 1200 | 400 | 74 | 1050 | 44.7 |
| Ionomycin | <2 | 0 | 0 | NT | 6.6 |
| Ionomycin + PMA | 200 | 5 | 37 | NT | 43.6 |
| Ionomycin + PMA + anti-CD28 | 1640 | 320 | 128 | NT | 43.5 |

$^i$= immobilized
NT = not tested

B. Effects of Anti-CD28 Stimulation on T cell IL-4, IL-5 and IL-3 Secretion.

Previous studies of the effects of anti-CD28 Mab stimulation on T cell production of lymphokines of the $T_H2$ type were limited to the first few days of stimulation. In those studies IL-4 could not be detected after anti-CD28 stimulation (noted in Thompson et al., *PNAS* 86:1333 (1989)). On reexamination of this question, it was found that anti-CD28 can augment production of IL-4 and of IL-5, and thus, augments production of $T_H2$ lymphokines as well as the $T_H1$ type lymphokines previously described. As can be seen in Table 2, small amounts of both IL-4 and IL-5 can be detected after 24 h of stimulation with anti-CD3 plus anti-CD28. However, when cells are restimulated after 8 days in culture, large amounts of both IL-4 and IL-5 are secreted. As shown in Table 3, similar results were found when the CD28 subset of T cells were stimulated with the combination of phorbol myristate acetate (PMA) and anti-CD28 mAb. These results indicated that small amounts of IL-4 and IL-5 can be detected after initial stimulation of resting T cells with anti-CD28. However, with continued stimulation, differentiation occurs, and large amounts of IL-4 and, particularly, of IL-5 are produced, while lesser amounts of IL-2 and γ-IFN are also produced.

TABLE 2

Effects of anti-CD3 and anti-CD28 Treatment of IL-4 and IL-5 Production by T cells

| STIMULUS | INITIAL | | | | RESTIMULATION | | | |
|---|---|---|---|---|---|---|---|---|
| | IL-4 pg/ml | IL-5 pg/ml | IFN pg/ml | IL-2 U/ml | IL-4 pg/ml | IL-5 pg/ml | IFN pg/ml | IL-2 U/ml |
| Medium | <1 | <1 | <1 | <0.1 | <1 | <1 | <1 | <0.1 |
| anti-CD3 | <1 | <1 | 630 | 2.3 | 220 | 225 | 246 | 0.02 |
| anti-CD3 + anti-CD28 | 207 | 137 | 887 | 7.0 | 498 | 2545 | 379 | 0.2 |

The data in Table 2 above were obtained using the following protocol: CD28$^+$ T cells were isolated by negative selection using monoclonal antibodies and magnetic immunobeads as described in Specific Example II. The cells were cultured at 1×10$^6$/ml in RPMI medium containing 10% FCS (Medium), or in culture wells containing anti-CD3 monoclonal antibody G19-4 absorbed to the plastic, or plastic adsorbed anti-CD3 plus anti-CD28 mAb 9.3 added in solution at 0.5 μg/ml. Supernatants from the cell culture were analyzed for lymphokine concentration using commercially available ELISA kits and the values expressed as pg/ml for IL-4, IL-5 and γ-IFN, or as units per ml, for IL-2. Supernatants were analyzed after 24 h of culture (Initial) or alternatively, the cells were cultured for 8 days in the above forms of stimulation, the cells were recovered, washed, and then restimulated with their original treatment, and the supernatants analyzed after a further 24 h of stimulation (Restimulation). The values represent means of duplicate cultures.

detail in Guba, S. C. et al., *J Clin. Invest.* 84(6):1701–1706 (1989), incorporated herein by reference.

PBL were isolated as described previously. The CD28$^+$ subset of T cells was isolated by negative selection as described by June, C. H. et al., *Mol. Cell. Biol.* 7:4472–4481 (1987). In some experiments, the CD28$^+$ subset of T cells was isolated by incubating PBL with mAB 9.3, and then removing the CD28$^+$ cells with goat anti-mouse coated magnetic beads (Advanced Magnetics Institute, Cambridge, Mass.). Northern (RNA) blot analysis was done as described by June, C. H. et al., *Mol. Cell. Biol.* 7:4472–4481 (1987). The IL-3 probe was a 1.0 kb Xho I cDNA fragment.

To determine if stimulation of the TCR/CD3 pathway of T cell activation induced IL-3 gene expression, CD28$^+$ T cells were stimulated with maximal amounts of plastic immobilized anti-CD3 mAb in the presence or absence of 9.3 mAb 1 μg/ml for 1 to 36 h. As shown in Table 4, anti-CD28 resulted in a 3 to 5-fold augmentation of IL-3

TABLE 3

Effects of PMA and anti-CD28 Treatment on IL-4 and IL-5 Production by T cells

| STIMULUS | INITIAL | | | | RESTIMULATION | | | |
|---|---|---|---|---|---|---|---|---|
| | IL-4 pg/ml | IL-5 pg/ml | IFN pg/ml | IL-2 U/ml | IL-4 pg/ml | IL-5 pg/ml | IFN pg/ml | IL-2 U/ml |
| Medium | <1 | <1 | <1 | <0.1 | <1 | <1 | <1 | <0.1 |
| PMA | <1 | <1 | 152 | .07 | <1 | <1 | <1 | 0.6 |
| anti-CD28 + PMA | <1 | 187 | 558 | 8.1 | 285 | 392 | 335 | 10.3 |

The data in Table 3 above were obtained using the following protocol: CD28$^+$ T cells were isolated by negative selection using monoclonal antibodies and magnetic immunobeads as described in Specific Example II. The cells were cultured at 1×10$^6$/ml in RPMI medium containing 10% FSC (Medium), or in medium plus PMA 3 ng/ml, or in PMA plus anti-CD28 Mab 9.3 at 0.5 μg/ml. Supernatants from the cell culture were analyzed for lymphokine concentration using commercially available ELISA kits and the values expressed as pg/ml for IL-4, IL-5 and γ-IFN. Supernatants were analyzed after 24 h of culture (Initial) or, alternatively, the cells were cultured for 8 days in the above forms of stimulation, and then restimulated, and the supernatants analyzed after a further 24 h period of stimulation (Restimulation). The values represent means of duplicate cultures.

Induction of IL-3 expression in T cells after anti-CD28 treatment. IL-3 is a multilineage hematopoietic growth factor that is primarily produced by T cells, and is generally considered to be produced by $T_H1$ cells. The experimental protocol and the findings described herein are described in mRNA expression over that induced by anti-CD3 alone. CD28 did not change the kinetics of IL-3 gene expression, which was at peak levels at 6 h after anti-CD3 or after anti-CD3+anti-CD28 treatment. Further experiments showed that IL-3 gene expression was restricted to the CD28$^+$ subset of T cells, as determined by Northern analysis (Table 4). The stability of IL-3 mRNA was also determined. T cells were treated for 3 h with anti-CD3 or anti-CD3 plus anti-CD28 mAb to induce IL-3 mRNA expression. At 3 h, actinomycin D was added to the culture to inhibit further RNA synthesis. Total cellular RNA was isolated, and the remaining IL-3 mRNA determined by Northern analysis. The half-life of IL-3 mRNA from anti-CD3 plus anti-CD28 treated cells was at least 8-fold longer than the IL-3 mRNA from anti-CD3 treated cells (Table 4). Thus, as would be expected from the previously described results of anti-CD28 on other lymphokines, it can be concluded that the effect of anti-CD28 on IL-3 gene induction can, in large part, be explained by the ability of anti-CD28 to stabilize the IL-3 messenger RNA.

TABLE 4

| CONDITION | IL-3 GENE EXPRESSION (arbitrary densitometry units) |
|---|---|
| EXPERIMENT #1 | |
| $CD28^+$ T cells, 6 h, anti-CD3 | 1 |
| $CD28^+$ T cells, 6 h, anti-CD3 + anti-CD28 | 3–5 |
| EXPERIMENT #2 | |
| $CD28^+$ T cells, 8 h, PMA 3 ng/ml + Ionomycin 0.4 μg/ml | >10 |
| $CD28^-$ T cells, 8 h, PMA 3 ng/ml + Ionomycin 0.4 μg/ml | <1 |
| EXPERIMENT #3 | |
| $CD28^+$ T cells, anti CD3, then actinomycin D 90 m | 1 |
| $CD28^+$ T cells, anti-CD3 + anti-CD28, then actinomycin D 90 m | 8 |

SPECIFIC EXAMPLE IV

Comparison of CD28 Stimulation to Stimulation of Other T Cell Surface Molecules $CD28^+$ T cells were cultured at approximately $1 \times 10^5$ cells/well in RPMI media containing 5% heat-inactivated fetal calf serum (FCS), PHA 10 μg/ml, PMA 3 ng/ml, ionomycin at 100 ng/ml, anti-CD28 mAb 9.3 at 100 at ng/ml, or mAb 9.4 specific for CD45 at 1 μg/ml or mAb 9.6 specific for CD2 at 1 μg/ml, or immobilized mAb G19-4 specific for CD3 at 200 ng/well.

$CD28^+$ T cells were cultured in quadruplicate samples in flat-bottomed 96-well microtiter plates in RPMI media containing 5% heat-inactivated fetal calf serum. Equal aliquots of cells were cultured for 18 h and then pulsed for 6 h with 1 μCi/well of $^3$H-uridine, or for 72 h and then pulsed for 6 h with 1 μCi/well of $^3$H-thymidine. The means and standard deviations (in cpm) were determined. by liquid scintillation counting after cells were collected on glass fiber filters.

All cultures containing cells immobilized to plastic by anti-CD3 monoclonal antibodies were visually inspected to ensure complete cell harvesting. The failure of cells in these cultures to proliferate in response to PHA is the result of rigorous depletion of accessory cells, in vivo activated T cells, B cells, and $CD11^+$ ($CD28^-$) T cells by negative immunoabsorption as described in Specific Example II above. In each experiment, cells were stained with fluorescein-conjugated anti-CD2 mAb OKT11 and fluorescein-conjugated anti-CD28 mAb 9.3 and were shown to be over 99% and over 98% surface positive, respectively.

Figure 2:
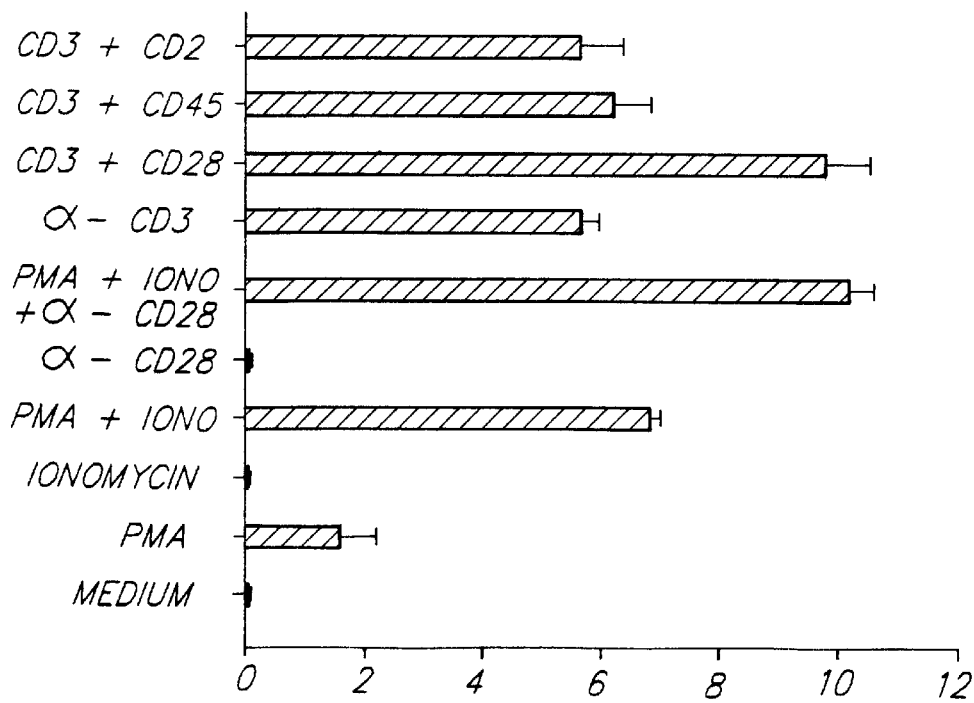
FIG. 2 is a bar graph illustrating the increase in uridine incorporation by CD28 stimulation of anti-CD3 stimulated T cells.

A representative experiment is illustrated in FIGS. 1 and 2. As shown in FIGS. 1 and 2, anti-CD28 by itself had no significant effect on uridine or thymidine incorporation, nor did it serve to augment proliferation induced either by immobilized anti-CD3 mAb G19-4 or chemically-induced T cell proliferation involving phorbol myristate acetate (PMA) and ionomycin (Iono). However, as shown in FIG. 2, anti-CD28 did significantly increase the uridine incorporation of both sets of cells. In contrast, other monoclonal antibodies including anti-CD2 mAb OKT11 and anti-CD45 mAb 9.4 had no significant effect on uridine incorporation of anti-CD3 stimulated cells. This was not due to lack of effect of these antibodies on the cells, since anti-CD2 monoclonal antibodies significantly augmented the proliferation of anti-CD3 stimulated cells. In separate experiments, the binding of isotype-matched mAbs to other T cell surface antigens (CD4, CD6, CD7 or CD8) failed to mimic the effects observed with anti-CD28.

These data serve to confirm that the stimulation of activated T cells by CD28 has a unique phenotype which appears to directly enhance the rate of incorporation of a radioactive marker into the steady state RNA of T cells without directly enhancing T cell proliferation.

SPECIFIC EXAMPLE V

Increased Cellular Production of Human $T_H$CD28 Lymphokines by CD28 Stimulation Ex Vivo Based on evidence from the in vitro systems it appeared that CD28 did not have a significant effect on cellular production of lymphokines unless they had undergone prior antigen activation or its equivalent. However, CD28 binding by the 9.3 mAb significantly enhanced the ability of anti-TCR/CD3 activated T cells to sustain production of human $T_H$1-type lymphokines. To test this effect in a physiologic setting, the activation of T lymphocytes in an ex vivo whole blood model was studied.

50–100 ml of venous blood was obtained by standard aseptic procedures from normal volunteers after obtaining informed consent. The blood was heparinized with 25 U/ml of preservative-free heparin (Spectrum, Gardenia, Calif.) to prevent clotting. Individual 10 ml aliquots were then placed on a rocking platform in a 15 ml polypropylene tube to maintain flow and aeration of the sample.

To assay for the effectiveness of CD28 stimulation on the induction of lymphokine gene expression, the production of TNF-α molecule was chosen as a model because of the extremely short half-life (approximately 15 minutes) of the protein in whole blood. 10 ml of whole blood isolated as described above was incubated with soluble anti-CD3 mAb G19-4 at a concentration of 1 μg/ml or anti-CD28 mAb 9.3 at a concentration of 1 μg/ml or a combination of the two antibodies. The plasma was assayed for TNF-α as described in Specific Example III at one and four h. An example of one such experiment is shown in Table 5, which illustrates the significant increase in sustained production of TNF-α by maximal stimulation of CD3 and costimulation of CD28.

TABLE 5

| | TNF-α (pg/ml) | | |
|---|---|---|---|
| STIMULUS | 0 h | 1 h | 4 h |
| anti-CD3 | 4.5[a] | 65.0 | 2.1 |
| anti-CD28 | 4.5[a] | 1.6 | 3.3 |
| anti-CD3 + anti-CD28 | 4.5[a] | 35.0 | 75.0 |

[a]value determined prior to addition of monoclonal antibody to aliquots of the venous sample

SPECIFIC EXAMPLE VI

Resistance of CD28-Induced T Cell Proliferation to Cyclosporine

The protocol used and results described herein are described in detail in June, C. H. et al., *Mol. Cell. Biol.*, 7: 4472–4481 (1987), herein incorporated by reference.

T cells, enriched by nylon wool filtration as described by Julius, et al., *Euro. J. Immunol.*, 3:645–649 (1973), were cultured at approximately $5 \times 10^4$/well in the presence of stimulators in the following combinations: anti-CD28 mAb 9.3 (100 ng/ml) and PMA 1 (ng/ml); or immobilized anti- CD3 mAb G19-4 (200 ng/well); or PMA (100 ng/ml). The above combinations also included fourfold titrations (from 25 ng/ml to 1.6 μg/ml) of cyclosporine (CSP) (Sandoz, Hanover, N.J.) dissolved in ethanol-Tween 80 as described by Wiesinger, et al., *Immunobiol.*, 156:454–463 (1979).

Figure 3:
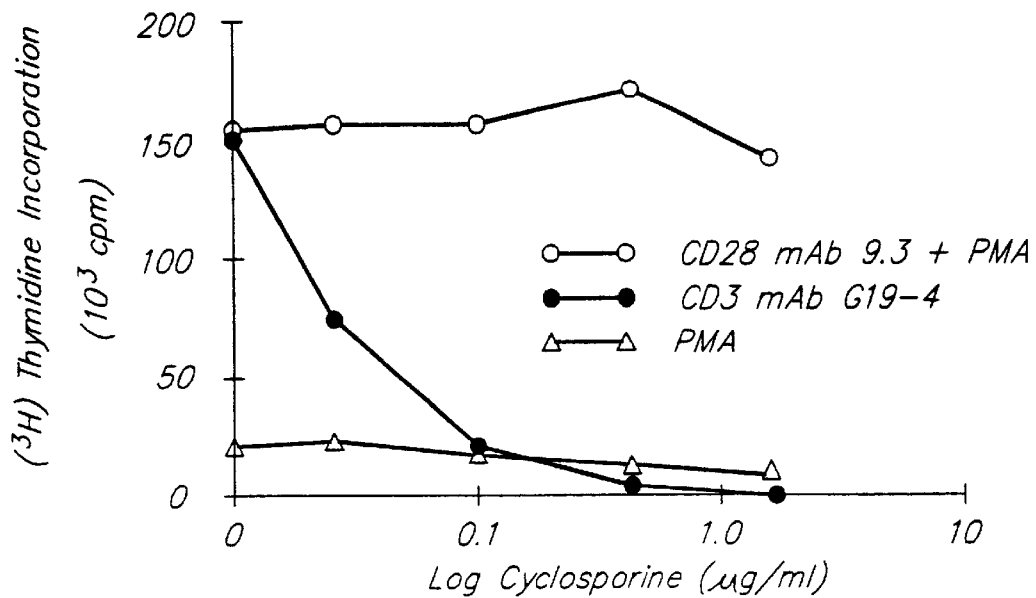
FIG. 3 is a graph illustrating the elevated cyclosporine resistance of T cell proliferation induced by CD28 stimulation.

$^3$H-thymidine incorporation was measured on day 3 of culture and the results representative of eight independent experiments are depicted in FIG. 3. The arithmetic mean (91,850±1300 (mean±SD)) CD28-induced T cell proliferation exhibits nearly complete cyclosporine resistance when accompanied by the administration of PMA. Table 6 below illustrates the effects of cyclosporine on CD3-induced proliferation of CD28$^+$ T cells cultured at approximately 5×10$^4$ cells/well in flat-bottomed 96-well microtiter plates (CoStar, Cambridge, Mass.) under the following conditions: immobilized Mab G19-4; or immobilized mAb G19-4 and mAb 9.30 100 ng/ml; or immobilized mAb G19-4 and PMA 1 ng/ml; or Mab 9.3 100 ng/ml and PMA 1 ng/ml. Cyclosporine was prepared as above and included in the cultures at 0, 0.2, 0.4, 0.8, 1.2 μg/ml.

$^3$H-thymidine incorporation was determined on day 3 of culture as above. The percent inhibition of proliferation was calculated between CD28$^+$ T cells cultured in medium only or in cyclosporine at 1.2 μg/ml. CD28$^+$ T cells cultured in the absence of cyclosporine were given cyclosporine diluent. $^3$H-thymidine incorporation of cells cultured in medium, or PMA, or monoclonal antibody 9.3 only were less than 150 cpm. As shown in Table 6, costimulation of CD3 and CD28 resulted in a marked increase in the resistance of T cell proliferation to cyclosporine and the stimulation of CD28 in the presence of PMA resulted in a complete absence of cyclosporine suppression of T cell proliferation. As shown in Table 7, stimulation of CD28 together with immobilized anti-CD3 also resulted in resistance to suppression of T cell proliferation by the immunosuppressant dexamethasone.

TABLE 7

Effects of CD28 Stimulation on Dexamethasone Resistance on T cell Proliferation
$^3$HTdR + Dexamethasone (Nm)

| STIMULUS | 0 | 25 | % INHIBIT |
|---|---|---|---|
| CD3 mAb G194 | 14,700 | 770 | 97 |
| CD3 mAb + IL-2 | 21,700 | 1,900 | 93 |
| CD28 mAb + PMA | 181,600 | 197,700 | <0 |
| PMA | 5,000 | 1,400 | 72 | supernatants were harvested at 24 h and serial dilutions assayed for IL-2, TNF-α/LT, IFN-γ, and GM-CSF as previously described. Separate aliquots of cells were recovered 48 h after stimulation and assayed for the percentage of cells in late stages of the cell cycle (S+G$_2$+M).

When cyclosporine at 0.6 μg/ml was included in the test protocol, as shown in Table 8 (which also incorporates the data of Specific Example IIII for comparison), CD28$^+$ T cells were found to secrete the T$_H$CD28 lymphokines in the presence of cyclosporine in cultures stimulated with mAb 9.3 and PMA; or immobilized mAb G19-4 and mAb 9.3; or PMA and ionomycin and mAb 9.3. T$_H$CD28 lymphokine production induced by immobilized mAb G19-4; or by PMA with ionomycin was, however, completely suppressed in the presence of cyclosporine.

TABLE 8

| STIMULUS | IL-2 (U/ml) | TNF-α/LT (U/ml) | IFN-γ (U/ml) | GM-CSF (U/ml) | S + G$_2$ + M (%) |
|---|---|---|---|---|---|
| Medium | <2 | 0 | 0 | 0 | 4.6 |
| PMA | <2 | 0 | 0 | NT | 5.5 |
| anti-CD28 | <2 | 5 | 0 | 0 | 6.5 |
| anti-CD28 + PMA | 435 | 300 | 24 | 150 | 48.9 |
| anti-CD28 + PMA + CSP | 192 | 200 | 12 | NT | 49.3 |
| anti-CD3$^i$ | 36 | 50 | 24 | 120 | 39.7 |
| anti-CD3$^i$ + CSP | <2 | 0 | 0 | NT | 14.5 |
| anti-CD3$^i$ + anti-CD28 | 1200 | 40 | 74 | 1050 | 44.7 |
| anti-CD3$^i$ + anti-CD28 + CSP | 154 | 200 | 9 | NT | 48.6 |
| Ionomycin | <2 | 0 | 0 | NT | 6.6 |
| Ionomycin + PMA | 200 | 5 | 37 | NT | 43.6 |
| Ionomycin + PMA + CSP | <2 | 0 | 0 | NT | 8.1 |
| Ionomycin + PMA + anti-CD28 | 1640 | 320 | 128 | NT | 43.5 |
| Ionomycin + PMA + anti-CD28 + CSP | 232 | 120 | 15 | NT | 47.6 |

$^i$ = immobilized
NT = not tested

SPECIFIC EXAMPLE VIII

Human T$_H$CD28 Lymphokine mRNA Expression in the Presence of Cyclosporine

In order to further examine whether CD28 stimulation led to cyclosporine-resistant T$_H$CD28 lymphokine gene expres-

TABLE 6

Effects of CD28 Stimulation on Cyclosporine Resistance on T Cell Proliferation
Mean [$^3$H]thymidine incorporation (kcpm) ± 1 SD at Cyclosporine Conc (ug/ml)

| STIMULUS | 0 | 0.2 | 0.4 | 0.8 | 1.2 | % INHIBIT |
|---|---|---|---|---|---|---|
| CD3 mAb G19-4 | 77 ± 26 | 61 ± 6.8 | 52 ± 4.4 | 10 ± 3.4 | 8.2 ± 1.2 | 90 |
| CD3 + CD28 mAb 9.3 | 123 ± 18 | 86 ± 2.3 | 63 ± 4.4 | 44 ± 6.4 | 43 ± 5.2 | 65 |
| CD3 + PMA | 145 ± 12 | 132 ± 2.8 | 123 ± 6.4 | 55 ± 3.6 | 56 ± 6.4 | 62 |
| CD28 mAb 9.3 + PMA | 111 ± 12 | 97 ± 5.6 | 107 ± 12 | 99 ± 14 | 112 ± 2.4 | <0 |

SPECIFIC EXAMPLE VII

Human T$_H$CD28 Lymphokine Secretion in the Presence of Cyclosporine.

As described in Specific Example III, CD28$^+$ T cells were cultured in the presence of various stimulators. Culture sion as well as secretion, the ability of cyclosporine to suppress induction of IL-2, TNF-α, LT, IFN-γ, and GM-CSF following stimulation by various stimulators was tested. Specifically, CD28$^+$ T cells were cultured at 2×10$^6$/ml in complete RPM1 medium (GIBCO, Grand Island, N.Y.) with 5% FCS (MED). Individual aliquots of CD28$^+$ T cells were incubated for 6 h in the presence or absence of 1.0 µg/ml cyclosporine with PMA 3ng/ml and anti-CD28 mAb 9.3 (1 mg/ml); or with immobilized anti-CD3 mAb G19-4 (1 µg/well); or with immobilized mAb G19-4 (1 µg/well) and mAb 9.3 (1 ng/ml). CD28+ T cells were harvested, total cellular RNA isolated and equalized for ribosomal RNA as previously described by Thompson, et al., *Nature*, 314:363–366 (1985).

Northern blots were prepared and hybridized sequentially with $^{32}$P-labeled, nick-translated gene specific probes as described by June, C. H. et al., *Mol. Cell. Biol.*, 7:4472–4481 (1987). The IL-2 probe was a 1.0 kb Pst I cDNA fragment as described by June, C. H. et al., *Mol. Cell. Biol.*, 7:4472–4481 (1987); the IFN-γ probe was a 1.0 kb Pst I cDNA fragment as described by Young, et al., *J. Immunol.*, 136:4700–4703 (1986). The GM-CSF probe was a 700 base pair EcoR I-Hind III cDNA fragment as described by Wong, et al., *Science*, 228:810–815 (1985); the 4F2 probe was a 1.85 kb EcoR I cDNA fragment as described by Lindsten, et al., *Mol. Cell. Biol.*, 8:3820–3826 (1988); the IL4 probe was a 0.9 kb Xho I cDNA fragment as described by Yokota, et al., *PNAS (USA)*, 83:5894–5898 (1986); and the human leukocyte antigen (HLA) probe was a 1.4 kb Pst I fragment from the HLA-B7 gene as described by Lindsten, et al., *Mol. Cell. Biol.*, 8:3820–3826 (1988). TNF-α and LT specific probes were synthesized as gene-specific 30 nucleotide oligomers as described by Steffen, et al., *J. Immunol.*, 140:2621–2624 (1988) and Wang, et al., *Science*, 228:149–154 (1985). Following hybridization, blots were washed and exposed to autoradiography at −70° C.

Quantitation of band densities was performed by densitometry as described in Lindsten, et al., *Mol. Cell. Biol.*, 8:3820–3826 (1988).

Figure 4:
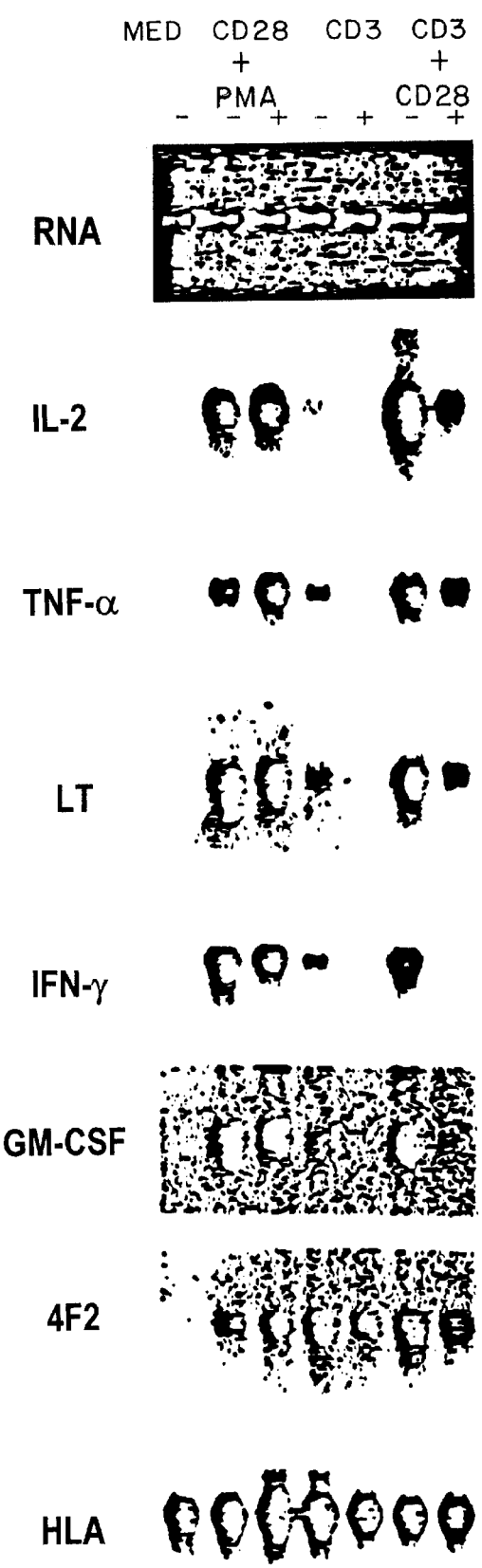
FIG. 4 is a Northern blot analysis of the effects of cyclosporine on PMA-or anti-CD3 activated T cell lymphokine expression induced by anti-CD28.

As illustrated by the Northern blot of FIG. 4, stimulation by mAb 9.3 with PMA and by mAb 9.3 with mAb G19-4 led to human $T_H$CD28 lymphokine gene expression that exhibited resistance to cyclosporine. In contrast, stimulation by TCR/CD3 mAb G19-4 alone was completely suppressed in the presence of cyclosporine.

SPECIFIC EXAMPLE IX

In Vivo Activation of T Cells by CD28 Stimulation
A. Monoclonal Antibody 9.3 F(ab')$_2$.

F(ab')$_2$ fragments of mAb 9.3 were prepared as described by Ledbetter, J. A. et al., *J. Immunol.*, 135:2331–2336 (1985). Purified and endotoxin-free F(ab')$_2$ fragments were injected intravenously at 1 mg/kg of body weight over a 30 minute period into a healthy macaque (*M. nemestrina*) monkey. On days 2 and 7 after injection, 5 ml of blood was drawn and tested.

Figure 5:
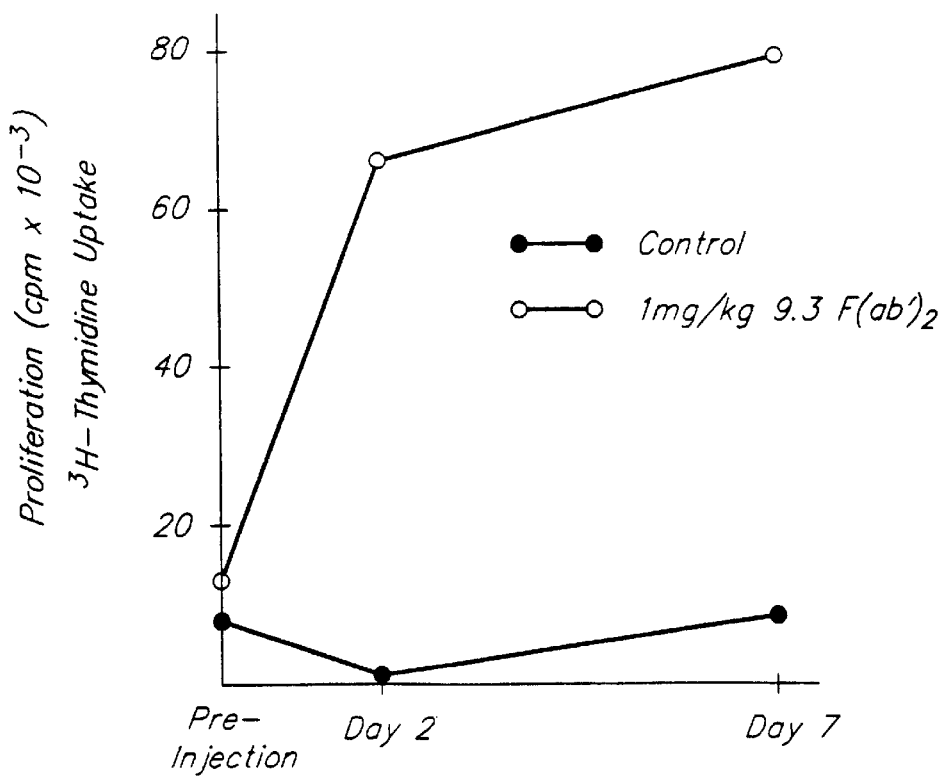
FIG. 5 is a graph illustrating in vivo activation of T cells in monkeys by CD28 stimulation.

Peripheral blood lymphocytes from the monkey's blood were isolated by density gradient centrifugation as described in Specific Example II. Proliferation of peripheral blood mononuclear cells in response to PMA (1 ng/ml) was tested in the treated monkey and a control animal (no F(ab')$_2$ fragment treatment) in triplicate as described in Specific Example IV. Proliferation was measured by the uptake of $^3$H-thymidine during the last 6 h of a three-day experiment and the results shown in FIG. 5. Means of triplicate culture are shown, and standard errors of the mean were less than 20% at each point. As shown in FIG. 5, in vivo stimulation of CD28 by the F(ab')$_2$ mAb 9.3 fragment increased T cell proliferation for at least 7 days.
B. Monoclonal Antibody 9.3

Two doses of mAb 9.3, 10 mg and 0.1 mg, were administered intravenously to primates Macaca mulatta. The antibody wa infused intravenously immediately after baseline (time zero) blod valves were obtained. Three animals were evaluated as described below at each dose.

Figure 6A:
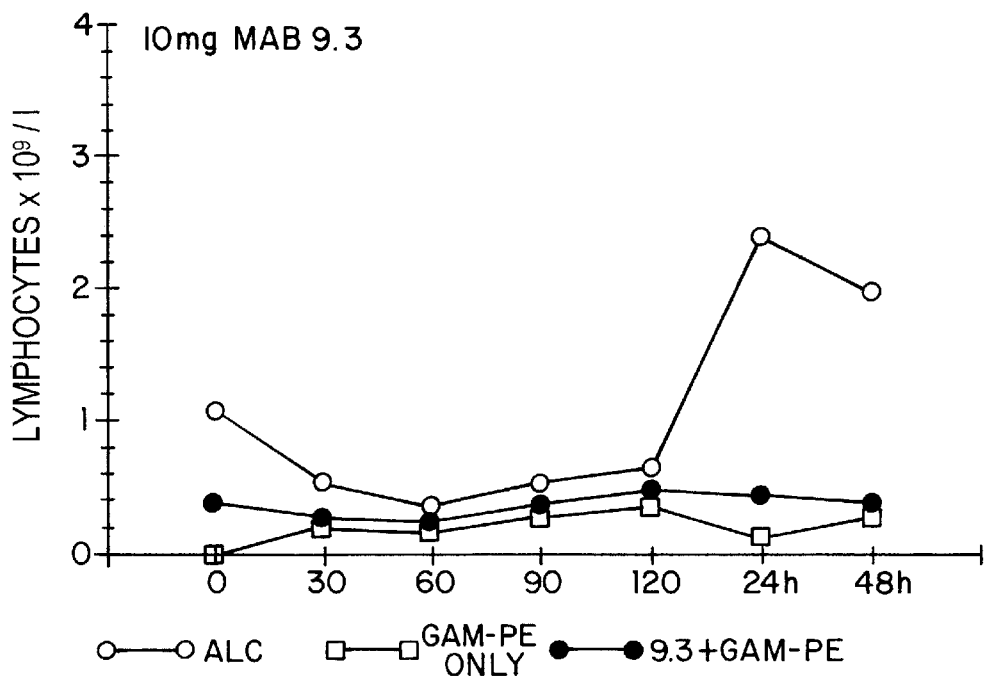
FIGS. 6A and 6B are graphs representing changes in lymphocyte levels after infusion of anti-CD28 Mab.
Figure 6B:
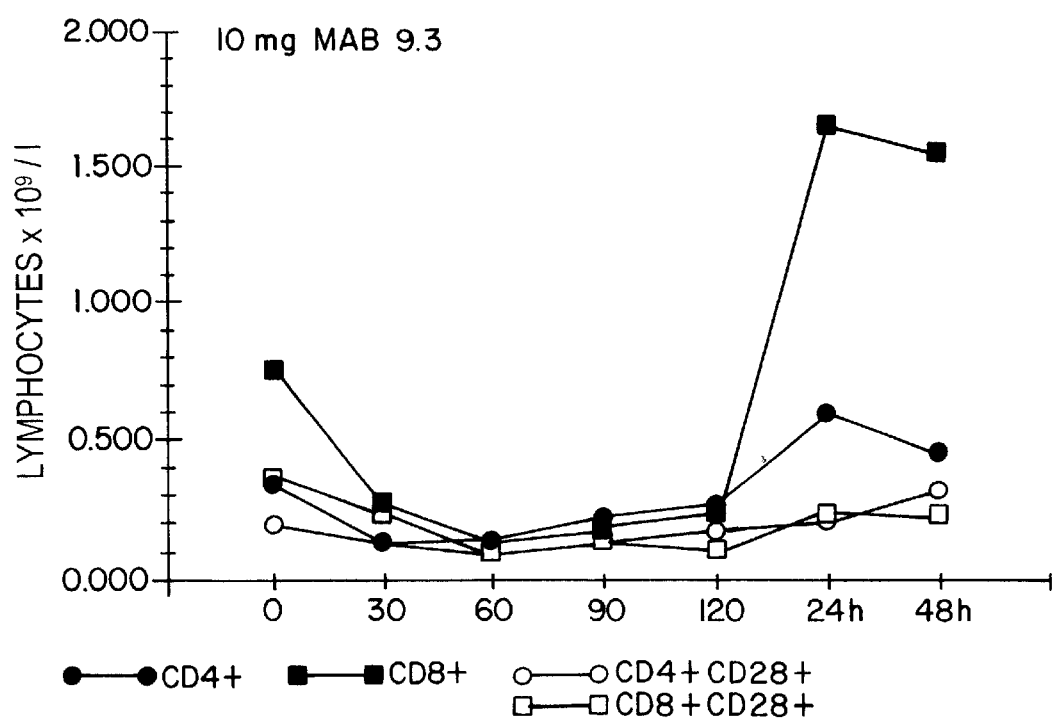

Cell population changes. At the higher dose, immediate effects were monitored over the first 120 m. In FIGS. 6A and 6B, a representative result is depicted showing the change in the lymphocyte counts over time. The ALC and distribution of CD28+ cells are depicted in FIG. 6A, while FIG. 6B illustrates the absolute numbers of CD4+ and CD8+ cells. The absolute lymphocyte count (ALC) decreased over the first 60 m and then increased above baseline at 24 h (see FIG. 6A). In this case, the number of circulating CD28 positive lymphocytes remained essentially the same, as determined by adding goat anti-mouse phycoerythrin (GAM-PE) only or mAb 9.3 plus GAM-PE. In this same animal, the CD4 and CD8 positive populations were followed and the increase at 24 h was the result of an increase in CD8+ CD28− cells (see FIG. 6B). Animals re-evaluated after 8 days had between 35 to 60% of the CD28+ cells coated with antibody. There was no significant change in the circulating lymphocyte counts in primates treated with 0.1 mg mAb 9.3.

Figure 7A:
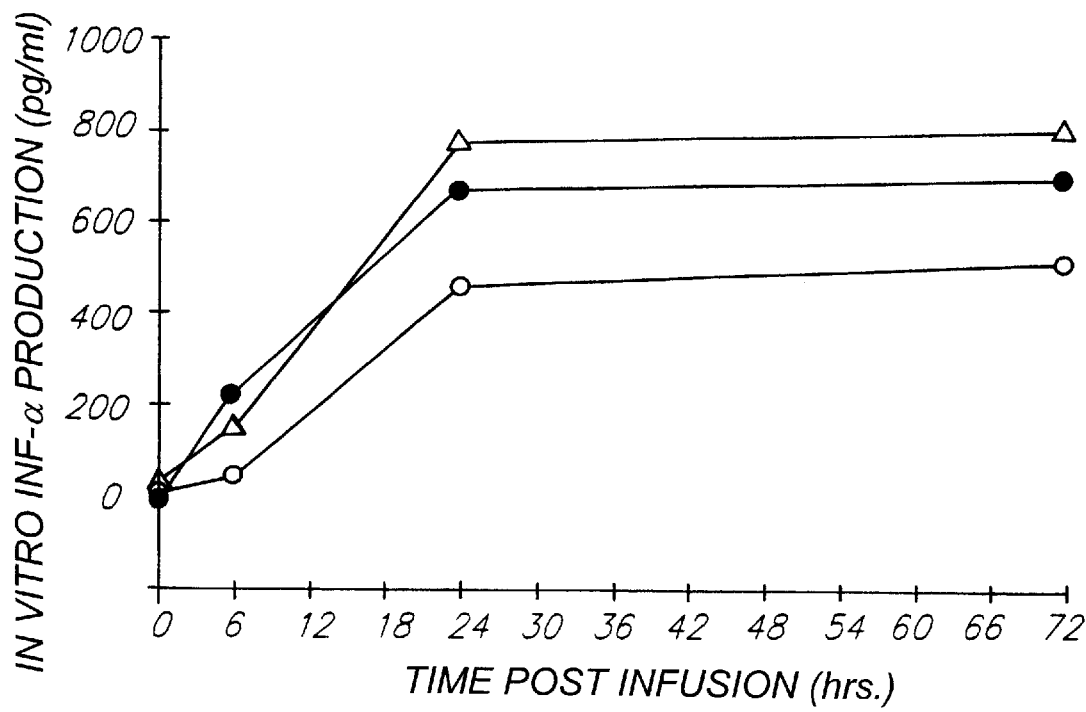
FIGS. 7A and 7B are graphs representing in vitro production of TNF and IL-6 by PBLs under various conditions.
Figure 7B:
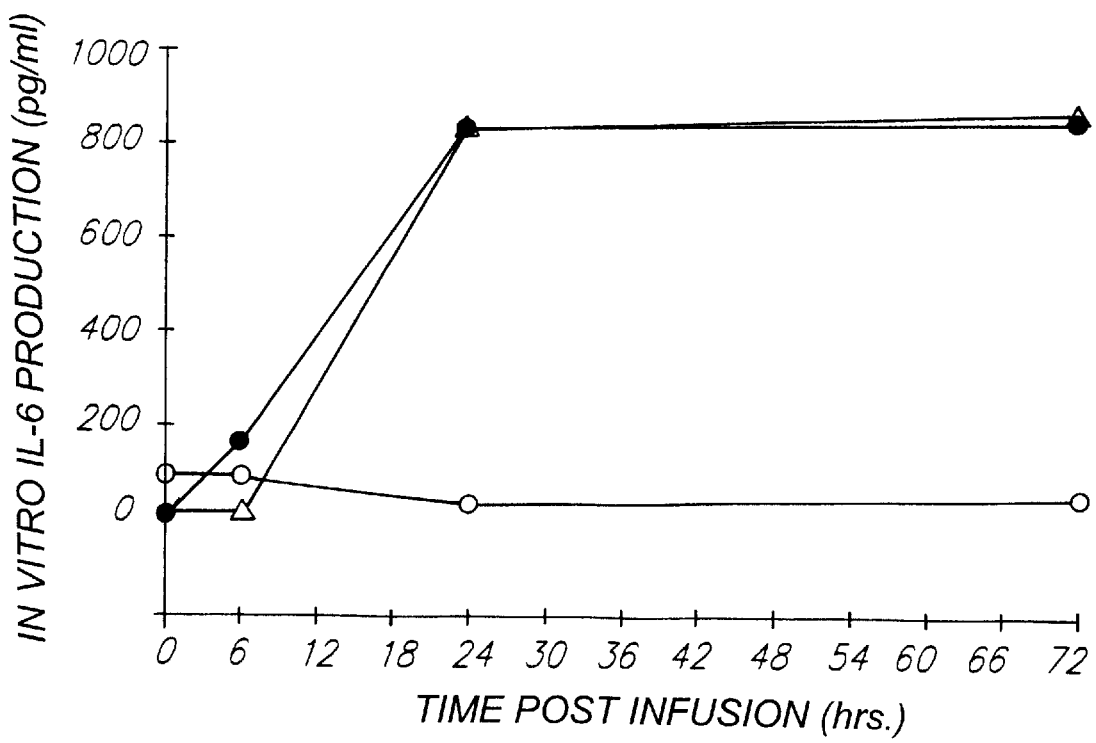

Cytokine released after in vitro stimulation. PBLs isolated at specific time points from primates previously immunized with tetanus toxoid and treated with 10 mg mAb 9.3 were cultured in vitro to determine the effect of antigenic stimulation on cytokine production. FIG. 7A represents the in vitro production of TNF while FIG. 7B represents the in vitro production of IL-6. PBLs stimulated with Concanavalin-a (Con-a) are depicted by Δ. PBLs stimulated with tetanus toxoid (TT) are depicted by ●. Unstimulated PBLs are depicted by ○. As shown in FIGS. 7A and 7B, cultures of baseline cells did not respond to either Con-a or TT stimulation. However, as shown in FIG. 7A, PBLs isolated from animals 6 h after infusion of antibody showed an increase in TNF production. As depicted in FIG. 7B, after 24 h, unstimulated cultures produced TNF but not IL-6. TT stimulation of PBLs produced a similar quantity of both TNF and IL-6 as mitogen stimulated cultures. This response was consistent through 72 h.

Monoclonal antibody 9.3 was administered to the primates either as a single day bolus of 10 mg (n=3) or as multiple daily injections of 10 mg/d for 5 consecutive days (n=3) and the animals were followed simultaneously. The changes in the peripheral blood cell populations were not dramatic. ALC as previously observed decreased with the first injection but recovered to above baseline if no further injections were administered. However, for animals treated with multiple injections, ALC remained ~25% below normal during the period of mAb administration. ALC in multiple-treated animals did not recover to above normal levels over the 21-day study period. Absolute neutrophil count decreased by ~30% in the 5 day treated group.

Figure 8A:
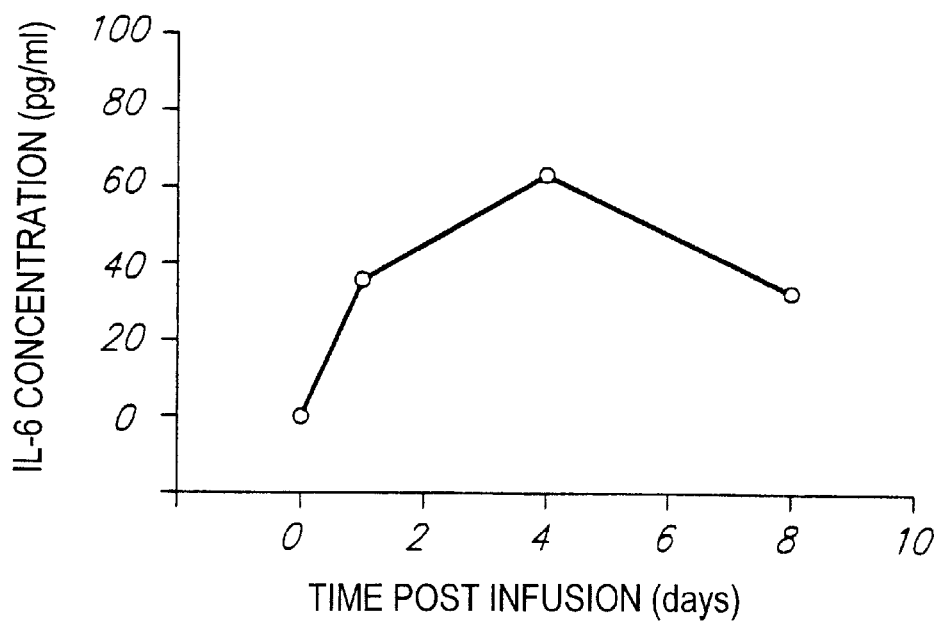
FIGS. 8A and 8B are graphs representing serum concentration of IL-1β after single and multiple doses of anti-CD28 Mab.
Figure 8B:
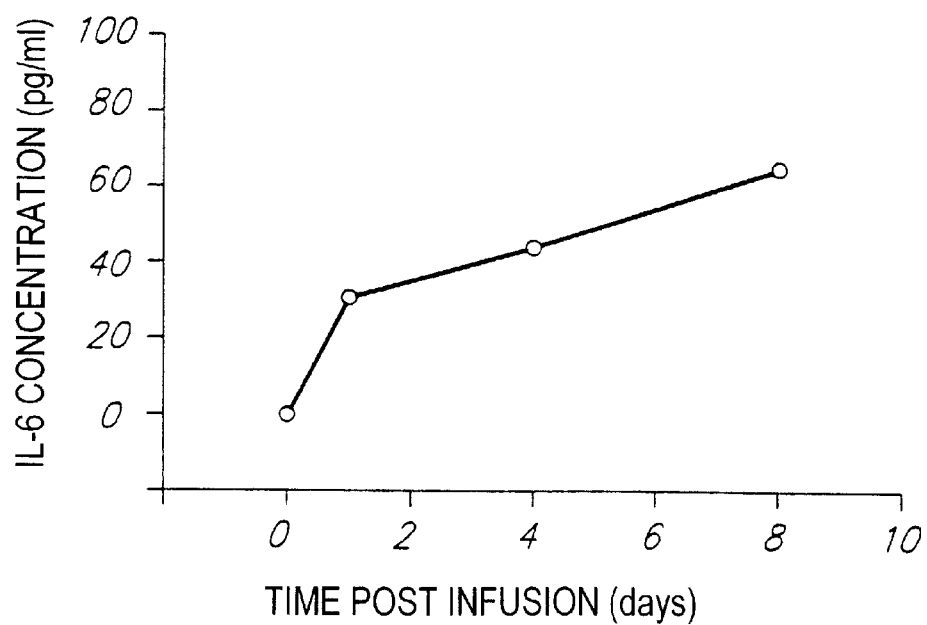

Cytokine levels in serum. Serum was analyzed for IL-6, TNF, and IL-1β. The detection of TNF from the serum preparations was not successful and therefore no results are available at this time. FIGS. 8A and 8B demonstrate the serum concentration of IL-6 after infusion of mAb 9.3. As shown in FIGS. 8A and 8B, increased IL-6 levels 24 h after mAb infusion were detected. In animals injected one time, the IL-6 levels increased to a peak on day 4, but a decrease was observed when remeasured on day 8 (see FIG. 8A). In comparison, 5 day treated animals (multiple doses) demonstrated continual increase(s) in IL-6 through day 8 (see FIG. 8B).

Figure 9A:
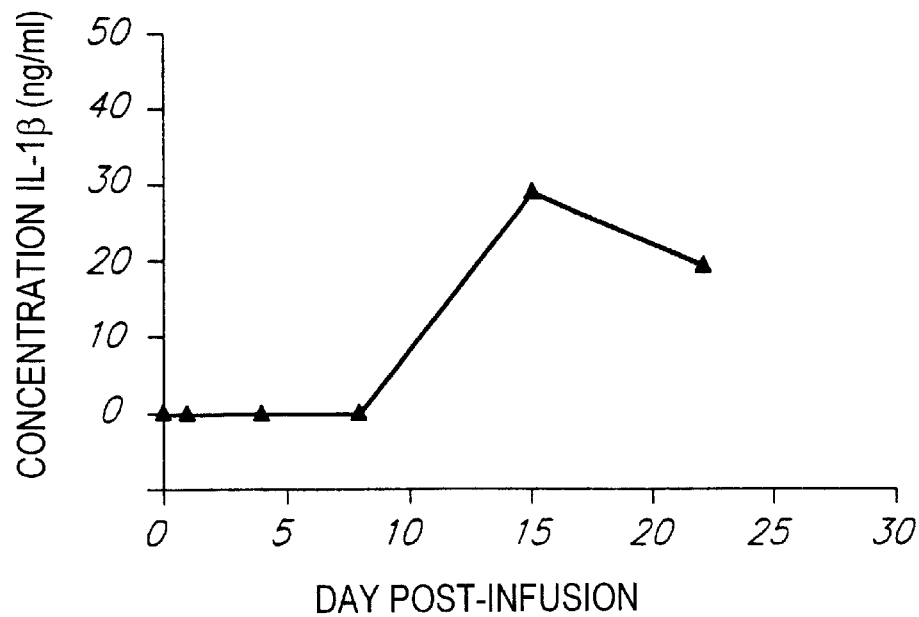
FIGS. 9A and 9B are graphs representing the serum concentration of IL-6 after single and multiple doses of anti-CD28 Mab.
Figure 9B:
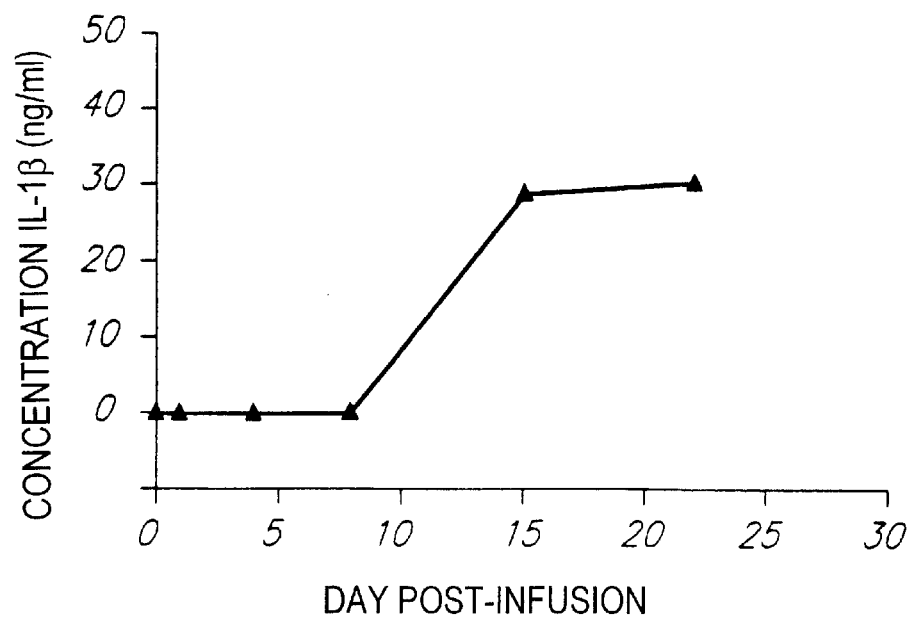

FIGS. 9A and 9B demonstrate the serum concentration of IL-1 after infusion of mAb 9.3. As shown in FIGS. 9A and 9B, measurements of IL-1β in the serum, did not detect any IL-1 until after day 8 in single injected animals (see FIG. 9A) or multiple injected animals (see FIG. 9A). The multiple injected animals, however, had increasing levels of IL-1β at day 21 post-infusion, while single injected animals had decreasing levels at this time.

Cytokine release after in vitro stimulation. IL-6 production was not detected in the PBLs of animals on day 3 after in vitro stimulation with TT. (FIG. 10). This finding contrasted with the previous in vitro results. However, an increased production of IL-6 was detected on day 7 and the more significant increase was observed from PBLs isolated from the 5 day treated primates. This increase in production was further observed in culture of PBLs isolated on day 14.

Figure 10A:
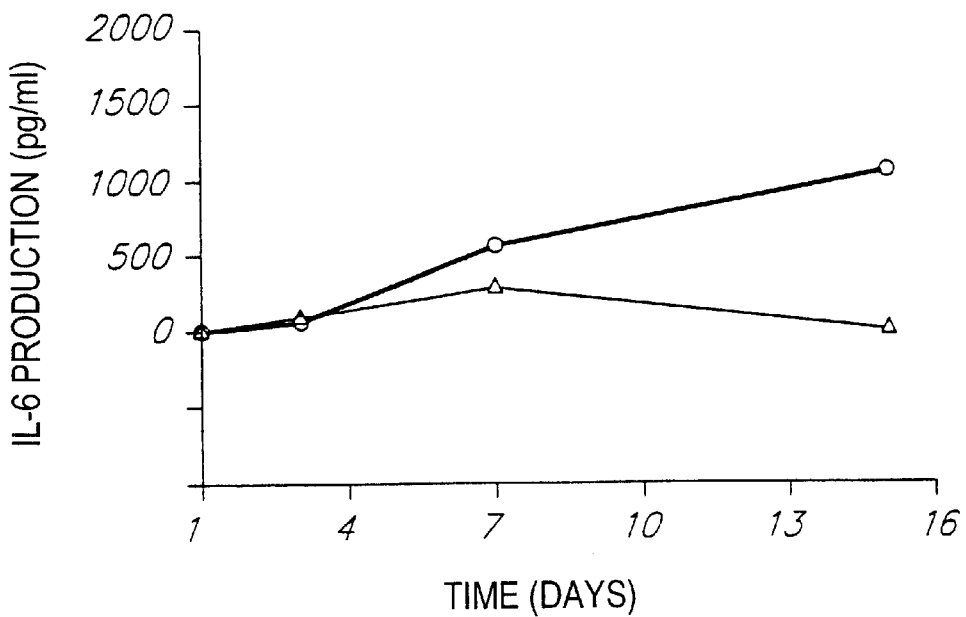
FIGS. 10A and 10B are graphs representing IL-6 production of in vitro stimulated PBLs isolated from monkeys treated with a single bolus or multiple injections of anti-CD28 Mab.
Figure 10B:
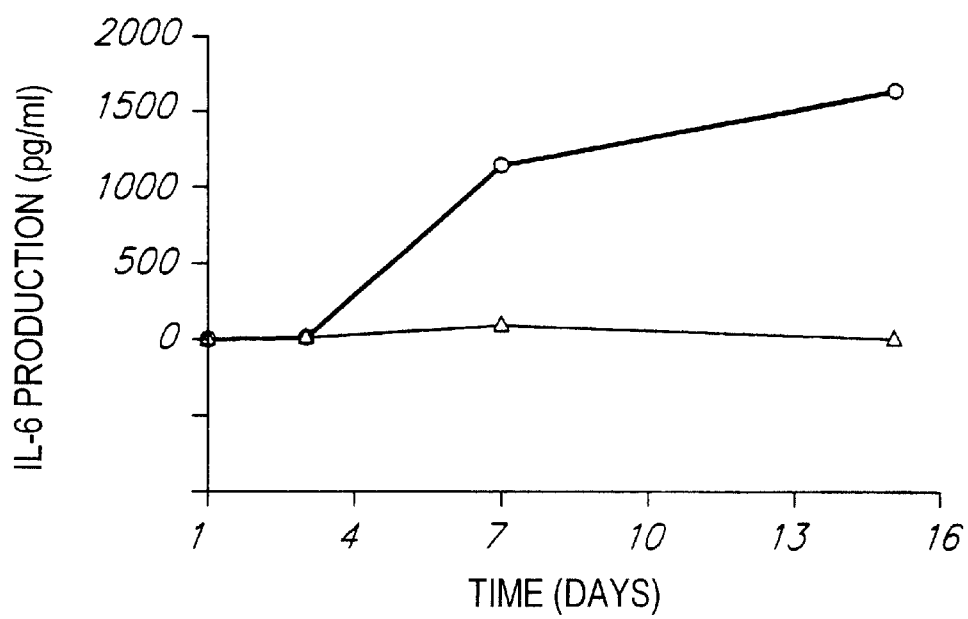

IL-6 Production and Proliferation of PBLS. FIGS. 10A and 10B illustrate IL-6 production of in vitro stimulated PBLs isolated from monkeys. Days 1, 3 and 14 are depicted in FIGS. 10A and 10B with Δ representing the control and O representing the stimulated PBL response. FIG. 10A illustrates the response of a single injected animal and FIG. 10B illustrates the response of a multiple injected animal. (Note that the quantity of cells harvested from PBL limited the number of assays performed, resulting in no day zero points and no day zero data.) PBLs were isolated from the different treated groups and evaluated for their proliferative response to Con-A, TT or no stimulus. Historically the TT response was ~5,000 cpm and the baseline Con-A response was ~35,000 cpm. The PBL proliferative response to Con-A was reduced by about 80% and gradually recovered over time (not shown). No proliferative response was observed when the PBL were stimulated with TT. This contrasts with the lymphokine production observed in in vitro cultures.

SPECIFIC EXAMPLE X

Immunoregulation with CTLA-4Ig

A. In Vitro.

The effects of CTLA-4Ig on the primary immune response to alloantigen was initially examined in a one-way mixed lymphocyte culture (MLC) between Lewis rats (RT1$^l$, responder) and Brown-Norway rats (RT1$^n$, stimulator). Lymphocytes were isolated from paratracheal and cervical lymph nodes. Cultures were performed in quadruplicate in 96-well round bottomed plates as described in Turka, L. A. et al., *Transplant.*, 47:388–390 (1989). Cultures were harvested after 4 days and 1 mCi/well of $^3$H-thymidine was added for the last 6 h of culture. In this assay, Brown-Norway stimulator cells were irradiated at 30 Gy to prevent their proliferation, and then added to cultures of Lewis responder lymphocytes. A proliferative response will normally occur in approximately 1–5% of cells as a result of activation through their cell-surface TCR in response to allogeneic MHC as discussed in Marrack, P. et al., *Immunol. Today*, 9:308–315 (1988). Graded concentrations of CTLA-4Ig or an isotype-matched control monoclonal antibody L6 described in Fell, H. P. et al., *J. Bio. Chem.* (in press), was added to the cultures.

Figure 11:
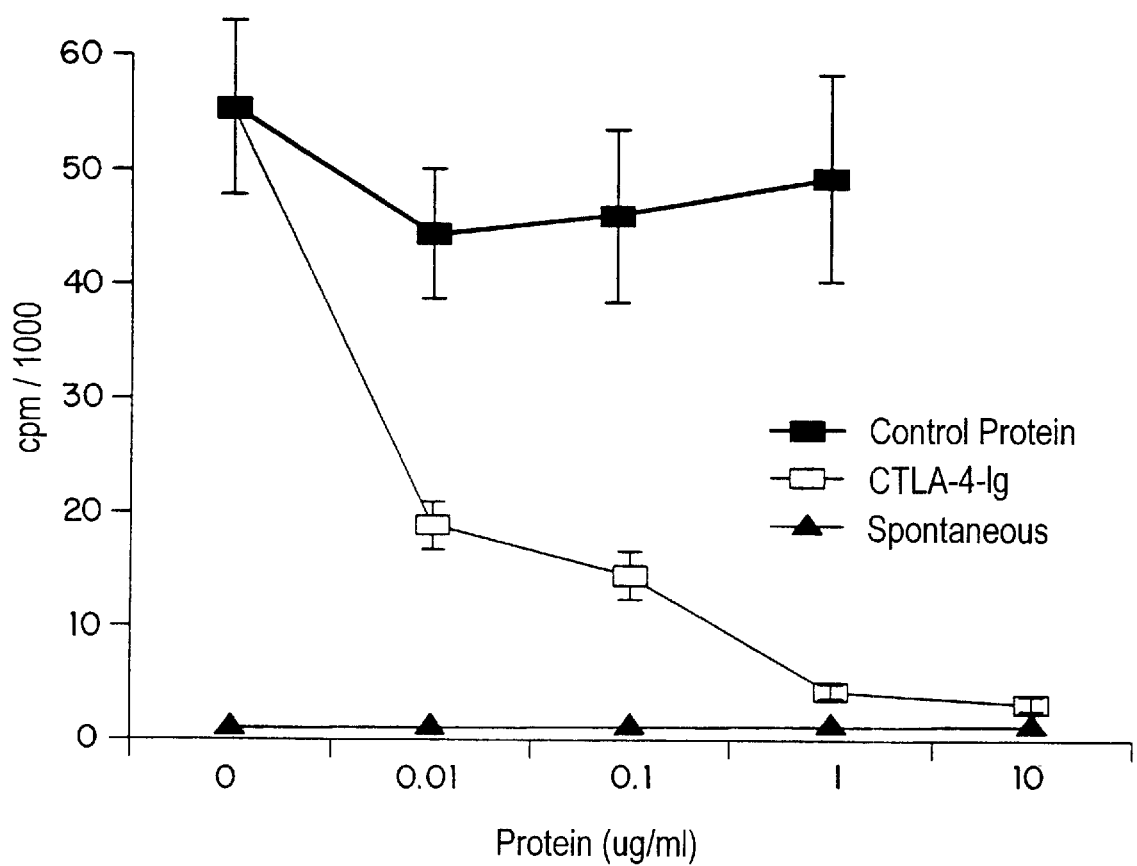
FIG. 11 is a graph representing the inhibitory effect of CTLA-4Ig on $^3$H-thymidine incorporation in a one-way mixed lymphocyte culture.

FIG. 11 represents the effect of CTLA-4Ig on a one-way mixed lymphocyte culture. Spontaneous proliferation is the incorporation of thymidine by Lewis cells in the absence of Brown-Norway stimulators, and is depicted by closed triangles in FIG. 11. As shown in FIG. 11, CTLA-4Ig was able to block proliferation in a dose dependent fashion with virtually complete inhibition observed at a concentration of 1 mg/ml. (Results are expressed as counts per minute of $^3$H-thymidine incorporation ±standard deviation). Consistent with these results, alloreactive T cell responses can also be inhibited by non-stimulatory Fab fragments of an anti-CD28 monoclonal antibody as shown in Azuma, M. et al., *J. Exp. Med.*, 175:353–360 (1992). Together, these data suggest that in order to mount a proliferative response in vitro, alloreactive T cells must be stimulated not only through MHC engagement of the TCR but also require costimulation by B7 engagement of the CD28 receptor.

B. In Vivo: Cardiac Allografts.

CTLA-4Ig was next used in a rat model of organ transplantation to ascertain its ability to block alloantigen responses in vivo. Recipient animals received a heterotopic cardiac allograft which was anastomosed to vessels in the neck as described in Bolling, S. F. et al., *Transplant.*, 53:283–286 (1992). Grafts were monitored for mechanical function by palpation and for electrophysiologic function by electrocardiogram. Graft rejection was said to occur on the last day of palpable contractile function. As an initial test, animals were treated with daily injections of CTLA-4Ig or an isotype-matched negative control monoclonal antibody L6 for 7 days. CTLA-4Ig was administered at doses of 0.015 mg/day (5 animals), 0.05 mg/day (5 animals), and 0.5 mg/day (8 animals). L6 was given at 0.5 mg/day. Untreated Lewis rats rejected the heterotopic Brown-Norway allografts in 6.8±0.3 days (n=10). The allografts in CTLA-4Ig-treated animals remained functional following completion of drug administration, whereas untreated animals, or animals treated with the L6 control antibody, uniformly rejected their grafts by day 8 (p<0.0001) as shown in Table 9. (p values were calculated by Chi-square analysis).

TABLE 9

| GRAFT SURVIVAL DAY 8 | | SIGNIFICANCE |
|---|---|---|
| Untreated | 0/10 | p < 0.0001 |
| CTLA-4Ig | 18/18 | p < 0.0001 |
| Control Protein | 0/5 | |

CTLA-4Ig-treated rats manifested no observable acute or chronic side effects from administration of the protein. No gross anatomic abnormalities were observed in CTLA-4Ig-treated animals at autopsy.

Figure 12A:
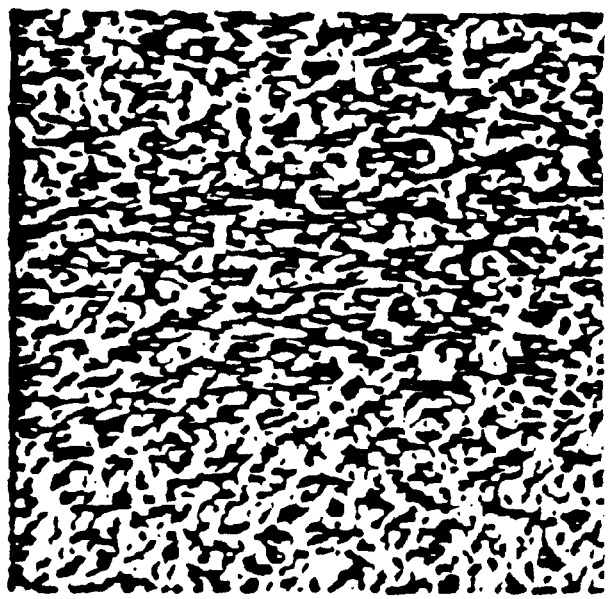
FIGS. 12A and 12B are photographs of cardiac allografts to illustrate histopathology.
Figure 12B:
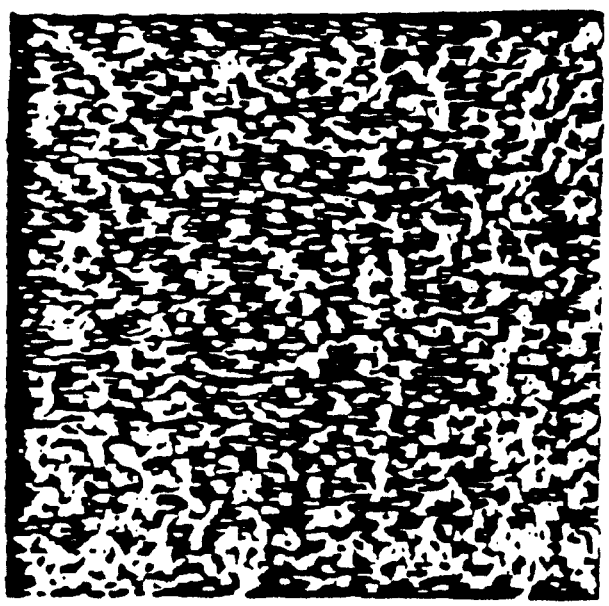

An untreated animal and a CTLA-4Ig-treated animal were sacrificed for histological examination. Cardiac allografts were removed from an untreated animal (shown in FIG. 12A) and a CTLA-4Ig-treated animal (0.5 mg/day) (shown in FIG. 12B) four days after transplantation. Allografts were fixed in formalin, and tissue sections were stained with hematoxylin-eosin. (Original photography at 200× magnification.) The donor heart removed from the untreated animal showed histological findings of severe acute cellular rejection, including a prominent interstitial mononuclear cell infiltrate with edema formation, myocyte destruction, and infiltration of arteriolar walls. In contrast, the transplanted heart from the CTLA-4Ig-treated animal revealed only a mild lymphoid infiltrate. Frank myocyte necrosis and evidence of arteriolar involvement were absent. The native heart from each animal showed no histological abnormalities.

To determine whether CTLA-4Ig therapy established a state of graft tolerance that persisted following drug treatment, animals treated for 7 days with daily injections of CTLA-4Ig were observed without additional therapy until cessation of graft function.

Figure 13:
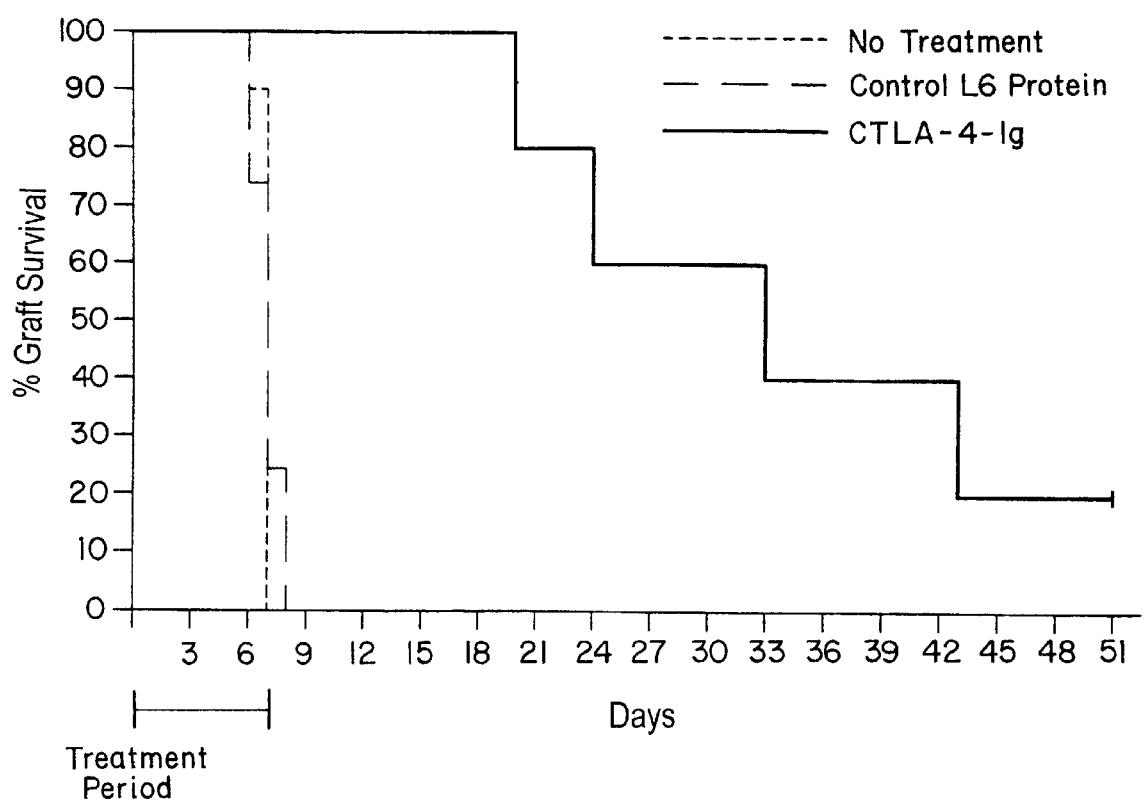
FIG. 13 is a Kaplan-Meier life analysis of cardiac allograft survival after CTLA-4Ig treatment.

Animals received either no treatment, CTLA-4Ig (0.5 mg/day×7 days), or an isotype-matched control monoclonal antibody, L6 (0.5 mg/day×7 days). In all cases treatment was initiated at the time of transplantation. FIG. 13 is a graph showing allograft survival in the treated and control rats.

Graft survival was 18–40 days in animals treated with 0.05 mg/day of CTLA-4Ig. Graft survival was assessed daily. This failure to induce permanent engraftment did not appear to be due to inadequate dosing of CTLA-4Ig, as animals treated with a ten-fold higher dose, 0.5 mg/day, showed a similar graft survival curve as depicted in FIG. 13, with one animal maintaining long-term graft function (>50 days). In FIG. 13, graft survival is displayed as the last day of graft function. Animals treated with a dose of 0.015 mg/day×7 days (n=5) had a mean survival of 12.6±2.1 days (n=5). Furthermore, serum CTLA-4Ig trough levels in this group as measured in a quantitative ELISA assay were in excess of 10 μg/ml, a concentration which is maximally suppressive in vitro (see FIG. 11). Histological examination of the allografts from CTLA-4Ig-treated animals whose grafts ceased functioning after 18–43 days displayed typical signs of acute cellular rejection, of the same degree of severity as seen in control animals that had rejected their hearts after 7 days. The animal with continued graft function was sacrificed on day 57, and the allograft from this animal failed to reveal any histological abnormalities.

At the time of sacrifice, lymphocytes from the day 57 "tolerant" animal, and from a CTLA-4Ig-treated animal that rejected the heart at day 33, were tested for their functional responses. These responses were compared with those of lymphocytes from a control (non-transplanted) Lewis rat, and results were normalized as a percentage of the control response. In comparison to control animals, lymphocytes from both the "tolerant" and rejecting animal had equivalent proliferative responses to Con-a, (tolerant, 62.5%; rejecting, 51.1%; p=0.63, two-tailed T test) and to cells from a third party ACI rat ($RT1^{avl}$) (tolerant, 160%; rejecting, 213%; p=0.58). However a significant disparity was seen in the response to Brown-Norway cells (tolerant, 34.2%; rejecting, 238%; p<0.005), suggesting that T cells from animals with functioning grafts were specifically hyporesponsive to donor MHC antigens. The thymus and spleen from the day 57 "tolerant" animal were similar in size and cell number to the non-transplanted control rat, and flow cytometric analyses of thymus, lymph nodes and spleen revealed similar percentages of both $CD4^+$ and $CD8^+$ T cells in each animal. Splenocytes adoptively transferred from the day 57 "tolerant" animal into a native Lewis recipient failed to affect the rate at which that animal rejected a Brown-Norway cardiac allograft. Thus, tolerance did not appear to be maintained by suppressor cells in this animal.

The fact that 4 of 5 allograft recipients treated with high dose CTLA-4Ig (0.5 mg/day×7 days) rejected their grafts within the study period indicated that blockade of the costimulatory molecule B7 did not consistently induce permanent graft tolerance. One possible explanation was that CTLA-4Ig induced a temporary state of non-responsiveness, and that upon recovery, recipient T cells could effect graft rejection. Alternatively, CTLA-4Ig treatment may have resulted in a state of permanent non-responsiveness in circulating T cells by allowing target antigen recognition without B7-dependent costimulation. Newly matured T cells emerging from the thymus after cessation of CTLA-4Ig treatment could not be tolerized by this mechanism, and could mediate graft rejection as a result of B7-costimulated T cell alloreactivity. To differentiate between these two possibilities, rats were thymectomized 3 days prior to cardiac transplantation, and treated with daily injection of CTLA-4Ig (0.5 mg/day×7 days) following transplantation. These animals rejected their grafts between days 28 and 33, indicating that allograft recipients were not dependent upon the influx of new T cells to initiate an alloimmune response. Thus, it appears that T cells present during the time of CTLA-4Ig treatment can eventually induce graft rejection. This may represent T cell recovery from a temporary state of non-responsiveness, or may reflect the kinetics of T cell trafficking during the CTLA-4Ig treatment period.

C. Synergistic effects with cyclosporine.

Figure 14:
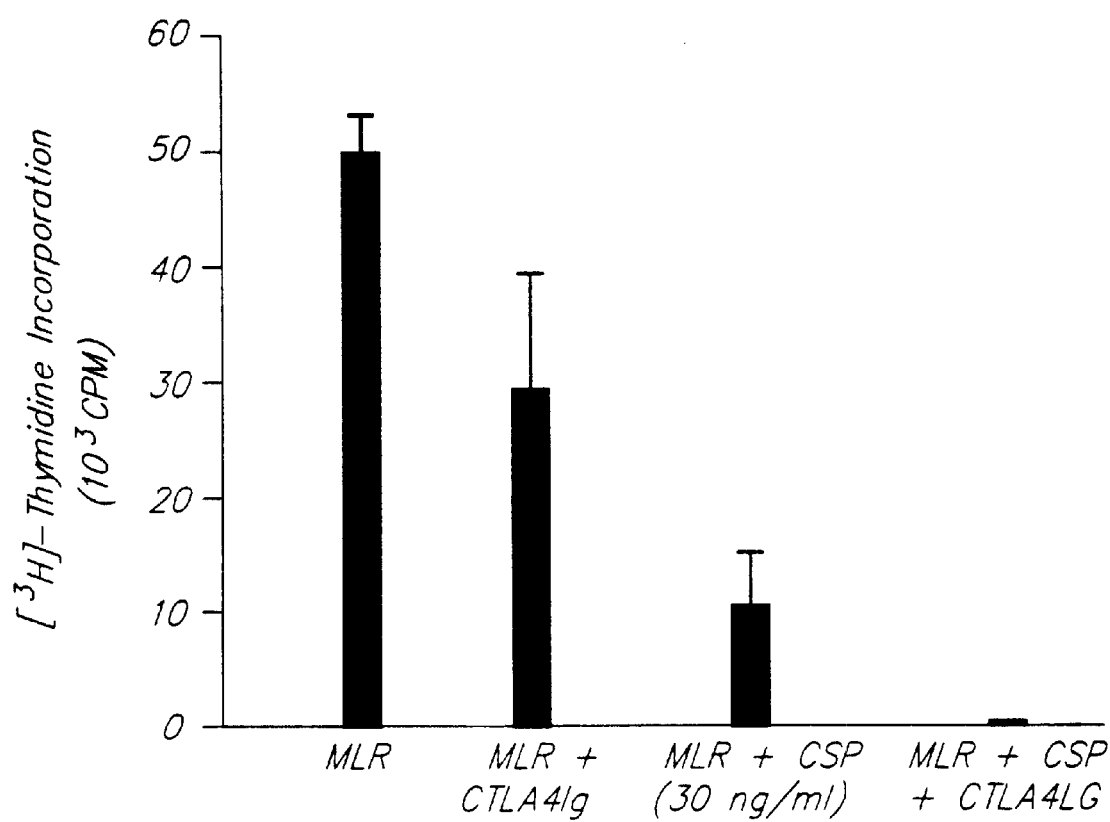
FIG. 14 is a bar graph illustrating CTLA-4Ig and cyclosporine as synergistic immunosuppressants.

Based on the ability to show that a soluble CD28 receptor homologue, CTLA-4Ig, is capable of suppressing cell-mediated responses in vitro and in vivo, experimentation was performed to determine whether or not this immunosuppressant has additive or synergistic effect with cyclosporine. A mixed lymphocyte reaction (MLR) with Brown-Norway rat lymph node cells as stimulators and Lewis strain rat lymph node cells as responders was measured by measuring tritiated thymidine incorporation 72 h after cocultivation. The ability of CTLA-4Ig at a concentration of 0.1 μg/ml and cyclosporine at 30 ng/ml alone or in combination was measured. FIG. 14 shows $^3$H-thymidine incorporation under various conditions. As can be seen in FIG. 14, although either immunosuppressant led to only a partial reduction in the mixed lymphocyte proliferative response (MLR+CTLA-4Ig and MLR+CSP), the combination of the two (MLR+CSP+CTLA-4Ig) completely blocked the mixed lymphocyte reaction between these MHC-incompatible strains. This effect is greater than what would be expected from two immunosuppressive reagents which have additive effects, suggesting that CTLA-4Ig and cyclosporine block T cell activation by independent mechanisms and have a synergistic effect on T cell activation in response to alloantigens.

SPECIFIC EXAMPLE XI

Control of Lymphokine Production by Second Messengers

A variety of second messengers in the regulation of lymphokine production were examined. In particular, a role for the two primary cell secondary messenger systems, the activation of protein kinase C and elevation in intracellular calcium, were characterized as being central regulators of the transcription of lymphokine genes. In addition, specific tyrosine phosphorylation events were identified that may correlate with the generation of alterations in translation and/or MRNA stability. Further investigations into serine and threonine kinases indicate that they may also have a role in the signal transduction events involved in lymphokine production. In contrast, experiments into the regulation by cGMP showed that this agent has relatively non-specific effects on lymphokine production.

Tyrosine phosphorylation events related to CD28 were further studied as described below.

Protocol

Monoclonal antibodies. Anti-CD2 mAb G19-4 (lgG1), anti-CD28 mAb 9.3 (lgG2a), anti-CD5 mAb 10.2 (lgG2a), and anti-CD45 mAb 9.4 (lgG2a) were produced, purified and in some cases, biotinylated as described in Ledbetter, J. A. et al., *J. Immunol.*, 135:2331 (1985) and Ledbetter, J. A. et al., i J. Immunol., 137:3299 (1986). Anti-B7 mAb 133 (lgM) and dilutions of ascites as described in Freedman, A. S. et al., *J. Immunol.*, 139:3260 (1987), were used. Anti-CD3 mAb OKT3 (lgG2a) was absorbed to goat anti-mouse lgG covalently linked to microspheres (KPL, Gaithersburg, Md.), by incubation of a 1/$10^5$ dilution of pooled ascites with $10^7$ beads/ml in HBSS at room temperature, followed by extensive washing.

Cells. The $CD28^+$ subset of T cells was isolated from peripheral blood T lymphocytes by negative selection using immunoabsorption with goat anti-mouse lg-coated magnetic particles as previously described in June, C. H. et al., *Mol. Cell. Biol.*, 7:4472 (1987). This resulted in a population of resting T cells that was >99% $CD3^+$ and that did not contain $CD2^+/CD3^-$ cells such as NK cells. The Jurkat T leukemia cell line E6-1 was a gift from Dr. A. Weiss and maintained in complete media, i.e. RPMI 1640 containing 2 mM L-glutamine, 50 μg/ml gentamycin, and 10% FCS (HyClone Laboratories, Logan, Utah). In some instances, T cells or Jurkat cells were cultured in complete media, or in complete media with 5 ng/ml PMA (Sigma Chemical Co., St. Louis, Mo.) or OKT3 beads (±5 beads/cell) before experiments. The Jurkat J32 cell line ($CD2^+$, $CD3^-$, $CD28^+$) has been described in Makni, H. et al., *J. Immunol.*, 146:2522 (1991). J32 variants ($CD2^+$, $CD3^-$, $CD28^+$) were derived by γ irradiation-induced mutagenesis and immunoselection (see Makni, supra (1991)); one such cloned mutant, J32-72.4 is stable in culture. The surface receptor expression of these cells was quantitated by indirect immunofluorescence and analyzed by flow cytometry. The mean log fluorescence intensity for each sample was determined and was converted into linear relative fluorescence units ($_A$FL) by the formula $_AFL=10^{[(E-C)/D]}$; where E is the mean log fluorescence intensity of the experimental antibody sample, C is the mean log fluorescence intensity of the control antibody sample, D is 50 channels/decade. For the TCR/CD3 and CD28 receptors, $_A$FL of the J32 cells was 27.0 and 57.0, and for the J32-74.2 cells 1.1 and 40.7. Northern blot analysis of J32-72.4 revealed no detectable TCR-β mRNA, while the expression of the TCR-α, CD3-γ, δ, and ε and TCR ζ mRNA was similar to that of the parental J32 cells (unpublished data).

B7 transfection of CHO cells. CHO cells were transfected with B7 cDNA as previously described in Gimmi, C. D. et al., *PNAS* (*USA*), 88:6575 (1991). These cells have previously been shown to stimulate lymphocyte proliferation and lymphokine secretion in a manner that mimics CD28 mAb-induced T cell activation. See Linsley, P. S. et al., *J. Exp. Med.*, 173:721 (1991) and Gimmi, supra (1991). Transfected CHO cells showing no B7 expression were recloned and are referred to as CHO-B7$^-$. CHO cells were detached from tissue culture plates by incubation in PBS with 0.5 mM EDTA for 30 m and fixed in 0.4% paraformaldehyde as described in Gimmi, supra (1991). Fixed CHO-B7$^-$ cells were used as control cells.

Immunoblot analysis of protein tyrosine phosphorylation. Details of the immunoblot assay with anti-phosphotyrosine antibodies has been described in Hsi, E. D. et al., *J. Biol. Chem.*, 264:10836 (1989) and June, C. H. et al., *J. Immunol.*, 144:1591 (1990). Cells were suspended at $5-10 \times 10^7$ cells/ml in reaction media, i.e., HBSS containing 0.8% FCS and 20 Mm Hepes at 37° C. at time—3 m and stimulated at time 0 m. mAbs were used at 10 μg/ml final concentration. For crosslinking, biotinylated mAbs were incubated with cells for 5–8 m at room temperature, the cells prewarmed at time 3 min and stimulated with avidin (Sigma Chemical Co.) at a final concentration of 40 μg/ml at time 0. Stimulation was terminated by the addition of ice-cold 10× lysis buffer, yielding a final concentration of 0.5% Triton X-100. See June, *J. Immunol.*, supra (1990). After lysis at 4° C., nuclei were pelleted and postnuclear supernatants were subject to SDS-PAGE on a 7.5% gel, transferred to polyvinylidene difluoride microporous membrane (Millipore, Bedford, Mass.) and the membranes probed with affinity-purified anti-phosphotyrosine antibodies, labeled with $^{125}$I staphylococcal protein A (ICN, Irvine, Calif.) and exposed to x-ray film.

Results

Figure 15:
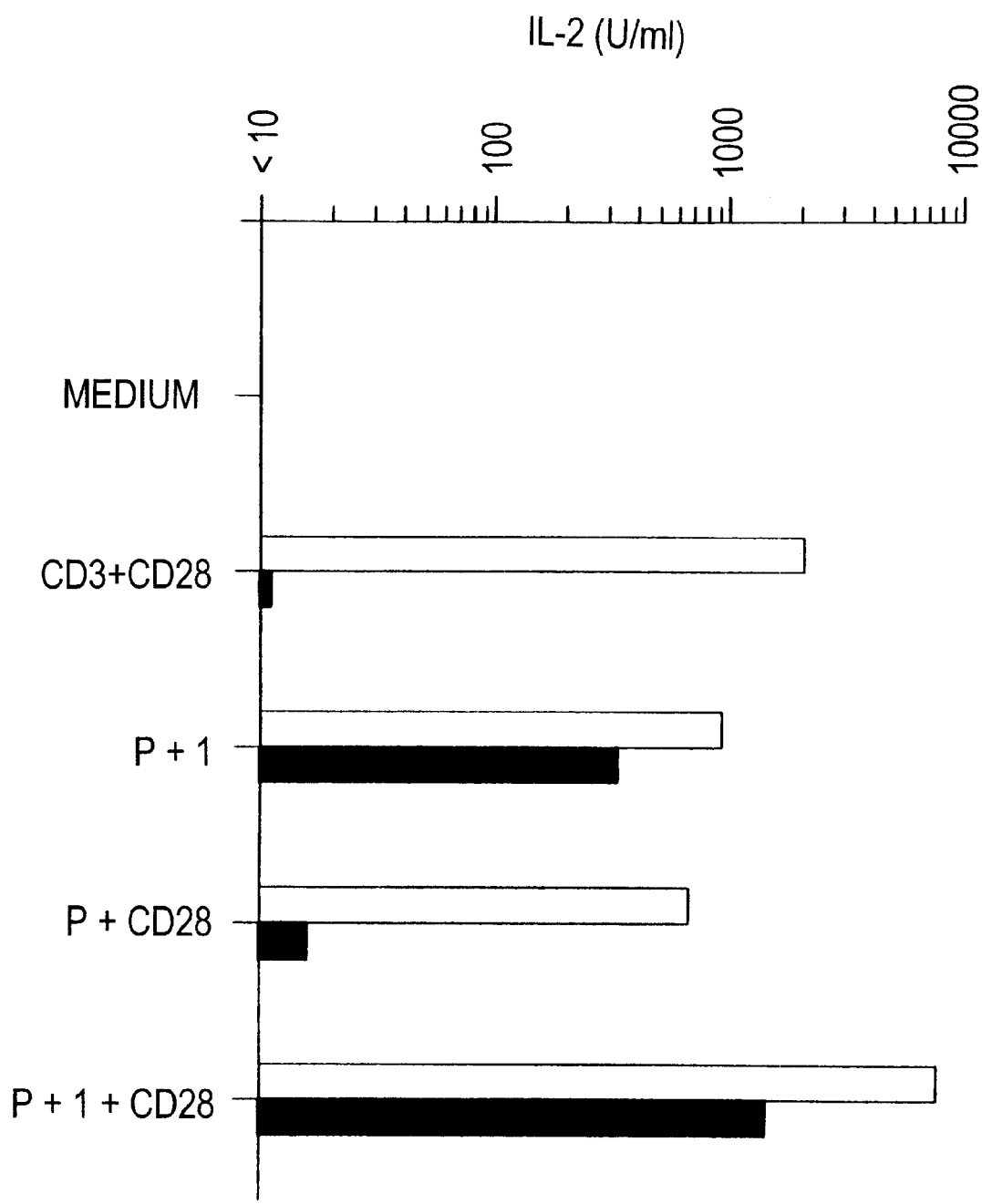
FIG. 15 is a bar graph illustrating the effect of herbimycin A on CD28-stimulated IL-2 production.

Herbimycin A prevents CD28-stimulated IL2 production. Previous studies have shown that three distinct biochemical signals, provided by phorbol esters, calcium ionophore, and ligation of the CD28 receptor with mAb, are required to cause optimal IL-2 secretion (see June, C. H. et al., *J. Immunol.*, 143:153 (1989)). Cells cultured in the presence of PMA, ionomycin, or CD28 mAb alone produced no detectable IL-2 and, as previously reported in June, *J. Immunol.*, (1989) supra, and Fraser, J. D. et al., *Science* (Wash., D.C.) 251:313 (1991), stimulation of the CD28 receptor strongly up-regulated IL-2 production of T cells stimulated with immobilized anti-CD2 mAb, PMA, or PMA plus ionomycin. To address the potential role of tyrosine kinases in CD28-triggered signaling, the effect of herbimycin $A_1$ an inhibitor of the src family protein tyrosine kinases (see Uehara, Y. et al., *Biochem. Biophys. Res. Commun.*, 163:803 (1989)), on the CD28-triggered enhancement of IL-2 production was investigated. T cells were cultured overnight in the absence (depicted as open bars in FIG. 15) or presence (depicted as filled bars in FIG. 15) of herbimycin A (1 μM). The cells were then cultured for a further 24 h period in the presence of medium-immobilized anti-CD3 mAb (G19-4), PMA (3 ng/ml) (P), or PMA plus ionomycin (150 ng/ml) (P+I) in the presence or absence of soluble anti-CD28 mAb 9.3 (1 μg/ml). Cell-free supernatant was collected, dialized to remove herbimycin A and serial dilutions were analyzed for IL-2 content by bioassay as described in June, *J. Immunol.*, supra (1989). FIG. 15 shows the effect of herbimycin A on CD28-stimulated IL-2 production. The CD28 mAb mediated enhancement of IL-2 production in response to stimulation with immobilized anti-CD3, or PMA was nearly completely inhibited in the presence of herbimycin A. In contrast, cells cultured in PMA, ionomycin or 9.3 mAb only produced <10 U/ml of IL-2.

Disruption of the proximal signaling pathway triggered through CD3 could potentially explain the effect of herbimycin on cells stimulated with anti-CD3 and anti-CD28. Consistent with this, CD3-triggered IL-2 production was previously shown to be exquisitely sensitive to herbimycin A. See June, C. H. et al., *PNAS* (*USA*), 87:7722 (1990). However, IL-2 production induced with the combination of PMA plus ionomycin or PMA plus CD28 stimulation permits, in principle, the ability to isolate the CD28 signal for testing the effect of herbimycin A. PMA plus anti-CD28-stimulated IL-2 production was sensitive to the effects of herbimycin A while, as previously noted, PMA plus ionomycin-stimulated IL-2 secretion was resistant to the effects of herbimycin A. The combination of PMA plus ionomycin plus anti-CD28-stimulation resulted in more IL-2 secretion than optimal amounts of PMA plus ionomycin, consistent with the previous reports of June, J. Immunol., supra (1989); and Fraser, J. D. et al., *Science* (Wash. D.C.) 251:313 (1991). However, in the presence of herbimycin $A_1$ PMA plus ionomycin plus CD28-stimulated cells produced approximately equivalent amounts of IL-2 as cells stimulated in the absence of herbimycin with PMA plus ionomycin. Together, the above results suggest that the function of both the TCR and CD28 receptors are sensitive to herbimycin, and further suggest the independent effects of these three reagents on IL-2 gene expression. See June, *J. Immunol.*, supra (1989); and Fraser, supra (1991).

CD28 receptor crosslinking with mAb induces protein tyrosine phosphorylation in PMA-treated Jurkat cells. Given the above functional results, the potential involvement of protein tyrosine phosphorylation in CD28-mediated signal transduction was investigated by immunoblot analysis of postnuclear supernatants of whole cell lysates of the T cell leukemia line Jurkat E6-1. Jurkat E-6 cells were cultured for 2 days in the presence or absence of PMA (5 ng/ml). After washing, $10^7$ cells in 120 μl were stimulated with reaction media (control), anti-CD3 Mab (G19-4), anti-CD28 mAb (9.3), or crosslinked anti-CD28 mAb (9.3) (final concentration, 10 μg/ml). For crosslinking, biotinylated mAb was added at time 10 m, followed by avidin (40 μg/ml) at time zero. After 2 m, the reaction was terminated with ice-cold lysis buffer and postnuclear supernatants were resolved by SDS-PAGE electrophoresis, transferred to immobilon, and immunoblotted with antiphosphotyrosine, followed by $^{125}$I-protein A and autoradiography.

In a previous report by Ledbetter, J. A. et al., *Blood*, 75:1531 (1990), increased tyrosine phosphorylation could not be detected in resting T cells after crosslinking the CD28 receptor. Consistent with that report, no changes in tyrosine phosphorylation were detected in unstimulated Jurkat cells after the binding of bivalent or crosslinked CD28 mAb. Previous studies have shown that CD28 stimulation alone does not result in lymphokine production in Jurkat cells or induce proliferation of primary T cells. See Weiss, A. et al., *J. Immunol.*, 137:819 (1986); Martin, P. J. et al., *J. Immunol.*, 136:3282 (1986); and Hara, T. et al., *J. Exp. Med.*, 161:1513 (1985). Engagement of CD28 by CD28 mAbs or by B7, the natural CD28 ligand, delivers a costimulatory signal provided T cells are stimulated with PMA or with TCR/CD3 mAbs. See June, C. H. et al., *Immunol. Today*, 11:211 (1990); Koulova, L. et al., *J. Exp. Med.*, 173:759 (1991); Linsley, P. S. et al., *J. Exp. Med.*, 173:721 (1991); and Gimmi, C. D. et al., *PNAS (USA)* 88:6575 (1991). It thus appeared that CD28-induced protein tyrosine phosphorylation might only occur in the context of a costimulatory signal.

To test this hypothesis, Jurkat cells were cultured in PMA and then stimulated with anti-CD28 mAb as previously described. In the PMA-stimulated cells, crosslinking of CD28 for 2 m induced phosphotyrosine on substrates migrating with approximate molecular masses of 47, 62, 75, 82, 100, 110, and 1.45 kD. Bivalent CD28 mAb induced tyrosine phosphorylation, but to a lesser magnitude. In agreement with June, C. H. et al., *J. Immunol.*, 144:1591 (1990), CD3 triggering of Jurkat cells induced tyrosine phosphorylation of phosphoprotein (pp) 56, pp65, pp75, pp100, pp110, and pp145 in resting Jurkat cells and in PMA-treated Jurkat cells. Of particular interest were pp75 and pp100, which were consistently phosphorylated by CD28 stimulation under all conditions tested.

CD28 receptor crosslinking with Mab induces protein tyrosine phosphorylation in normal T cells. Similar experiments with highly purified peripheral blood T cells from normal human donors were performed in order to determine if CD28 could increase tyrosine phosphorylation in non-transformed cells. Peripheral blood CD28$^+$T cells were cultured in PMA (5 ng/mi) for 6 h. After washing, $10^7$ cells were stimulated for 2 m with media (control), anti-CD3 mAb (G19.4), anti-CD28 mAb (9.3), crosslinked anti-CD28 mAb (9.3), or crosslinked anti-CD5 mAb (10.2). Cells were lysed and protein tyrosine phosphorylation was determined as previously described. Crosslinking of CD28 on PMA-treated cells induced the appearance of tyrosine phosphorylated substrates that migrated at 45, 75, and 100 kD. Again, pp75 and pp100 were most prominent and consistently reproduced.

The effects of CD28 stimulation observed after 24–48 h of PMA stimulation were more pronounced than those seen after 6 h. Ligation of CD28 by mAb on resting T cells caused the appearance of weakly detected tyrosine phosphorylation. The induction of increased responsiveness to anti-CD28 mAb stimulation by PMA is slow in that 4–6 h of PMA treatment are required to consistently observe CD28-induced tyrosine phosphorylation. Experiments with cycloheximide indicate that new protein synthesis is required for cells to become responsive to CD28. The specificity of the CD28-induced tyrosine phosphorylation was investigated by crosslinking CD5 with an isotype-matched mAb. Increased tyrosine phosphorylation on the 75 kD substrate was occasionally induced by CD5 crosslinking. In contrast, CD5 never induced tyrosine phosphorylation on pp100. Similarly, crosslinking of the MHC class I receptor also did not induce tyrosine phosphorylation of this substrate.

CD28 receptor crosslinking induces protein tyrosine phosphorylation in CD3-treated normal T cells. The above experiments suggested that the CD28 receptor is relatively inactive in quiescent cells, and becomes responsive consequent to protein kinase C activation. To determine whether TCR stimulation could also prime cells for the CD28 signal, T cells were cultured overnight in medium or in the presence of anti-CD3-coated beads. The cells were recovered, and $8\times10^6$ cells were stimulated with crosslinked anti-CD28 mAb for 0–5 m, the cells lysed, and protein tyrosine phosphorylation determined as previously described. Crosslinked CD28 mAb induced low level tyrosine phosphorylation on multiple substrates in resting T cells that peaked 2–5 m after CD28 stimulation. In contrast, CD28 mAb induced marked tyrosine phosphorylation in CD3-primed cells that was maximal within 1 m. Thus, costimulation of T cells with anti-CD3 augmented CD28-induced tyrosine phosphorylation as manifested by an increased magnitude of response and an accelerated kinetics of response. This induction of responsiveness to CD28 did not require DNA synthesis, as separate studies have shown that the T cell blasts used for these studies were in the late $G_1$ phase of the cell cycle.

CD28 receptor-B7/BB1 receptor interaction induces specific tyrosine phosphorylation in T cells. The above results indicate that CD28 mAb can increase tyrosine phosphorylation in a variety of substrates on preactivated T cells. Previous studies have indicated that CD28 appears to deliver two biochemically distinct signals, depending on the degree of crosslinking. See Ledbetter, J. A. et al., *Blood*, 75:1531 (1990). The unique functional properties of CD28 mAb observed after stimulation of T cells do not require highly crosslinked CD28 mAb and are obtained using intact or F(ab')$_2$ CD28 mAb. As discussed in Hara, T. et al., *J. Exp. Med.*, 161:1513 (1985), studies have shown that CHO cells expressing the CD28 ligand mimic the functional effects of CD28 mAb. See Linsley, supra (1991), and Gimmi, supra (1991). These cells presumably represent a more physiologic means to study CD28 receptor-mediated signal transduction. CHO-B7$^+$ cells were incubated with PMA-treated T cells at a CHO/T cell ratio of 1:10 for 5–30 m. B7-transfected CHO cells not expressing B7 on the cell surface (CHO-B7$^-$ cells) were used as controls. Before the stimulation, CHO cells were fixed with paraformaldehyde to decrease phosphotyrosine background. Previous studies have indicated that this treatment leaves intact B7-CD28 interaction and the ensuing functional effects. See Gimmi, supra (1991). For the time zero point, lysis buffer was added to the T cells first, immediately followed by addition of CHO cells to the mixture. CHO-B7$^+$ cells induced specific tyrosine phosphorylation that was detected primarily on a substrate that migrated at 100 kD. The CHO-B7-induced tyrosine phosphorylation was detectable within 5 m of stimulation and remained elevated at plateau levels for at least 30 m. CHO-B7-induced tyrosine phosphorylation was evident at a variety of CHO-T cell ratios, and has been consistently observed for only the 100 kD substrate. CHO-B7⁻ cells did not induce tyrosine phosphorylation of pp100. The B7-induced tyrosine phosphorylation was dependent upon CD28-B7 interaction as preincubation of CHO cells with anti-B7 mAb prevented CHO-B7 induced pp100 tyrosine phosphorylation. B7-CHO cells induced a slight increase in pp100 tyrosine phosphorylation in some experiments; however, this was not consistently observed.

In other experiments, alloantigen-induced T cell blasts were tested for CD28-induced tyrosine phosphorylation. T cells were culture for 8 days with allogeneic irradiated cells and then stimulated with CD28 mAb. Tyrosine phosphorylation that was most pronounced on the 74 and 100 kD substrates was observed. Thus, CD28 stimulation of T cells preactivated with alloantigen, CD3 mAb, or PMA can induce tyrosine phosphorylation on a limited number of substrates that is early in onset and brief in duration.

CD28-induced tyrosine phosphorylation prevented by CD45 and by herbimycin. Given that protein tyrosine kinase inhibitor herbimycin A could efficiently inhibit CD28-induced IL-2 secretion, this inhibitor was tested for effects on CD28-induced tyrosine phosphorylation. T cells were treated overnight with PMA (5 ng/ml) in the presence of the indicated concentration of herbimycin A or in control medium. The cells were collected, washed, and 8×10⁶ cells were stimulated with media or with crosslinked anti-CD28 mAb for 2 m. Detergent-soluble proteins were processed as previously described. Tyrosine phosphorylation induced by anti-CD28 mAb was nearly completely prevented in herbimycin-treated cells under conditions that specifically inhibit CD28-induced IL-2 production.

The brief temporal course of CD28 mAb-induced tyrosine phosphorylation suggested regulation by a phosphatase. To address the effects of phosphatases on CD28-mediated signal transduction, T cells were cultured overnight with PMA (5 ng/ml). 10⁷ cells were incubated for 10 m with media (control), biotinylated anti-CD45 mAb (9.4), anti-CD28 mAb (9.3), or both. Monoclonal antibodies were crosslinked with avidin at time 0. The reaction was terminated after 2 m. Immunoblot analysis with antiphosphotyrosine antibodies of detergent-soluble proteins was performed as previously described. CD28 crosslinking induced tyrosine phosphorylation on pp75 and pp100 that was completely prevented by CD45. Consistent with previous results described in Samelson, L. E. et al., *J. Immunol.*, 145:2448 (1990), crosslinking of CD45 alone caused increased tyrosine phosphorylation of a 120–135 kD substrate; this effect is also seen in CD28 plus CD45-treated cells. Thus, the above studies indicate that CD28-induced tyrosine phosphorylation is sensitive to an inhibitor of src family protein tyrosine kinases, and furthermore, that the CD45 protein tyrosine phosphatase can prevent CD28-induced protein tyrosine phosphorylation.

CTLA-4 expression predicts expression of IL-2 following CD28 pathway activation. Purified resting T cells were stimulated with immobilized anti-CD2 Ab, anti-CD3+mAb 9.3, PMA+ionomycin, PMA+mAb 9.3 and PMA+ionomycin+mAb 9.3 in the presence or absence of the protein-tyrosine kinase inhibitor herbimycin for 8 h. Duplicate Northern blots were hybridized to CTLA-4, CD28, IL-2 or HLA specific probes. Expression of CD28, CTLA-4 and IL-2 was then analyzed by Northern blot. IL-2 expression correlated well with CTLA-4 expression following CD28 pathway activation. CTLA-4 and IL-2 expression were also suppressed to a similar degree with herbimycin while CD28 expression remained unchanged. This suggests that the suppressive effects of protein-tyrosine kinase inhibitors on CD28 pathway activation may be mediated through suppression of CTLA-4 expression.

SPECIFIC EXAMPLE XII

Induction of MHC Independent T Cell Proliferation by CD28 and Staphylococcus Enterotoxins Protocol Isolation of T cells. Peripheral blood was drawn from normal human volunteers. The mononuclear cell fraction was obtained by density gradient centrifugation through a Ficoll-Hypaque (Pharmacia) cushion. This fraction was used in experiments utilizing peripheral blood mononuclear cells (PBMCs). Purified resting T cells were obtained by incubating the mononuclear cells with an antibody cocktail directed against B cells, monocytes and activated T cells. The antibody coated cells were then removed by incubation with goat anti-mouse immunoglobulin-coated magnetic beads (Advanced Magnetics Inc.) as previously described in June, supra (1987). This method has routinely yielded a population >99% $CD2^+$ by flow cytometry.

Proliferation assays. Proliferation was measured by culturing 5×10⁵ purified T cells or PBMC's in each well of a 96 well microtiter plate. The final culture volume was 200 μl of RPMI 1640 (Gibco) supplemented with 10% FCS, penicillin (100 U/ml), streptomycin (100 μg/ml) and 2 Mm L-glutamine. Staphylococcal Enterotoxin A (SEA), Staphylococcal Enterotoxin B (SEB) (Toxin Technologies) and cyclosporine A (Sandoz) were added in the indicated doses at the initiation of the culture. Anti-CD28 monoclonal antibody (mAb 9.3, gift from J. Ledbetter) and anti-HLA-DR monoclonal antibody (mAb L243, gift from J. Ledbetter) were added at the start of the culture period. Tritiated thymidine (³H-TdR, ICN) was included at a concentration of 1 μCi per well for the final 8 h of the culture. The cells were harvested onto glass microfiber filter strips (Whatman) after 72 h using a PHD cell harvester (Cambridge Technologies) and counted on a liquid scintillation counter (LKB). All values are expressed as the mean cpm±standard deviation of triplicate or quadruplicate cultures.

Flow Cytometry. One ml cultures of T cells were incubated with media alone, SEA (100 ng/ml) or SEB (1 μg/ml), SEA or SEB plus anti-CD28 antibody (1 μg/ml) or PMA (3 ng/ml) plus anti-CD28 antibody (1 μg/ml) at 37° C. for 72 h. Aliquots of each sample were stained with acridine orange (Polysciences) for cell cycle analysis as described in Darzynkiewicz, Z., *Meth. Cell. Biol.*, 33:285 (1990), FITC conjugated anti-IL2 receptor antibody (Coulter), FITC conjugated anti-HLA-DR antibody (Becton-Dickinson) or an isotype-matched irrelevant antibody (Becton-Dickinson). Each sample was analyzed on a FACScan flow cytometer (Becton-Dickinson).

Results

CD28 provides costimulatory activity for superantigen-activated purified T cells. Highly purified T cells were cultured with graded concentrations of either SEA (0.1 ng/ml to 1.0 μg/ml) or SEB (0.01 μg/ml to 100 μg/ml). Replicate cultures were prepared in which a stimulatory antibody to CD28 was added. The cultures were pulsed with ³H-TdR for the final 8 h of a 72 h culture and incorporated thymidine determined by liquid scintillation counting as described above. Each condition was performed in quadruplicate. Treatment with SEB alone failed to induce thymidine incorporation above control cultures. However, the addition of anti-CD28 antibody resulted in significant proliferation to graded doses of SEB. Treatment with anti-CD28 antibody alone had no effect. The lack of accessory cells was verified by an absence of proliferation to PHA. Identical results were obtained using SEA.

Stimulation with SEA or SEB leads to cell cycle entry. Since CD28 stimulation alone does not induce T cell cycle entry, the observation that CD28 provided costimulatory activity for T cells treated with either SEA or SEB suggested that these enterotoxins could induce cell cycle entry in purified T cells. In order to examine this, purified T cell cultures were stimulated with SEB (1 μg/ml) alone or with SEB (1 μg/ml) plus anti-CD28 monoclonal antibody (1 μg/ml) for 48 h and stained with acridine orange for cell cycle analysis. Unstimulated cells were run simultaneously in order to determine the $G_0/G_1$ interface. Those with an increased RNA content but unchanged DNA content were considered $G_1$ phase cells. Cells with increases in both RNA and DNA content were considered in S, $G_2$ or M phases. Concomitantly, aliquots were stained with FITC-conjugated anti-IL-2 receptor antibody. Treatment with enterotoxin alone for 48 h resulted in progression of greater than 10% of the T cells from $G_0$ to $G_1$ as determined by an increase in RNA staining with no increase in DNA content. Similarly, enterotoxin alone induced IL-2 receptor expression in 15% of the cells at 72 h. In contrast, when the anti-CD28 monoclonal antibody was present, a significant proportion of the cells that had left the $G_0$ stage of the cell cycle were found to have increased their DNA content and thus are in either the S, $G_2$ or M phases of the cell cycle. These data indicate that stimulation with SEB alone is sufficient to activate the T cell but delivers an inadequate signal for complete progression through the cell cycle. Provision of a second signal by simultaneous stimulation of the CD28 pathway allowed the cell to progress to S-phase and proliferate.

Proliferation of T cells stimulated by SEA and anti-CD28 is resistant to cyclosporine A. CD28 has been shown to utilize a signal transduction pathway that is resistant to the effects of cyclosporine A (CsA) when the initial signal is provided by PMA, and partially resistant to CsA when cells are initially activated through the T cell receptor. See June, supra (1987). In order to further examine the pathways involved in T cell activation by enterotoxin, cyclosporine A (1 μg/ml) was included in cultures activated by SEA and SEA plus anti-CD28 antibody ($^3$H-TdR incorporation determined as described above). As for SEB, SEA alone did not induce thymidine incorporation whereas addition of antibody against CD28 resulted in significant proliferation. Even in the presence of cyclosporine A (1 μg/ml), there was a dose dependent increase in proliferation when cultures were activated by a combination of SEA and anti-CD28 antibody. Control cultures activated with PMA plus anti-CD28 antibody were resistant to cyclosporine A and activation by PMA plus ionomycin was sensitive to cyclosporine A.

Activation by SEB and anti-CD28 is independent of class II MHC. Previous work has demonstrated that the staphylococcal enterotoxins are capable of simultaneously binding the TCR and class II MHC molecules on the surface of antigen presenting cells (APCs). See Herrmann, T. et al., *Eur. J. Immunol.*, 19:2171 (1989); and Chintagumpala, M. M. et al., *J. Immunol.*, 147:3876 (1991). The observation that proliferation was not observed unless APCs were present in the culture was interpreted to mean that T cell activation by superantigen is dependent upon class II MHC expression as discussed in Fleischer, B. et al., *J. Exp. Med.*, 167:1697 (1988); Carlsson, R. et al., *J. Immunol.*, 140:2484 (1988); and Herman, A. et al., *J. Exp. Med.*, 172:709 (1990). Our observation that highly purified T cells could be induced to proliferate by simultaneous stimulation with enterotoxin and anti-CD28 antibody suggested that class II MHC may not be absolutely required for superantigen activation of T cells. Alternatively, activated T cells can express class II MHC and thus might provide class II-dependent superantigen presentation to other T cells in trans.

Figure 16:
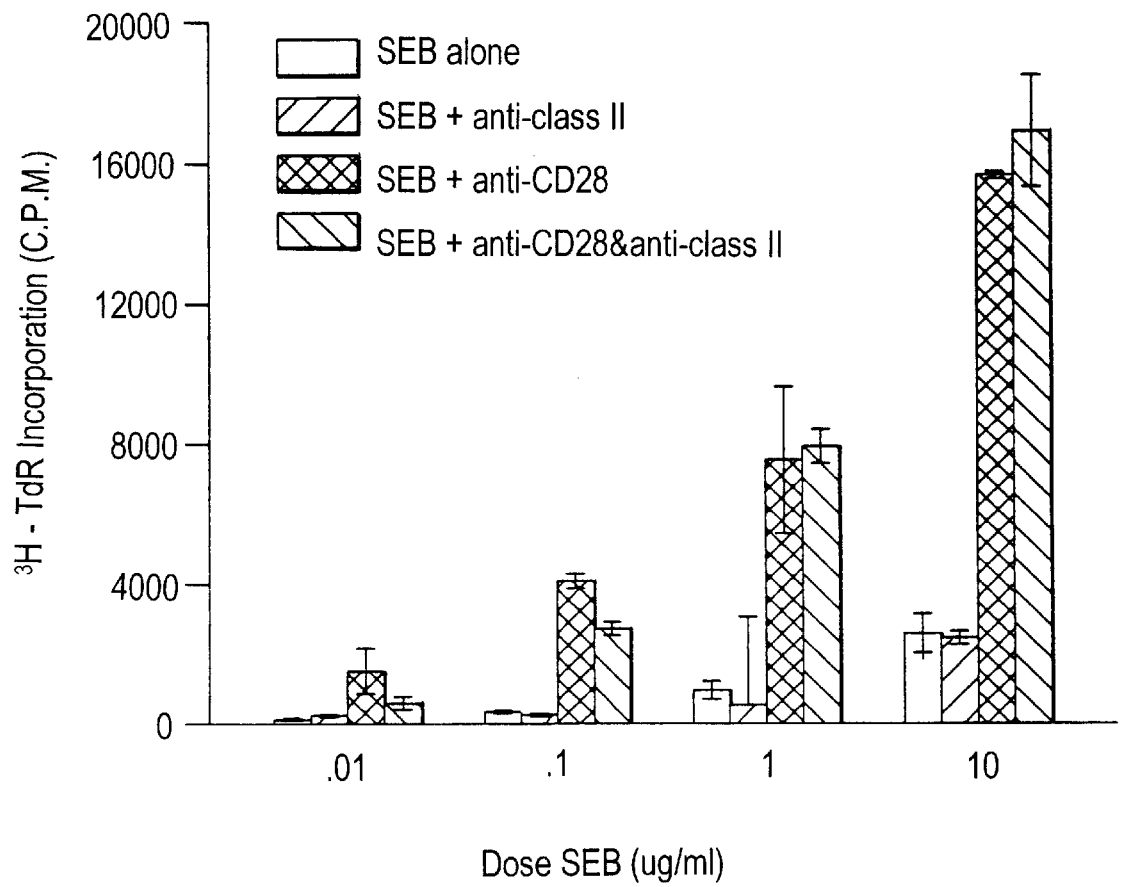
FIG. 16 is a bar graph illustrating activation by SEB and anti-CD28 on purified resting T cells in the presence and absence of a blocking Mab to HLA-DR.
Figure 17:
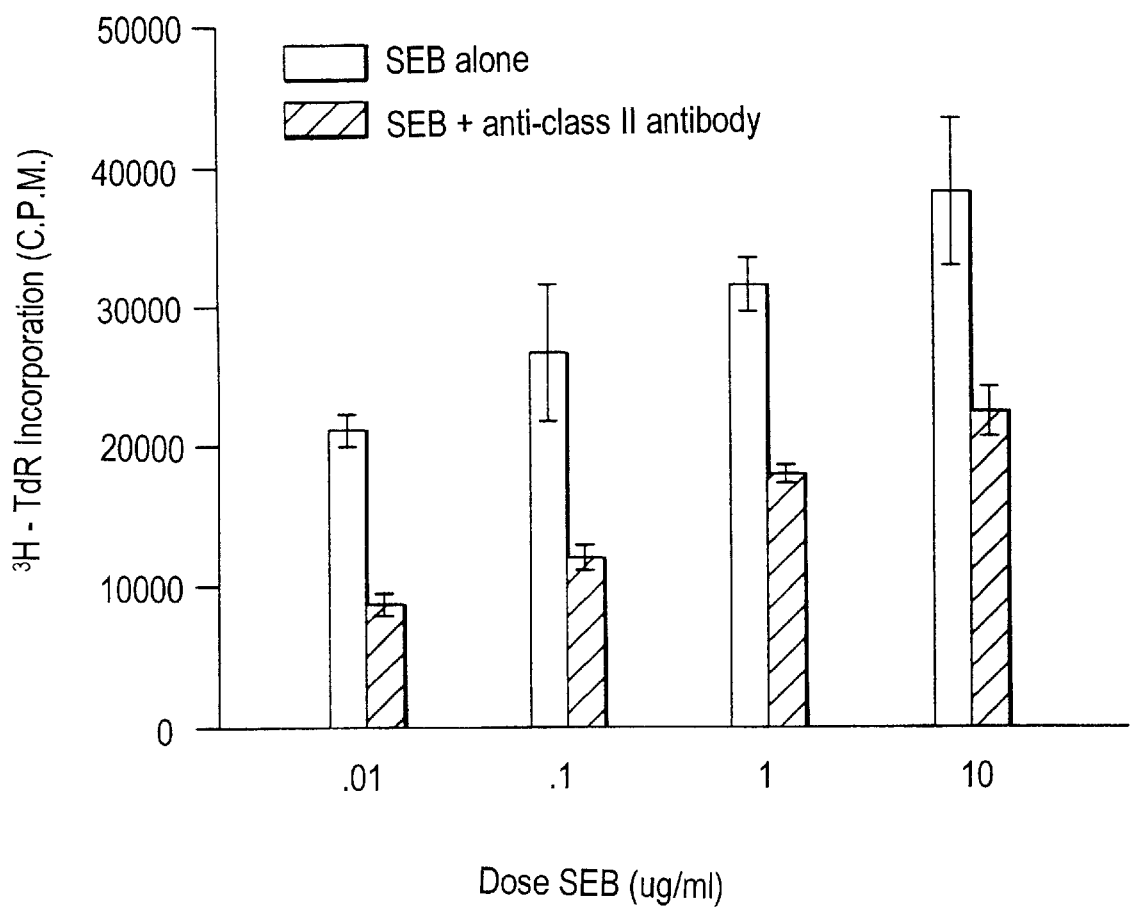
FIG. 17 is a bar graph illustrating activation by SEB alone or SEB and blocking Mab to HLA-DR in peripheral blood mononuclear cells.

To examine this possibility, a blocking antibody against HLA-DR, monoclonal antibody L243, was included in cultures of T cells and PBMCs activated by enterotoxin or enterotoxin plus anti-CD28 antibody as shown in FIG. 16. Each point is expressed as the mean±the standard deviation of triplicate or quadruplicate cultures. No significant proliferation was observed with SEB alone. As shown previously, inclusion of anti-CD28 antibody allows SEB to induce T cell proliferation in a dose-dependent manner. There was no decrease in proliferation when anti-class II antibody was included in the cultures at doses of 1.0 or 10 μg/ml (data for 10 μg/ml not shown). In contrast, as shown in FIG. 17, the proliferation of PBMCs isolated from the same donor and stimulated with enterotoxin was significantly inhibited by anti-class II antibody. In addition, HLA-DR expression at 24 and 72 h was examined by purified T cells activated with SEA (0.1 or 1.0 ng/ml) with and without CD28 costimulation. There was no expression of HLA-DR in either condition as determined by flow cytometry. This indicated that the T cell proliferation induced by enterotoxin+anti-CD28 is not dependent on presentation by an MHC class II molecule.

SPECIFIC EXAMPLE XIII

Prevention of Programmed Cell Death

A series of experiments were done to test whether anti-CD28 mAb might prevent cell death in mature T cells. Jurkat leukemia cells are commonly used as an example of mature T cells that mimic physiologic effects found in peripheral blood T cells. For example, Jurkat cells can be induced to secrete IL-2 with anti-CD3 mAb and anti-CD28 mAb, and Jurkat cells can be infected and killed by HIV-1. The Jurkat line JHMI-2.2 was obtained from A. Weiss (UCSF); the muscarinic $M_1$ receptor subtype has been transfected and is stably expressed in these cells. JHMI-2.2 cells, $0.3 \times 10^6$/well, were added to culture wells in complete medium, or to wells that contained plastic-adsorbed anti-CD3 mAb G19-4, in the presence or absence of 9.3 mAb 10 μg/ml, or 9.3 mAb alone. Cell death was scored after 1 to 3 days of culture and graded as 0 (none), 1+(20 to 70% of cells dead), and 2+(70 to 100% of cells dead), and was determined by visual inspection of the wells, and confirmed by trypan blue permeability. As shown in Table 10, cells in medium continued to grow and remain viable while cells in anti-CD3-treated wells died. In contrast, the cells in wells containing anti-CD3 plus anti-CD28 continued to proliferate. The ability of anti-CD28 to rescue cells from anti-CD3-induced cell death was specific, because carbacol (30 μM) (a specific agonist of $M_1$ receptors that is believed to activate signal transduction in cells via a mechanism distinct from the T cell receptor/CD3 complex), also induced cell death in Jurkat cells. Anti-CD28 did not prevent carbacol-induced cell death.

TABLE 10

| CONDITION | CELL DEATH (GRADE 0–2) |
|---|---|
| EXPERIMENT #1 | |
| Medium | 0 |
| anti-CD3 | 2+ |
| anti-CD3 + anti-CD28 | 0 |
| EXPERIMENT #2 | |
| Medium | 0 |
| Carbacol | 1+ |
| Carbacol + anti-CD28 | 2+ |

SPECIFIC EXAMPLE XIV

Bone Marrow Studies

Proliferation of T cells after activation of T cells with soluble or immobilized anti-CD3 (OKT3). A series of titration studies were performed using soluble or immobilized OKT3 to activate and induce T cell proliferation. Immobilized OKT3 (2 $\mu$/ml precoated plates for 1 h at 37° C.) and soluble OKT3 (10 ng/ml) consistently induced T cell proliferative responses from E-rosette ($E^+$) purified T cells or PBL. PBL or purified T cells were activated by incubation for 1 h to 7 days on immobilized OKT3 or by adding 10 ng/ml of soluble OKT3 at the beginning of culture. In a series of experiments, proliferation after activation of T cells with immobilized OKT3 was comparable to proliferative responses by PBL after activation with soluble OKT3.

Cytotoxicity mediated by anti-CD3 and anti-CD28 triggered PBL. The cytotoxicity of anti-CD3 activated PBL after 7 days of culture in the presence of low doses of IL-2 or anti-CD28 was tested. In this set of experiments, the ability of CD28 to induce increases in lymphokine production to substitute for previously reported immune augmented effects of in vitro T cell treatment with IL-2 has been examined. One lytic unit is equivalent to 20% lysis of $5\times10^3$ target cells per $1\times10^6$ effector cells as discussed in Press, H. F. et al., *J. Clin. Immunol.* 1:51–83 (1981). Various targets, including Daudi and K562, were tested. Cytotoxicity results of a representative experiment are shown in Table 11.

TABLE 11

| CELL GROWTH STIMULUS | Target - Daudi (LU) | Target - K562 (LU) |
|---|---|---|
| anti-CD3 plus IL-2 | 14.9 | 10.6 |
| anti-CD3 plus anti-CD28 | 12.1 | 6.1 |

OKT3-induced cytotoxicity in PBL comparable to T cells. In 5 different subjects, PBL were compared with T cells ($E^+$) in their ability to kill Daudi, K562, and BSB cells 8 days after being activated with OKT3. These experiments were performed in X-Vivo 10 supplemented with 5% human serum (HS). The mean cytotoxicity in 5 normal subjects using PBL directed at Daudi, K562, and BSB were 15.0, 7.4, and 9.2 LU, respectively. In T cells from the same 5 subjects, the mean cytotoxicity directed at Daudi, K562, and BSB were 14.3, 7.7, and 9.3 LU, respectively.

Cytotoxicity as a function of in vitro time in cell culture. In order to test for optimal cytotoxicity, T cells were cultured with anti-CD3 and IL-2 for 31 days and tested at weekly intervals for cytotoxicity against Daudi and K562. Logarithmic cell growth was maintained during this time, with a 300-fold expansion in cell number. Cytotoxicity was a strong function of culture duration however, with <0.1, 24, 3.5, 0.5, 1.0 LU at 0, 8, 15, 22, and 29 days of culture. Similar results were found when Daudi was the target, with <0.01, 23, 5, 2, and 5 LU at 0, 8, 15, 22, and 29 days of culture.

Cytotoxicity induced by soluble or immobilized OKT3. In 7 experiments, cytotoxicity mediated by T cells after activation was compared with soluble or immobilized OKT3. Both methods induced cytotoxicity directed at Daudi and K562. Soluble OKT3 activated T cells mediated a mean cytotoxicity of 27 LU (SD-18) directed at Daudi and a mean cytotoxicity of 21 LU (SD-16) directed at K562. Immobilized OKT3 activated T cells mediated a mean cytotoxicity of 22 LU (SD-16) directed at Daudi and a mean cytotoxicity of 12 LU (SD-8) directed at K562. These experiments were performed with $E^+$ cells in RPMI 1640 supplemented with 10% fetal bovine serum (FBS). Cytotoxicity was assessed 7 to 8 days after triggering with soluble (10 ng/ml) or immobilized (2 $\mu$g/ml) OKT3.

Effects of IL-2 concentrations. The dose of IL-2 was titrated after establishing the optimal time of OKT3 activation. In several experiments, the doses of IL-2 were gradually reduced from 6000 IU/ml to 60 IU/ml. Proliferation, as measured by tritiated hymidine incorporation after 3 days of culture, remained constant as IL-2 was titrated in this range. In contrast, cytotoxicity varied with the dose of IL-2, and was maximal at lower doses of IL-2 (lytic units with Daudi targets were 28, 9, 8.5, 9 and 4.8 LU after culture in 30, 150, 300, 600 and 6000 IU/ml of rIL-2). The data show that both proliferative and cytotoxic responses of the anti-CD3 triggered T cells can be obtained and maintained in low doses of IL-2.

Effects of serum and medium on proliferation and cytotoxicity. The ability of HS, FBS, and serum free media were compared for their ability to support growth and maintain cytotoxicity. The data show that proliferation and cytotoxicity directed at Daudi, K562, and BSB rapidly decreased below a serum concentration of 2%. There were no significant differences between X-Vivo 10 and RPMI 1640.

Bone marrow mononuclear cells (BMMNC) as a source of CTC after anti-CD3 and anti-CD28 treatment. To test whether BMMNC might serve as a source of T cells for therapy in patients with malignancies, BMMNC were cultured in X-Vivo 10 medium after OKT3 and IL-2 or anti-CD28 stimulation. Although the BMMNC population initially contained only 25% $CD3^+$ cells, proliferative and cytotoxic responses were excellent after 2 weeks of culture. T cells expanded more than 40-fold after CD3 and IL-2 stimulation and cytotoxicity was between 5 and 12 LU at 8 to 15 days of culture when tested against Daudi and K562. These data show that BMMNC obtained from autologous bone marrow harvest from a patient before bone marrow transplantation provide a suitable source of cytotoxic T cells. Table 12 shows that both normal and patient bone marrows provide satisfactory sources of cytotoxicity after CD3 and IL-2 treatment. In 4 experiments using normal bone marrow or autologous bone marrow, there was a median of 89-fold expansion of cells (range 18- to 173-fold) after 9 to 19 days of culture. Mean cytotoxicity directed at Daudi and K562 mediated by BMMNC stimulated with OKT3 was 5.5 LU (range 2–11) and 4.3 LU (range 2–8), respectively. All cultures were tested 14 days after activation with OKT3 and expanded in the presence of 50 IU/ml of IL-2. Either soluble OKT3 10 ng/ml(s) or immobilized OKT3 (coated with 2 $\mu$g/ml)(I) were added as indicated.

TABLE 12

| Source | OKT3 (S or I) | Fold Increase | Daudi LU | K562 LU |
|---|---|---|---|---|
| PBL | | | | |
| 1 | I | 47 | 6 | 3 |
| 2 | I | 4 | 11 | 11 |
| 3 | S | 12 | 9 | 6 |
| 4 | S | 176 | 5 | 4 |
| BMMNC | | | | |
| 1 | I | 89 | 2 | 2 |
| 2 | I | 18 | 11 | 8 |
| 3 | S | 22 | 6 | 5 |
| 4 | S | 173 | 3 | 2 |

Anti-CD3 plus anti-CD28 treatment of BMMNC as a source of effector T cells. Proliferative and cytotoxic responses from 3 patients were tested. The patients had received extensive chemotherapy and yet their PBL or BMMNC maintained strong proliferative and cytotoxic responses after anti-CD3 plus anti-CD28 treatment. PBL or BMMNC ($1.5 \times 10^5$) were cultured in RPMI plus 5% human serum in the presence of immobilized OKT3 mAb or 50 IU/ml rIL-2 or 9.3 mAb 0.5 µg/ml. Proliferation was assessed on day 3 of culture and cytotoxicity on day 7. Table 13 summarizes the results for BMMNC.

TABLE 13

| SAMPLE | Proliferation $^3$H incorp. (cpm) | Cytotoxicity Daudi (LU) | Cytotoxicity K562 (LU) |
|---|---|---|---|
| Bone Marrow #171 AML, Relapsed | | | |
| OKT3 | 23,479 | — | — |
| OKT3 + anti-CD28 mAb | 58,563 | 18.0 | 4.8 |
| OKT3 + IL-2 | 48,745 | 15.1 | 4.6 |
| PBL P#632 non-Hodgkins lymphoma, pre-transplant | | | |
| OKT3 | 58,670 | — | — |
| OKT3 + anti-CD28 mAb | 77,046 | 14.8 | 12.7 |
| OKT3 + IL-2 | 63,603 | 18.8 | 18.1 |
| PBL P#635 Hodgkins lymphoma, pre-transplant | | | |
| OKT3 | 27,758 | — | — |
| OKT3 + anti-CD28 mAb | 46,133 | — | — |
| OKT3 + IL-2 | 43,918 | — | — |

OKT3-activated T cells (CTC) do not inhibit hematopoietic progenitor growth. In order to determine whether BMMNC mixed with OKT3-activated T cells (CTC) in hematopoietic progenitor assays would inhibit the development of CFU-GM, CTC obtained from PBL after a week of growth was mixed with fresh BMMNC and plated the mixtures into the CFU-GM assay. The autologous CTC were mixed with BMMNC in various ratios, incubated for 1 h at 37°, and then plated in a standard CFU-GM assay. The CTC had no deleterious effect on colony formation, as the number of CFU-GM colonies was within 75% of control over a wide variety CTC:BMMNC ratios (ratios of 1:25 to 5). The number of CFU-GM colonies was not inhibited greater than 90% (an accepted % inhibition of CFU-GM in purged autologous marrow grafts) even at a ratio of 1 CTC to 1 BMMNC. These data suggest that CTC will not inhibit or delay engraftment of autologous bone marrow transplants.

Expansion and cytotoxic functions of PBL or BMMNC from patients before BMT. In order to determine whether PBL or BMMNC from patients heavily pretreated for AML or lymphoma could be activated with anti-CD3 and grown in low dose IL-2, PBL or BMMNC obtained prior to BMT on several patients was tested. The PBL and BMMNC of the patients tested proliferated and exhibited cytotoxicity in a fashion comparable to that seen in normal PBL or BMMNC obtained from normal allogeneic marrow donors. It was anticipated that some patients that had been heavily treated with chemotherapy or radiation would have low counts or have poor responses to anti-CD3 activation. Thus, the number of starting cells was increased in the protocol to compensate for cell loss or inability to proliferate. The use of 9.3 as a costimulant to anti-CD3 activated T cells to enhance helper activity or enhance cytotoxicity could result in improved in vitro expansion of activated T cells. Data presented in this example (Specific Example XIV) show that mAb 9.3 can correct proliferative defects in post-transplant lymphocytes further supporting the rationale for using OKT3/9.3 costimulation approach to accelerate immune reconstitution and enhance cytotoxicity directed at malignant cells in ABMT recipients. A recent study by Katsanis, E. et al., *Blood* 78:1286–1291 (1991) shows that T cells from BMT recipients can be expanded by stimulation with OKT3 and IL-2.

Messenger RNA levels for IL-2 receptors (IL-2R), IL-2, and IL-3 in PBL from short and long-term BMT recipients. Earlier studies (see Lum, L. G. et al., *Blood Suppl.* (Abstract) (1991)) suggested that T cells from BMT recipients fail to secrete IL-2 or express IL-2R. Such defects may be due to failure of mRNA synthesis for lymphokines or lymphokine receptors. A determination was made whether T cells from BMT patients failed to express detectable levels of mRNA for IL-2, IL-2R and IL-3. PBL from 11 allogeneic (3 short-term, ST, and 8 long-term, LT) and 4 autologous recipients (2 ST and 2 LT) were tested for levels of IL-2R, IL-2, and IL-3 mRNAs without stimulation (−) or after phytohemagglutinin (PHA) and phorbol ester (TPA) stimulation (+). cDNA synthesized by reverse transcriptase (RTase) from total RNA was amplified by PCR using specific primers and the PCR products run on 1.5% agarose gels containing ethidium bromide. Table 14 shows the fraction and percent of recipients whose PBL had detectable levels of mRNA for IL-2R, IL-2, and IL-3.

TABLE 14

| STIMULATION | IL-2R (%) | IL-2 (%) | IL-3 (%) |
|---|---|---|---|
| Allogeneic Recipients | | | |
| − | 2/11 (18) | 1/9 (11) | 8/11 (73) |
| + | 9/11 (82) | 8/9 (89) | 7/10 (70) |
| Autologous Recipients | | | |
| − | 2/4 (50) | 3/4 (75) | 4/4 (100) |
| + | 4/4 (100) | 3/4 (75) | 3/4 (75) |

PBL from a high proportion of ST and LT autologous and allogeneic BMT recipients expressed levels of mRNAs for IL-2R, IL-2, and IL-3 after stimulation with PHA+TPA. In the ST recipients tested, 2 of 2 ABMT recipients and 3 of 3 allogeneic recipients tested had PBL that expressed mRNA levels of IL-2R and IL-3; 2 of 2 allogeneic recipients tested expressed mRNA for IL-2. In most cases, defective mRNA synthesis for IL-2R, IL-2, and IL-3 may not be responsible for defects in IL-2 secretion and IL-2R expression. Post-transcriptional events may play a more important role in defective lymphokine secretion by T cells from BMT recipients.

CTC help Ig synthesis and express mRNA for lymphokines and perforin.

As discussed in Ueda, M. et al., *J. Cell. Biochem.* (Abstract) (submitted 1992), helper activity was assessed by adding normal T cells or T cells activated with OKT3 to normal B cells after PW stimulation as measured by an ELISA-Plaque (PFC) assay. The number of PFC per million B cells cultured was 3200, 4100, 8800 when 25, 50 or 75×10$^3$ normal T cells were added. When the same numbers of CTC were added, the number of PFC were 220, 2100, and 2600. Thus, CTC exhibit substantial helper activity. Furthermore, CTC did not suppress normal autologous or allogeneic T and B cells in a suppressor assay for Ig synthesis. Helper activity was radioresistant. Messenger RNA for IL-2, IL-3, IL-6 and perforin was detected from 6 h to more than 3 days after OKT3 activation using a Rtase-PCR method. In summary, CTC help B cells produced Ig and did not suppress Ig synthesis by normal T and B cells. Thus, adoptive transfer of CTC after BMT may not only mediate a GVL effect but may accelerate immune reconstitution.

Defects in anti-CD3-induced proliferative responses in PBL from BMT patients repaired by adding anti-CD28. In vitro data on anti-CD3 and anti-CD3/anti-CD28 stimulated proliferative responses of T cells from BMT recipients support the premise that using Mab 9.3 in combination with OKT3 may have potent in vivo clinical effects as reported. See Joshi, I. et al., *Blood Suppl.* (Abstract) (1991). T cells from BMT recipients have defects in proliferation after mitogen or anti-CD3 stimulation. Previous studies show that costimulation of normal T cells with anti-CD3 (G19-4) and 9.3 enhance anti-CD3-induced proliferation by stabilizing lymphokine mRNAs. Experimentation to assess the ability of anti-CD3 (G19-4 or OKT3)+9.3 to correct defective anti-CD3-induced proliferative responses in PBL from autologous and allogeneic BMT recipients (53–605 days post BMT) was performed. PBL from recipients or controls were stimulated for 3 days with G19-4, G19-4+9.3, OKT3, or OKT3+9.3. 9.3 was added at a final concentration of 100 ng/ml. Fifteen tests were performed on ABMT recipients and sixteen tests were performed on allogeneic recipients. Table 15 shows the number of recipients whose PBL increased (↑), or decreased (↓), or did not change (⇌) their proliferative responses after the addition of 9.3 to anti-CD3 stimulated PBL. The parenthesis indicate percent of recipients whose proliferative responses increased after the addition of 9.3.

TABLE 15

| BTM RECIPIENTS | CHANGE | TREATMENT | |
|---|---|---|---|
| | | G19-4 + 9.3 | OKT3 + 9.3 |
| Autologous BMT | ↑ | 9 (60%) | 9 (82%) |
| | ↓ | 3 (20%) | 2 (18%) |
| | ⇌ | 3 (20%) | 0 (0%) |
| Allogeneic BMT | ↑ | 11 (69%) | 8 (62%) |
| | ↓ | 5 (31%) | 5 (38%) |
| | ⇌ | 0 (0%) | 0 (0%) |

Costimulation of G19-4+9.3 or OKT3+9.3 significantly increased proliferative responses induced by G19-4 or OKT3 alone (p<0.05, paired rank-sum) in ABMT recipients. In summary, defects in anti-CD3-induced T cell proliferation in BMT recipients were repaired by costimulation with 9.3. These findings have therapeutic implications for patients with immune defects manifest with impaired T cell proliferation. Indeed similar results have been obtained which indicate that the proliferative defect of T cells from patients with HIV infection can be repaired with anti-CD28 treatment. See Lane, H. C. et al., *J. Engl. J. Med.*, 313:85 (1985) regarding proliferate defects in HIV.

Costimulation with anti-CD3 OKT3 and anti-CD28 9.3 enhanced detectable mRNA levels for IL-2 in PBL from ABMT recipient. PBL from a short-term ABMT recipient were studied for expression of mRNA levels for IL-2 after stimulation with OKT3 and costimulation with OKT3/9.3 using RTase-PCR. cDNA synthesized by RTase from total RNA was amplified by PCR using specific primers for IL-2 and the PCR products run on 1.5% agarose gels containing ethidium bromide. Consistent with the findings in the previous paragraph, activated T cells from the ABMT recipient did not have detectable levels of mRNA for IL-2 after OKT3 stimulation alone, whereas the same T cells costimulated with OKT3/9.3 had a distinct band for IL-2 of 458 bp detected on ethidium bromide stained agarose gel. This is an example of how OKT3/9.3 costimulation can repair an apparent defect in the expression of mRNA for IL-2 in T cells from ABMT recipients.

Stimulation of negatively selected CD4$^+$ cells with anti-CD28 9.3 after activation with anti-CD3 induces IL-2 independent proliferative responses. CD4$^+$ cells were purified by a series of negative selection steps as previously described in Thompson, C. B. et al., *PNAS (USA)* 86:1333–1337 (1989). PBL were incubated with a cocktail of mAbs directed at non-CD28$^+$ cells, washed, and incubated with immunomagnetic bead coated with goat anti-mouse antibody. The CD28$^+$ enriched cells were further purified by removing the CD8$^+$ cells by treatment with anti-CD8 and binding the CD8$^+$ cells to the immunomagnetic beads.

Figure 18:
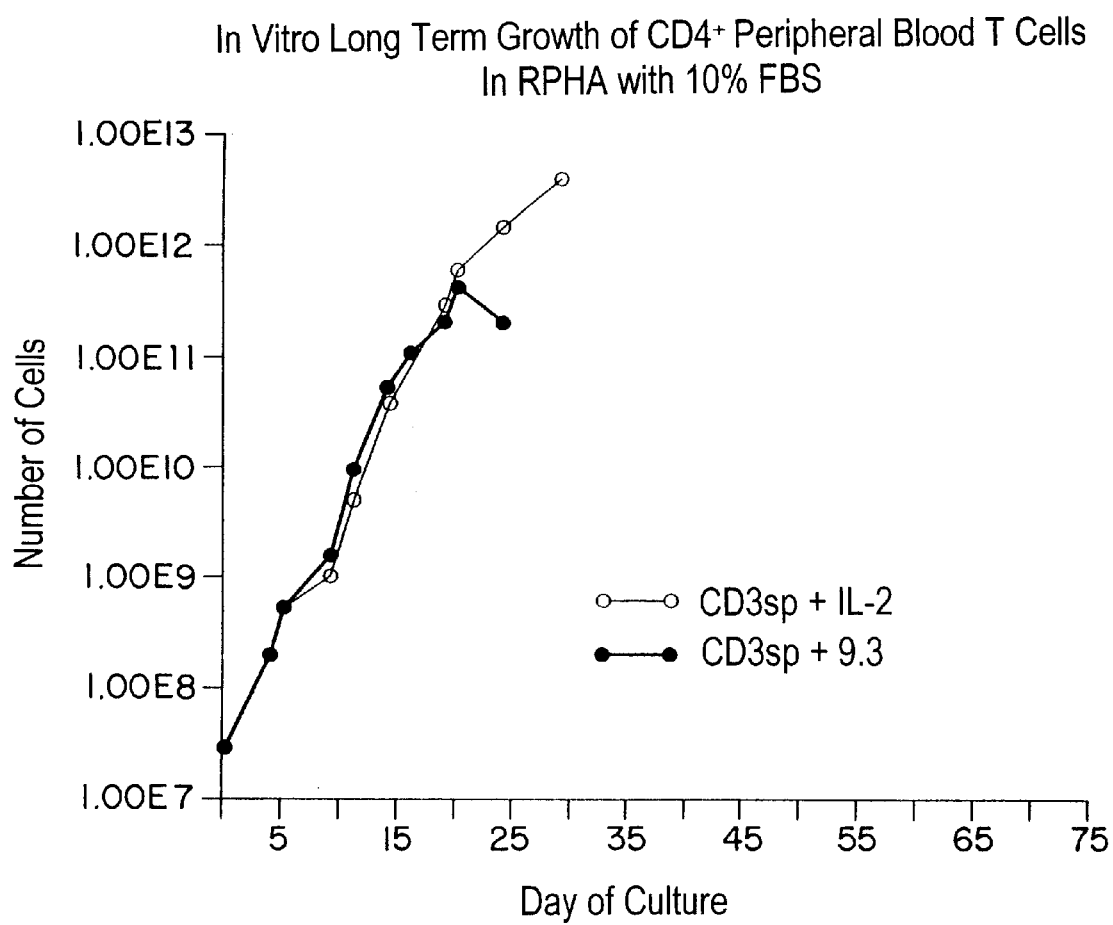
FIG. 18 is a graph showing in vitro long term growth of $CD4^+$ peripheral blood T cells propagated with anti-CD3 and anti-CD28.

The remaining CD28$^+$, CD4$^+$ T cells from a normal donor were cultured by adding cells to culture dishes containing plastic adsorbed OKT3. After 48 h, the cells were removed and placed in flasks containing either rIL-2 (200 IU/ml) or anti-CD28 mAb (100 ng/ml). The cells were fed with fresh medium as required to maintain a cell density of 0.5×10$^6$/ml, and restimulated at approximately weekly intervals by culture on plastic adsorbed OKT3 for 24 h. The cells could be maintained in logarithmic growth, with a 4 to 5 log$_{10}$ expansion in cells number. As shown in FIG. 18, cells propagated with anti-CD3 and anti-CD28 routinely expanded 10 to 30-fold more than cells grown in optimal amounts of anti-CD3 and IL-2. When synthetic medium (X-Vivo 10) not containing FBS was used, anti-CD3 plus anti-CD28 treated cells also expanded 10-fold better than anti-CD3 plus IL-2 treated cells. The highly enriched CD4 cells did not proliferate in the presence of optimal amounts of the lectin phytohemagglutinin (PHA). Thus, the in vitro expansion of CD4 cells using anti-CD28 has an advantage over previously described methods, in that it is independent of the addition of exogenous growth factors, as no IL-2 or any other growth factors were added to these cells. In addition, this system does not require the presence of accessory cells, which is advantageous in clinical situations where accessory cells are limiting or defective.

Phenotypes of anti-CD3 activated T cells. Populations of CTC cells grown in IL-2 for 6 to 12 days contained predominantly CD3$^+$ cells (greater than 84%, median 88%). The proportion of CD56$^+$ cells (a marker for NK cells) was less than 1.3%. Triggering of E$^+$ cells with OKT3 is preferentially selecting CD3$^+$ cells. CD4$^+$ cells were 18% or less and CD8$^+$ cells were greater than 66%. Lytic activity did not correlate with the proportions of CD56$^+$ cells in the cultures.

Immunophenotype of T cells differs after anti-CD28 and IL-2-mediated cellular growth. To examine the subsets of T cells that are expanded, PBL were propagated for 16 days using either anti-CD3 and IL-2 or anti-CD3 and anti-CD28. The percentage of CD4 and CD8 cells was 23.8 and 84.5 in the cells grown in IL-2, and 56.0 and 52.6 in the cells grown in CD28. These results suggests that CD28 expansion favors the CD4+ cells, in contrast to the well established observation that CD8+ cells predominate in cells grown in IL-2 (for example, see above paragraph; see also Cantrell, D. A. et al., *J. Exp. Med.* 158:1895 (1983)). To further test this possibility, CD4 cells were enriched to 98% purity using negative selection with monoclonal antibodies and magnetic immunobeads as described elsewhere in this example. The cells were cultured for one month using anti-CD3 and either IL-2 or anti-CD28 to propagate the cells. There was equal expansion of the cells for the first 26 days of the culture, however, as can be seen in Table 16, the phenotype of cells diverged progressively with increasing time in culture.

TABLE 16

| CULTURE METHOD | DAYS | CD3 (%) | CD4 (%) | CD8 (%) |
|---|---|---|---|---|
| anti-CD3 + IL-2 | 0 | >99 | >99 | <1 |
|  | 6 | >99 | 98 | 1 |
|  | 12 | >99 | 85 | 10 |
|  | 20 | >99 | 45 | 40 |
|  | 26 | >99 | 12 | 78 |
| anti-CD3 + IL-2 | 0 | >99 | >99 | <1 |
|  | 6 | >99 | >99 | <1 |
|  | 12 | >99 | >99 | <1 |
|  | 20 | >99 | >99 | <1 |
|  | 26 | >99 | >99 | <1 |

Use of anti-CD28 for in vitro expansion of TIL The use of IL-2 and inactivated tumor cells to expand tumor infiltrating lymphocytes (TIL cells) for later adoptive immunotherapy with a variety of neoplasms has demonstrated promise (e.g., see Rosenberg, S. A. et al., *NEJM* 323:570–578 (1990)). TIL cells were isolated from a nephrectomy specimen from a patient with renal cell carcinoma. The cells were cultured with tumor cells, and either IL-2 or anti-CD28 and IL-2 with mAb OKT3 added at weekly intervals, beginning at day 14. Table 17 demonstrates that anti-CD28 is an improved method for the propagation of these cells in some patients, with a 20-fold greater yield of cells. Immunophenotype analysis also reveals that CD4 T cells are expanded in "TIL" cultures. Furthermore, these cells also exhibited potent cytotoxic activity against DAUDI targets, with 82.8, 69.7, 78.8 and 101.5 percent specific lysis at effector to target ratios of 40:1, 20:1, 10:1 and 5:1.

TABLE 17

Use of anti-CD28 to Expand TIL cells

| Day of Culture | Tumor cells + IL-2 (1000 U/ml) | Tumor cells + IL-2 anti-CD3, then anti-CD28 |
|---|---|---|
| 0 | $3.6 \times 10^7$ | $3.6 \times 10^7$ |
| 5 | $5.8 \times 10^7$ | $1.3 \times 10^8$ |
| 12 | $1.7 \times 10^8$ | $1.4 \times 10^8$ |
| 16 | $2.0 \times 10^8$ | $2.6 \times 10^8$ |
| 19 | $3.8 \times 10^8$ | $4.8 \times 10^8$ |
| 25 | $2.9 \times 10^8$ | $9.0 \times 10^8$ |
| 36 | $3.7 \times 10^8$ | $1.8 \times 10^9$ |
| 43 | $3.0 \times 10^8$ | $3.2 \times 10^9$ |
| 48 | $2.3 \times 10^8$ | $5.1 \times 10^9$ |

Figure 19:
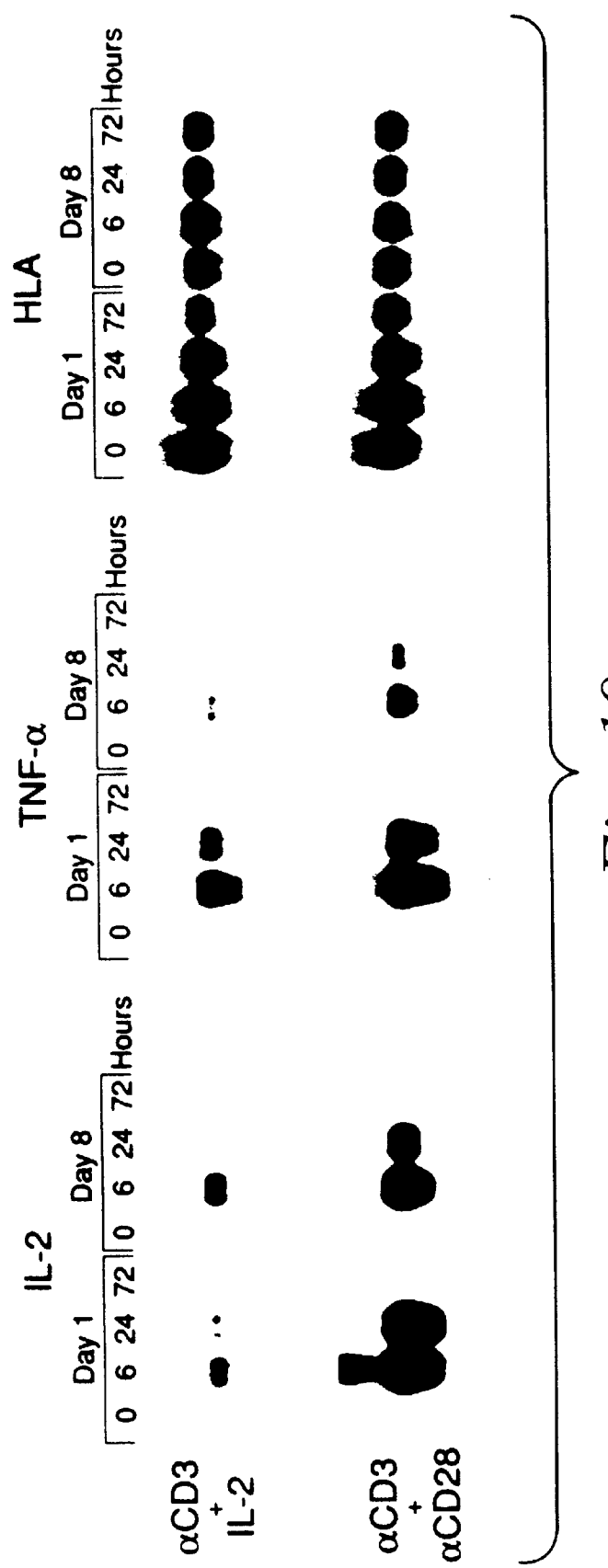
FIG. 19 is a Northern blot analysis of the enhancement of MRNA for IL-2 and TNF-α after costimulation with anti-CD3 and anti-CD28.

Anti-CD3 and anti-CD28 costimulation enhances expression of mRNA for IL-2 and TNF-α in CD4+ cells. To examine whether CD4 cells propagated in vitro by anti-CD28 might be an effective source of lymphokines, resting CD4 cells were stimulated by anti-CD3 mAb for 48 h followed by the addition of 50 IU/mi of recombinant IL-2 and compared with CD4 T cells costimulated with anti-CD3 and anti-CD28. Total RNA was harvested from each combination. A total of 10 μg of RNA was loaded into each lane. A class I probe (HLA B7) was used to show uniform loading. The blot was hybridized with $^{32}$P labeled probes specific for IL-2, TNF-α and HLA in succession. On days 1 and 8, the cultures were restimulated with anti-CD3 mAb in the presence of IL-2 or anti-CD28 mAb 9.3 (0.1 μg/ml). The blots were stripped, and rehybridized with a probe for a constant region of HLA class I mRNA, to demonstrate equal loading of the lanes. As illustrated by the Northern Blot of FIG. 19, there was a clear enhancement of mRNA for IL-2 and TNF-α after costimulation with anti-CD3 and anti-CD28 and the IL-2 and TNF-α mRNA exceeded that of the IL-2 propagated cells by 10 to 50-fold. Similar results were obtained when the culture was examined for one month of culture, after weekly restimulation with anti-CD3 and IL-2 or anti-CD28.

Supernatants from long-term anti-CD3 and anti-CD28 stimulated cultures of CD4+ cells contain substantial amounts of IL-2, GM-CSF, and TNF-α. After anti-CD3 stimulation in the presence of 200 IU/ml of IL-2 or the combination of anti-CD3 and anti-CD28 in the absence of IL-2, supernatants were tested for IL-2 content using the CTLL-2 cell line, GM-CSF content by ELISA, and TNF-α content by ELISA. The CD4+ cells were restimulated with anti-CD3 and IL-2 or anti-CD3 and anti-CD28 respectively at approximately weekly intervals. Anti-CD3 and anti-CD28 cultures of CD4+ cells produced roughly the same amount of IL-2 found in supernatant obtained from anti-CD3 activated cells grown in exogenous IL-2. The amount of GM-CSF produced by anti-CD3 and anti-CD28 stimulated CD4+ cells was also substantial. Although there were variations in levels of TNF-α depending on when the supernatants were tested, costimulation with anti-CD3 and anti-CD28 was superior to stimulation with anti-CD3 and IL-2 for inducing mRNA for TNF-α. These data indicate that anti-CD28 costimulation with anti-CD3 may not only replace some of the functions of IL-2 but may enhance other synthetic functions of CD4+ cells.

SPECIFIC EXAMPLE XV

CD28 and CTLA-4 Expression Studies

CTLA-4 expression limited to CD28+ T cells. Utilizing site-specific primers and DNA PCR of human genomic DNA, a 348 bp fragment corresponding to exon II of human CTLA-4 was generated, gel purified and used as a $^{32}$P-labeled probe. Purified human T cells were separated into CD28+ and CD28− fractions by negative selection with magnetic bead immunoabsorbtion. CD28− T cells were either tested in media or stimulated with PMA+ionomycin or PMA+anti-CD28 mAb (mAb 9.3) for 12 h. CD28+ cells were stimulated with the last two conditions for 12 h. RNA was extracted by guanidinium isothicyanate and purified over cesium chloride gradients. Equal amounts of RNA (as determined by ethidium bromide staining) were loaded and separated on a formaldehyde-agarose gel and transferred to nitrocellulose to demonstrate equal loading of RNA. This blot was subsequently probed with the CTLA-4 probe generated above. CTLA-4 was expressed in CD28+ cells following PMA or PMA+mAb 9.3 stimulation but not expressed in resting or stimulated CD28− cells. The same blot was hybridized to a HLA probe to confirm equal loading of RNA.

The expression of CTLA-4 induced under conditions causing CD28 pathway activation. Purified resting CD28+ T cells were stimulated with PMA alone, ionomycin 30 alone, and PMA+ionomycin for 1 h, 6 h, 12 h and 24 h. RNA was extracted and analyzed by hybridization to CD28 and CTLA-4 probes. Northern blot analysis showed that CTLA-4 expression was induced by PMA or PMA+ionomycin, conditions which are costimulatory with CD28 pathway activation. CTLA-4 expression was not induced by ionomycin, which is not costimulatory with CD28 pathway activation. In contrast, CD28 expression was constant with ionomycin or PMA and even appeared to be suppressed with PMA and ionomycin stimulation. It should also be noted that the induction of CTLA-4 expression occurred as soon as 1 h after stimulation, compared to 6–12 h with IL-2 expression following CD28 pathway activation. Since expression of CTLA-4 precedes the biological events caused by CD28 pathway activation (i.e. enhanced IL-2 expression), CTLA-4 expression likely plays a role in the generation of later events.

Purified human T cells were either untreated or stimulated for 1 h, 4 h or 23 h with PMA +PHA, anti-CD28 mAb crosslinked with a second antibody (goat anti-mouse lg), or anti-CD5 mAb crosslinked in the same manner. Northern blot analysis showed that crosslinking of CD28 receptors, which also can activate the CD28 pathway through mechanisms distinct from PMA and ionomycin, also induced CTLA-4 expression.

CD28+ cell lines slightly or not responsive to CD28 pathway activation do not express CTLA-4. Two cell lines that are CD28+ but responded poorly (T cell line Jurkat C J) or not at all (myeloma cell line RPMI-8226) to CD28 costimulation as discussed in Kozbor, D. et al., *J. Immunol.*, 138:4128–4132 (1987) and Ledbetter, J. A. et al., *PNAS (USA)*, 84:1384–1388 (1987), were stimulated with PMA +ionomycin +mAb 9.3 and subsequently analyzed by Northern blot for CD28 and CTLA-4 expression. Northern blot analysis of the T cell leukemia cell line Jurkat CJ and of the myeloma cell line RPMI 8226 showed that these cell lines did not express CTLA-4 despite CD28 expression.

Figure 20:
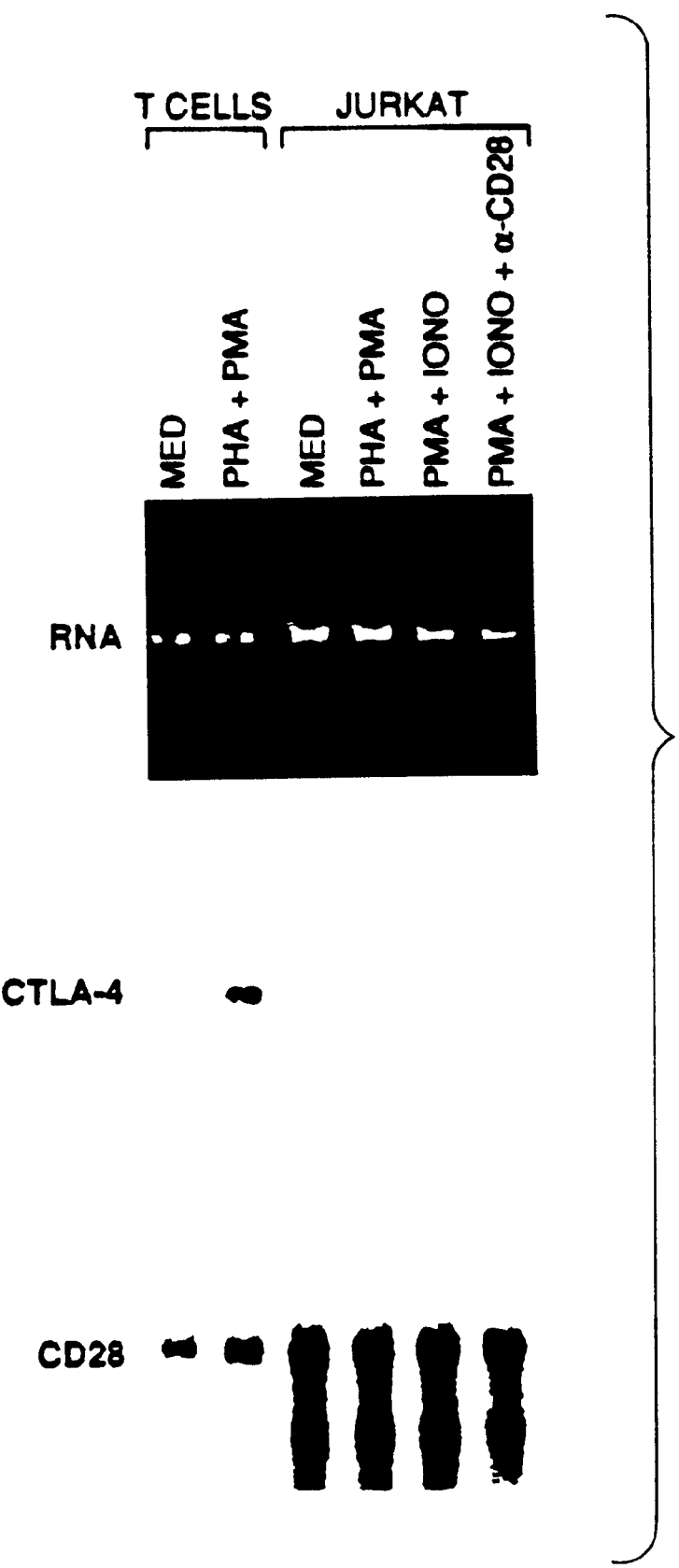
FIG. 20 is a Northern blot analysis of the ability of mitogens to induce CTLA-4 mRNA expression.

T cells were incubated with various combinations of mitogens including phytohemagglutinin (PHA), phorbol myristate acetate (PMA), and ionomycin (IONO), or anti-CD28 monoclonal antibodies (α-CD28), and examined for the ability to induce CTLA-4 mRNA expression. As shown in FIG. 20, the combination of the mitogens PHA and PMA readily induce CTLA-4 expression in normal human T cells, but all combinations tested failed to induce the expression of the CD28-isoform CTLA-4 in the Jurkat T cell line. Both cell types express significant levels of CD28 mRNA under all conditions tested.

Figure 21:
FIG. 21 is a Northern blot analysis of the induction of CTLA-4 mRNA expression by costimulation with anti-CD3 mAb and soluble anti-CD28 mAb.

Resting T cells were costimulated with anti-CD28 monoclonal antibodies to examine activation in normal human cells. As shown in FIG. 21, normal human T cells stimulated by plate-adherent anti-CD3 (α-CD3) monoclonal antibodies at a concentration of 1 μg/ml induced only low levels of CTLA-4 mRNA expression first observable at 1 h after stimulation. In contrast, costimulation of cells with anti-CD3 monoclonal antibodies (1 μg/ml) soluble anti-CD28 (α-CD28) monoclonal antibody (1 μg/ml) led to a dramatic increase in the induction of CTLA-4 mRNA expression.

SPECIFIC EXAMPLE XVI

Efficacy of Administration of CTLA-4Ig as a Treatment for Autoimmune Disease Experimental Autoimmune Encephalomyelitis (EAE) is a rodent and primate model for multiple sclerosis. Data has been generated on the effect of administration of CTLA-4Ig in both passive (indirect) and active (direct) models of EAE. CTLA-4Ig is a fusion protein consisting of the extracellular domain of human CTLA-4 fused to the constant region of human lgG1 (referred to here as huCTLA-4Ig).

Adoptively Transferred (Passive) EAE. In the passive EAE model, donor mice are immunized with 0.4 mg Myelin Basic Protein (MBP) in Complete Freund's Adjuvant (CFA), divided over four quadrants. The draining axillary and inguinal lymph nodes are removed eleven days later. Lymph node cells (4×10⁶/ml) are plated in 2 ml cultures in 24 well plates, in the presence of 25 μg/ml MBP. After four days in culture, 30×10⁶ of the treated cells are injected into the tail vein of each naive, syngeneic recipient mouse.

Figure 22:
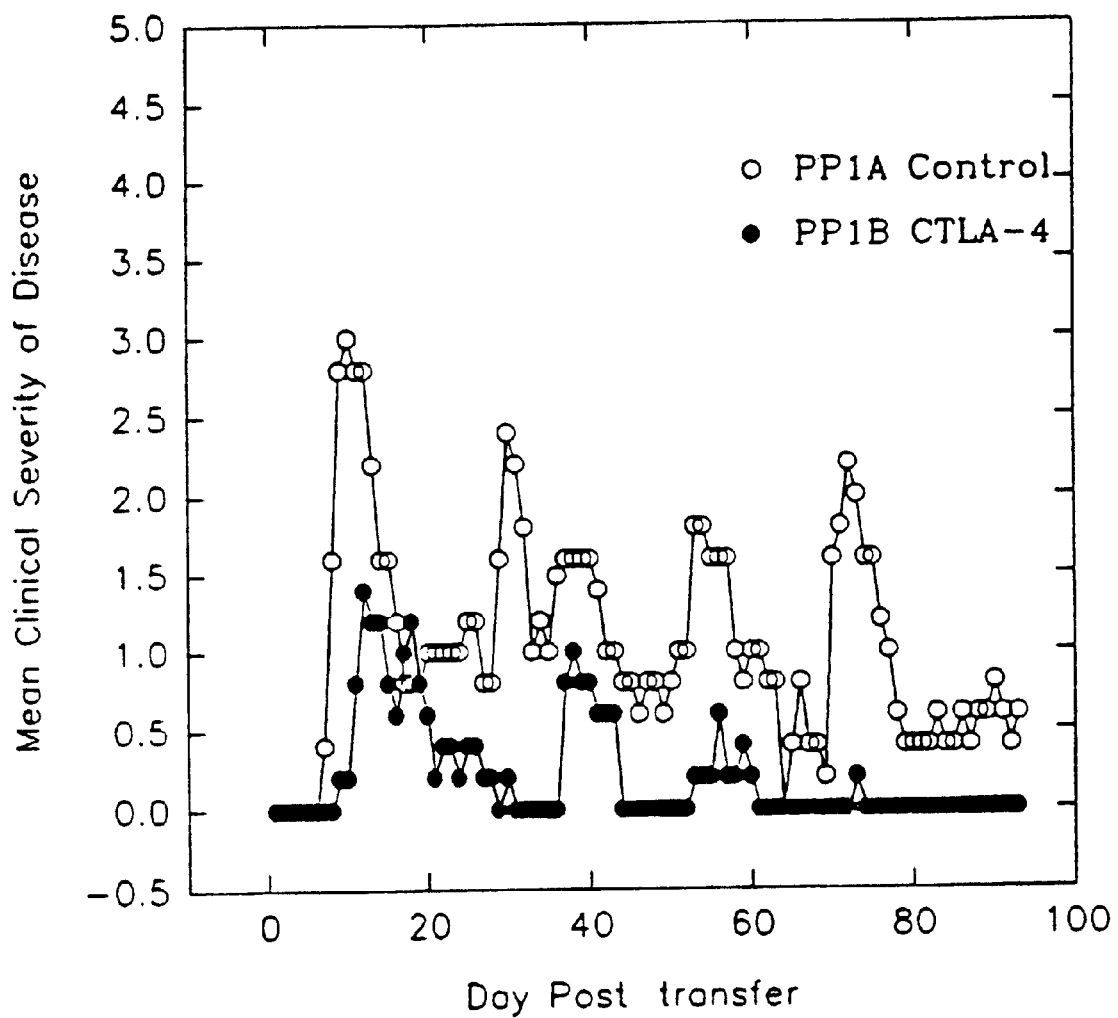
FIG. 22 is a graph illustrating the effects on disease progression of CTLA-4Ig treatment of syngeneic, MBP-sensitized cells used to adoptively transfer the murine autoimmune disease, Experimental Autoimmune Encephalomyelitis (EAE).

The recipient mice develop a remitting, relapsing disease and are evaluated utilizing the following criteria:
0—normal, healthy
1—limp tail, incontinence; occasionally the first sign of the disease is a "tilt"
2—hind limb weakness, clumsiness
3—mild paraparesis
4—severe paraparesis
5—quadriplegia
6—death Using this passive model of EAE, the effect of huCTLA-4Ig treatment of the donor cells on disease severity was tested in PLSJLF1/J mice. Treatment of lymph node cells in vitro with MBP was performed either in the presence or the absence of 30 μg/ml huCTLA-4Ig. The treated cells were then introduced into a syngeneic recipient mouse. As shown in FIG. 22, mice receiving huCTLA-4Ig-treated cells (designated PPIB CTLA-4) showed a significantly reduced severity of their first episode of disease as compared to mice receiving untreated cells (designated PPIA control). In addition, ensuing relapses in the mice receiving huCTLA-4Ig-treated cells were less severe than in mice receiving cells not exposed to huCTLA-4Ig. In fact, all five mice receiving huCTLA-4Ig-treated cells stopped relapsing, and no longer showed signs of disease at 80–100 days post transfer.

Figure 23:
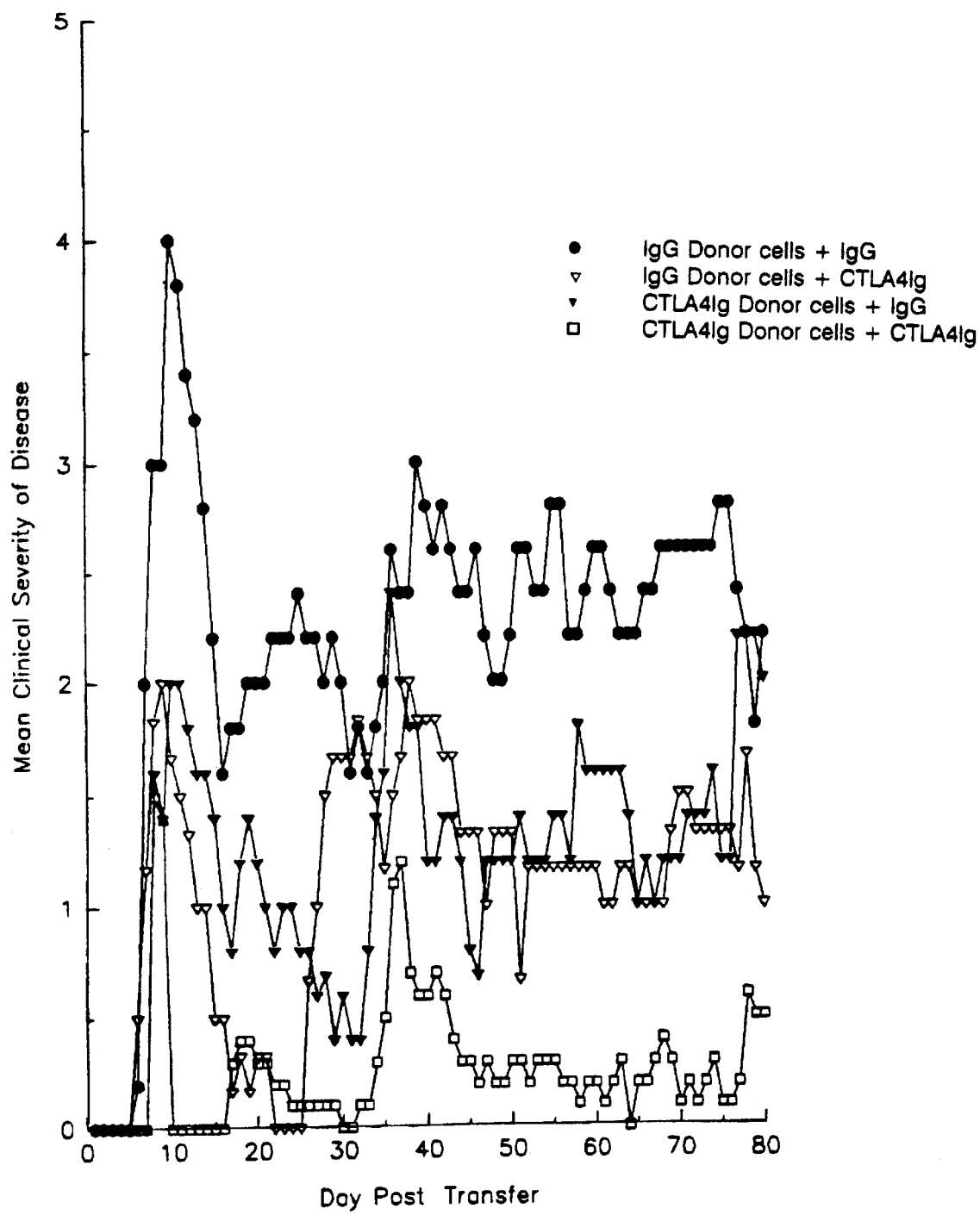
FIG. 23 is a graph illustrating the effect on disease progression of CTLA-4Ig or control lgG treatment of donor mice and/or isolated cells used to adoptively transfer EAE.

Clinical disease severity was reduced even further by treating both the donor mice and the cultured cells with huCTLA-4Ig (FIG. 23). In these experiments, donor mice of the SJL/J strain were given either 100 μg huCTLA-4Ig or 100 μg chimeric control lgG1 intraperitoneally each day for eleven days. T cells were then isolated from lymph nodes of these donors and cultured with MBP in vitro in the presence of either 30 μg/ml huCTLA-4Ig or chimeric control lgG1. The treated cells were then introduced into a syngeneic recipient. Treatment of either the donor mice or the in vitro cultures resulted in significantly reduced clinical disease severity. Treatment of both the donor mice and the cultured cells with huCTLA-4Ig was the most effective protocol for reducing clinical disease severity.

Figure 24:
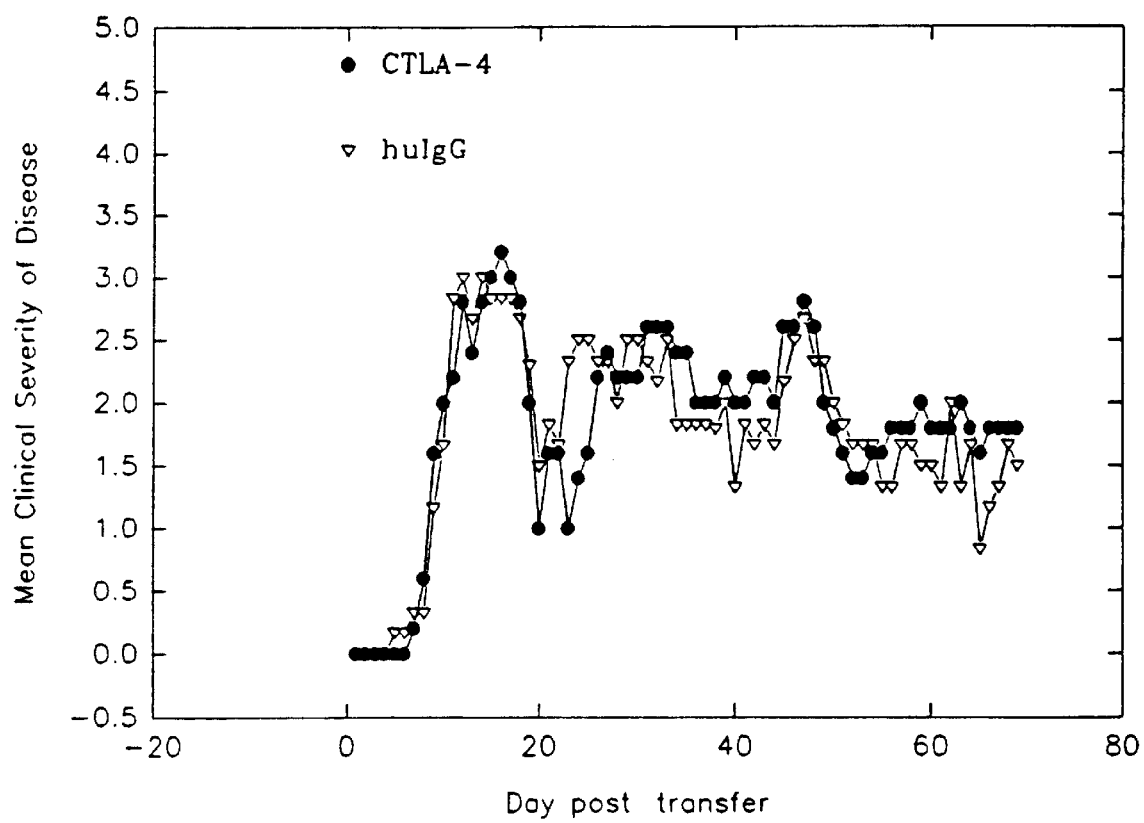
FIG. 24 is a graph depicting the effect on disease severity of direct administration of CTLA-4Ig or control human lgG to PLSJLFI/J mice with adoptively transferred EAE.
Figure 25:
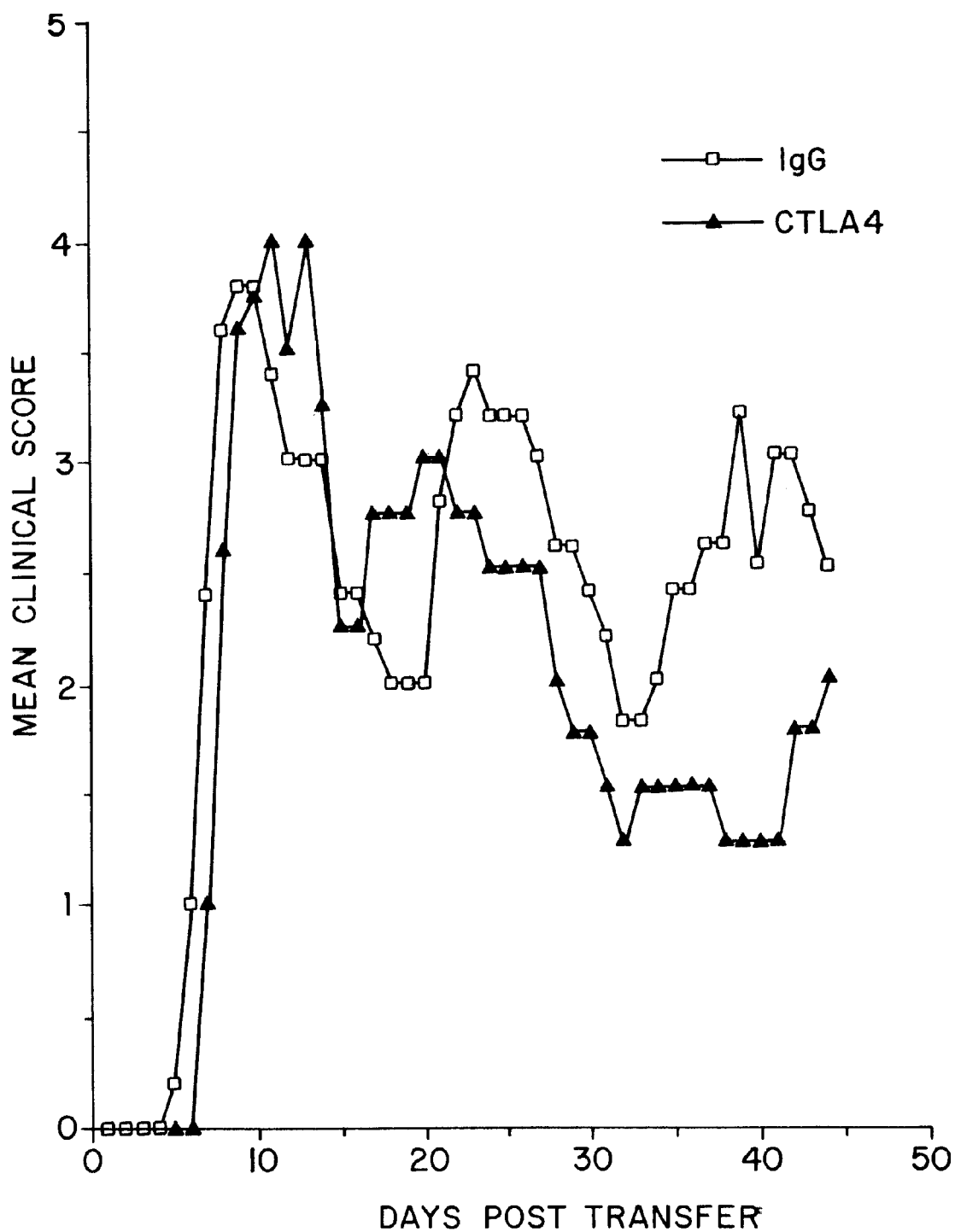
FIG. 25 is a graph illustrating the effect on disease progression of direct administration of CTLA-4Ig or control human lgG to SJL/J mice with adoptively transferred EAE.
Figure 26:
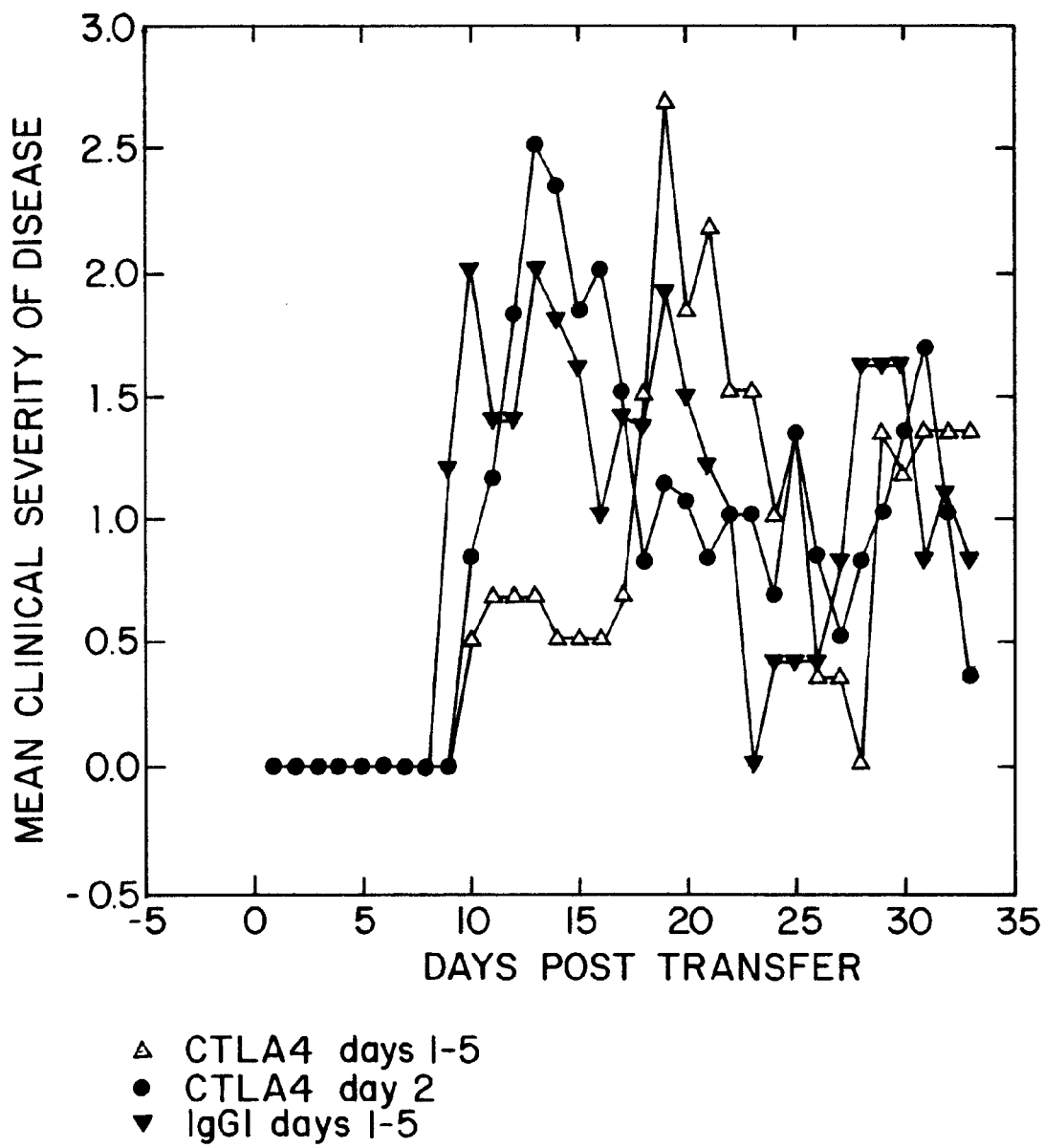
FIG. 26 is a graph depicting the effect of direct administration of CTLA-4Ig or lgG on disease severity in SJL/J mice with adoptively transferred EAE.

Direct administration of huCTLA-4Ig to mice receiving adoptively transferred cells was also examined. As shown in FIG. 24, when PLSJLFI/J recipient. mice were given 100 μg of either huCTLA-4Ig or human lgG in PBS intraperitoneally on days 1 to 9 post transfer, no difference in disease severity was observed between the two groups of mice. However, in experiments utilizing SJL/J mice, reduced disease severity during relapse was noted in mice treated with 100 μg huCTLA-4Ig intraperitoneally on days 1 to 5 post transfer (FIG. 25). Ongoing experiments are examining the effect of administration of a single dose of huCTLA-4Ig to SJL/J recipient mice on day 2 post transfer. Table 18 shows results of such an experiment, compared to the results obtained when recipient mice are given either huCTLA-4Ig or human lgG1 on days 1 to 5 post transfer. While severity of the first episode of disease did not appear to be significantly altered by treatment with huCTLA-4Ig either on day 2 or days 1–5, the duration of the first episode of disease was shorter for mice given huCTLA-4Ig treatment (Table 18). In addition, huCTLA-4Ig treatment on days 1–5 resulted in delayed onset of the first episode of disease.

TABLE 18

Effect of Administration of CTLA-4Ig to Mice with Adoptively Transferred EAE

|  | CTLA-4Ig (day 2) | CTLA-4Ig (days 1–5) | IgG Control (days 1–5) |
| --- | --- | --- | --- |
| Mean day of onset | 11.3 | 16.3 | 10.8 |
| Maximum score of first episode | 3.2 | 2.8 | 2.8 |
| Maximum score to date (day 35) | 3.5 | 3.2 | 3.0 |
| Average of first episode (days) | 5.2 | 6.7 | 9.8 |

Figure 27:
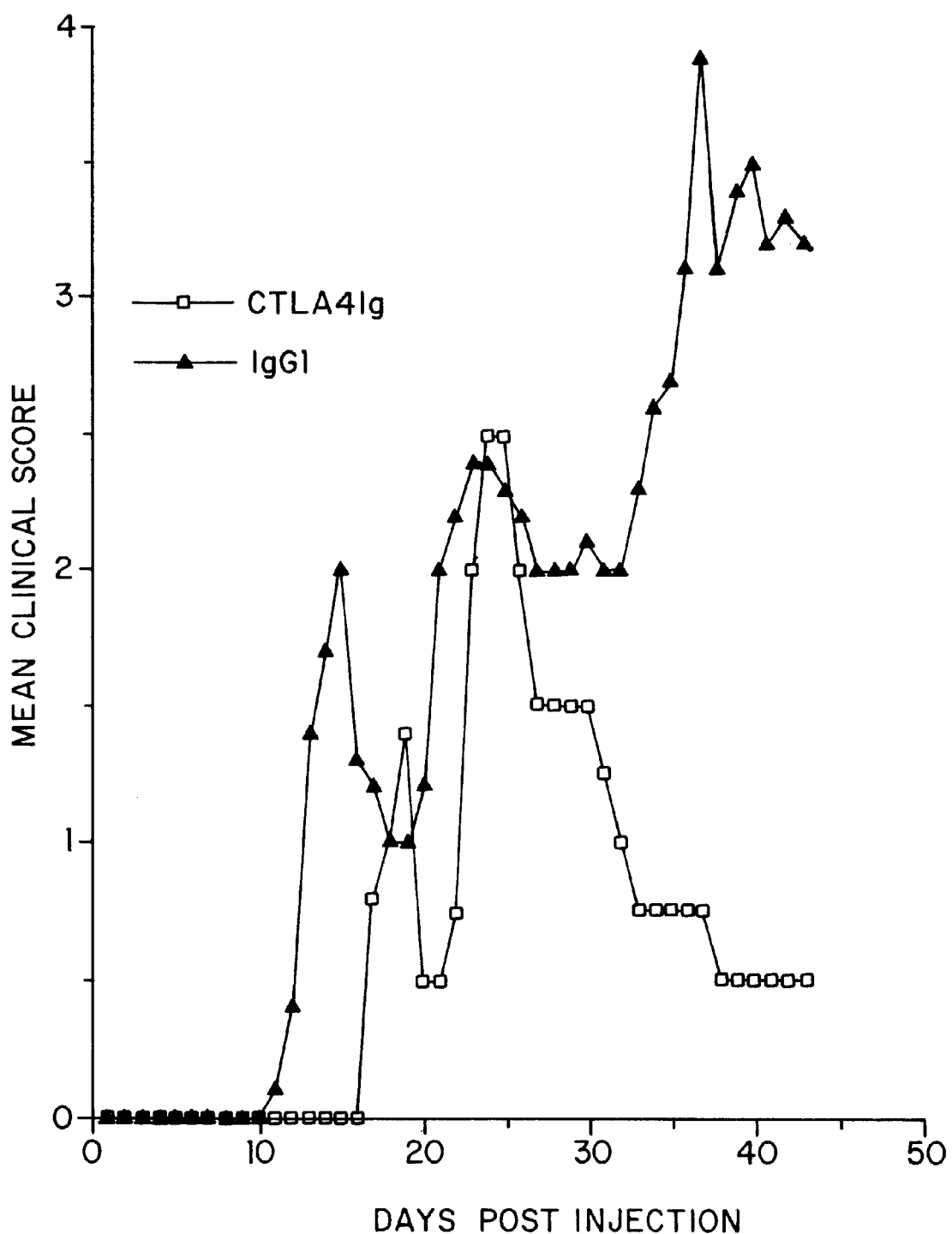
FIG. 27 is a graph illustrating the effect on disease severity of direct administration of CTLA-4Ig or control lgG to PLSJLFI/J mice directly immunized with MBP and treated with PT.

Direct (Active) Model of EAE. Studies using a direct (active) model of EAE have also been conducted. In these experiments, huCTLA-4Ig was directly administered to mice immunized with MBP and treated with pertussis toxin (PT). PLSJLFI/J mice immunized with MBP on day 0 and injected with PT intravenously on days 0 and 2 were given either huCTLA-4Ig or control lgG1 on days 0 to 7. Five of ten mice given huCTLA-4Ig died on days 5 to 7, for reasons related to the PT administered, and not the experimental design. The results of the experiment for the remaining five mice are as shown in FIG. 27. Administration of huCTLA-4Ig markedly reduced the mean clinical severity of disease in these animals, as compared to the mice treated with lgG1. These findings indicate that direct administration of soluble human huCTLA-4Ig can provide an effective therapeutic strategy in the treatment of autoimmune disease.

It should be appreciated that a latitude of modification, change or substitution is intended in the foregoing disclosure and, accordingly, it is appropriate that the appended claims be construed broadly and in a manner consistent with the spirit and scope of the invention herein.

All publications and applications cited herein are incorporated by reference.

What is claimed is:

1. A method of treating a patient having multiple sclerosis comprising administering to the patient CTLA-4Ig in an amount effective to suppress the patient's immune response.

2. A method of treating a patient having systemic lupus erythematosis comprising administering to the patient CTLA-4Ig in an amount effective to suppress the patient's immune response.

3. A method of treating a patient having rheumatoid arthritis comprising administering to the patient CTLA-4Ig in an amount effective to suppress the patient's immune response.

4. A method of treating a patient having scleroderma comprising administering to the patient CTLA-4Ig in an amount effective to suppress the patient's immune response.

5. The method of claim 1, further comprising the step of administering an additional immunosuppressant to the patient.

6. The method of claim 2, further comprising the step of admninistering an additional immunosuppressant to the patient.

7. The method of claim 3, further comprising the step of administering an additional immunosuppressant to the patient.

8. The method of claim 4, further comprising the step of administering an additional immunosuppressant to the patient.

9. The method of claim 5, wherein the additional immunosuppressant comprises cyclosporine.

10. The method of claim 6, wherein the additional immunosuppressant comprises cyclosporine.

11. The method of claim 7, wherein the additional immunosuppressant comprises cyclosporine.

12. The method of claim 8, wherein the additional immunosuppressant comprises cyclosporine.

13. The method of claim 5, wberein the CTLA-4Ig to the patent parenterally.

14. The method of claim 6, wherein the CTLA-4Ig to the patient parenterally.

15. The method of claim 7, wherein the CTLA-4Ig to the patient parenterally.

16. The method of claim 8, wherein the CTLA-4Ig to the patient parenterally.

17. The method of claim 1, wherein the CTLA-4Ig is administered to the patient parenterally.

18. The method of claim 2, wherein the CTLA-4Ig 4Ig is administered to the patient parenterally.

19. The method of claim 3, wherein the CTLA-4Ig 4Ig is administered to the patient parenterally.

20. The method of claim 4, wherein the CTLA-4Ig 4Ig is administered to the patient parenterally.

* * * * *